US006602687B1

(12) United States Patent
Sendtner et al.

(10) Patent No.: US 6,602,687 B1
(45) Date of Patent: Aug. 5, 2003

(54) DNA ENCODING HUMAN CILIARY NEUROTROPHIC FACTOR AND METHOD FOR PRODUCING THE PROTEIN ENCODED THEREBY

(75) Inventors: Michael Sendtner, Munich (DE); Kurt Stockli-Rippstein, Munich (DE); Friedrich Lottspeich, Neuried (DE); Yoshihiro Arakawa, Munich (DE); Patrick Desmond Carroll, Munich (DE); Rudolf Georg Gotz, Munich (DE); Georg W. Kreutzberg, Munich (DE); Dan B. Lindholm, Munich (DE); Piotr Masiakowski, Tarrytown, NY (US); Vivien Wong, Ardsley, NY (US); Nancy Ip, Stamford, CT (US); Mark E. Furth, Pelham, NY (US); Nikos Panayotatos, Orangeburg, NY (US); Hans Thoenen, Munich (DE)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 07/883,630

(22) Filed: May 8, 1992

Related U.S. Application Data

(60) Division of application No. 07/570,651, filed on Aug. 20, 1990, now abandoned, which is a continuation-in-part of application No. 07/429,517, filed on Oct. 31, 1989, now abandoned, which is a continuation-in-part of application No. 07/408,172, filed on Sep. 15, 1989, now abandoned.

(51) Int. Cl.$^7$ .......................... C12N 15/16; C12N 5/10; C12N 15/63; C07K 14/575
(52) U.S. Cl. .................... 435/69.4; 435/71.1; 435/71.2; 435/252.3; 435/254.11; 435/252.33; 435/320.1; 435/471; 435/325; 536/23.1; 536/23.51; 530/399
(58) Field of Search .................. 435/320.1, 254.11, 435/471, 325, 252.33; 453/252.3, 252.31, 320.1, 69.1, 69.4, 70.1, 70.3, 71.1, 71.2; 536/23.1, 23.51; 530/399

(56) References Cited

U.S. PATENT DOCUMENTS

| | | |
|---|---|---|
| 4,923,696 A | 5/1990 | Appel et al. |
| 4,997,929 A | 3/1991 | Collins et al. |
| 5,011,914 A | 4/1991 | Collins et al. |
| 5,141,856 A | 8/1992 | Collins et al. |

OTHER PUBLICATIONS

Mikayama et al. Proc. Natl. Acad. Sci. USA vol. 90, pp. 10056–10060, 1993.*
Voet et al. Biochemistry. John Wiley & Sons, Inc., pp. 126–128, and pp. 228–234, 1990.*
"Product Update," Clontech Laboratories, Inc., Palo Alto, California, available Jun. 1986, p. 8.
"The 1988 Clontech Products and Protocols Catalog," Clontech Laboratories, Inc., Palo Alto, California, available May 1, 1988, pp. 1.6 and 1.11.
"Clontech Libraries," Clontech Laboratories, Inc., Palo Alto, California, available Apr., 1988.
Manthorpe et al., 1986, Brain Research 367:282–286.
Goeddel, 1990, Meth. Enzymol. 185:3–7.
Kaufman, 1990, Meth. Enzymol. 185:487–511.
Benton and Davis, 1977, Screening γgt Recombinant Clones by Hybridization to Single Plaques in situ, Science 196:180–182.
Grunstein and Hogness, 1975, Colony Hybridization: A method for the isolation of cloned DNAs that contain a specific gene, Proc. Natl. Acad. Sci. USA 72:3961–3965.
Mahmoudi and Lin, 1989, Comparison of Two Different Hybridization Systems in Northern Transfer Analysis, BioTechniques 1:331–333.
Negro et al., 1991, J. Neurosci. Res. 29: 251–260.
McManaman et al., 1990, Neuron 4:891–8989.
McManaman et al., 1989, J. Neurochem. 53:1763–1771.
Ernsberger et al., 1989, Neuron 2:1275–1284.
Blottner et al., 1989, Neuroscience Lett. 105:316–320.
Saadat et al., 1989, J. Cell. Biol. 108:1807–1816.
Manthorpe et al., 1989, in "Nerve Growth Factors", Rush, ed., John Wiley & Sons, pp. 31–56.

(List continued on next page.)

*Primary Examiner*—Prema Mertz
(74) *Attorney, Agent, or Firm*—Pennie & Edmonds LLP

(57) ABSTRACT

The present invention relates to nucleic acid sequences encoding ciliary neurotrophic factor (CNTF) and to the proteins, peptides, and derivatives produced therefrom. In various embodiments of the invention, the nucleic acid sequences, proteins, and peptides of the invention may be used in the treatment of a variety of neurological diseases and disorders, including Alzheimer's disease. In a specific embodiment of the invention, CNTF may be used to support the growth of spinal cord neurons, thereby providing a method of treating spinal cord damage caused by trauma infarction, infection, nutritional deficiency or toxic agents.

Figure 1A:
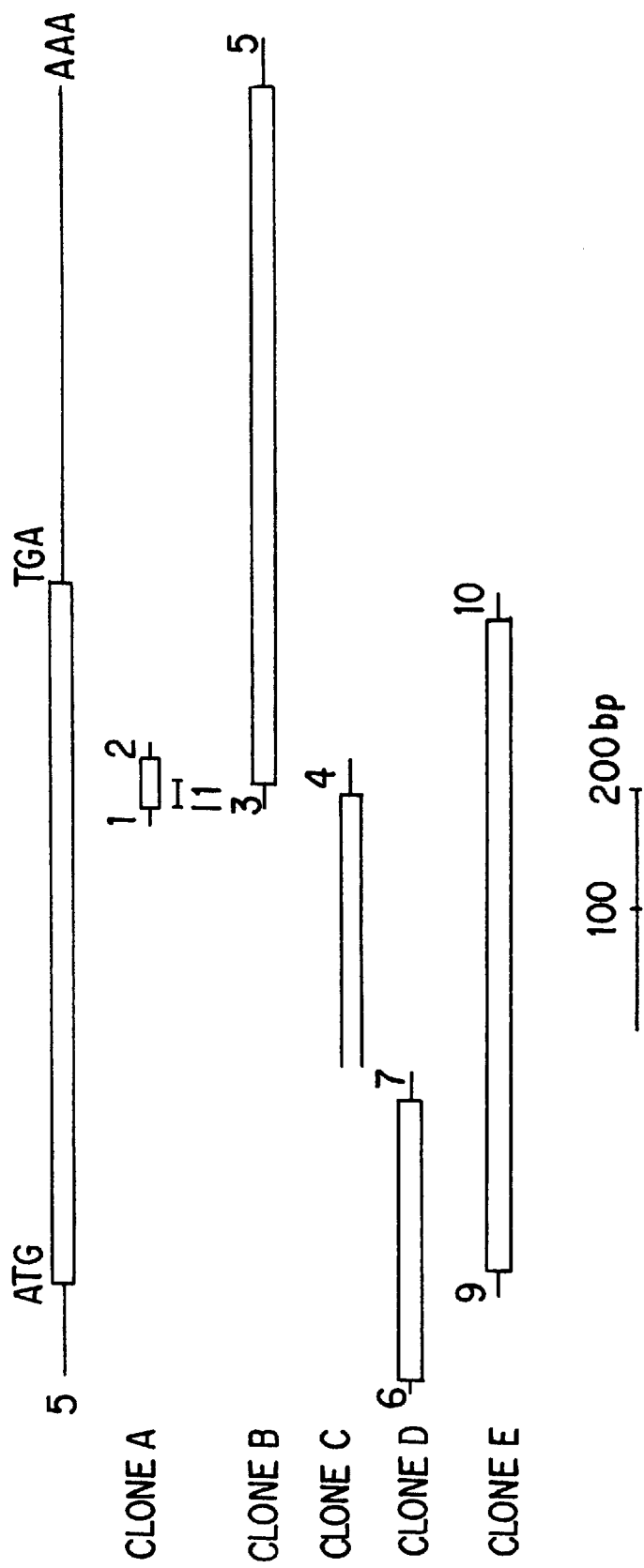

The present invention also relates to a novel method for producing substantilly pure CNTF.

The invention also relates to pharmaceutical compositions comprising effective amounts of CNTF gene products which may be used in the diagnosis and treatment of a variety of neurologial diseases and disorders.

The present invention relates to the cloning sequencing and expression of CNTF and provides, for the first time, a means for producing human CNTF utilizing human CNTF-encoding nucleic acid sequences. Furthermore, the CNTF nucleic acid sequences of the invention may be utilized to identify nucleic acid sequences encoding CNTF or CNTF-homologous molecules in a variety of species and tissues.

32 Claims, 68 Drawing Sheets

OTHER PUBLICATIONS

McManaman et al., 1988, J. Biol. Chem. 263:5890–5897.
Oppenheim and Haverkamp, 1988, in "Plasticity of the neuromuscular system," Wiley, Chichester (Ciba Foundation Symposium 138) pp. 152–171.
Oppenheim et al., 1988, Science 240:919–922.
Dohrmann et al., 1987, Dev. Biol. 124:145–152.
Dohrmann et al., 1986, Dev. Biol. 118:209–221.
Eagleson and Bennett, 1983, Neurosci. Lett. 38:187–192.
Oppenheim et al., 1991, Science 252:1616–1618.
Arakawa et al., 1990, J. Neurosci. 10:3507–3515.
Sendtner et al., 1990, Nature 345:440–441.
Adler et al., 1979, Science 204:1434–1436.

* cited by examiner

```
  1   AGTCACATTTCTTATTTGGACTAGTGAAGACAGAAGCAAACCAGCTCACTTGTCCTGGGACAGTTGATT

72   TAGGGGATGGCTTTCGCAGAGCAAACACCTCTGACCCTTCACCGCCGGGACCTCTGTAGCCGTTCTATCTGG
  1                  *  M  A  F  A  E  Q  T  P  L  T  L  H  R  R  D  L  C  S  R  S  I  W
                                                                                        T8

145   CTAGCAAGGAAGATTCGTTCAGACCTTCAGACCTGCTCTTATGGAATCTTATGTAAAACATCAGGGCCTGAATAAA
 23    L  A  R  K  I  R  S  D  L  T  A  L  M  E  S  Y  V  K  H  Q  G  L  N  K
                     T6

217   AATATCAACCTTGACTCAGTGGATGGTGTACCAGTGGCAAGCACTGATCGTTGGAGTGAGATGACTGAGGCA
 47    N  I  N  L  D  S  V  D  G  V  P  V  A  S  T  D  R  W  S  E  M  T  E  A
           T3                                    T5

289   GAGCGACTCCAAGAGAACCTCCAGGCTTACCGTACCTTCCAAGGGATGTTAACCAAGCTCTTAGAAGACCAG
 71    E  R  L  Q  E  N  L  Q  A  Y  R  T  F  Q  G  M  L  T  K  L  L  E  D  Q
              T7                              T4

361   AGAGTACATTTCACCCCAACTGAAGGTGACTTCCATCAGGCAATACATCTTATGCTCCAAGTTTCTGCC
 95    R  V  H  F  T  P  T  E  G  D  F  H  Q  A  I  H  T  L  M  L  Q  V  S  A
                                                                              CB3

433   TTTGCCTACCAGCTAGAGGAGTTAATGGTGCTTCTGGAACAGAAGATCCCTGAAAATGAGGCTGATGGGATG
119    F  A  Y  Q  L  E  E  L  M  V  L  L  E  Q  K  I  P  E  N  E  A  D  G  M
                                 CB1                           T1

505   CCTGCCCACAGTTGGAGATGGTGGTCTCTTTGAGAAGAAGCTATGGGGCTTGAAGGTCCTTCAAGAGCTCTCA
143    P  A  T  V  G  D  G  G  L  F  E  K  K  K  L  W  G  L  K  V  L  Q  E  L  S
                                                                              T2
```

FIG. 1b

```
577   CAGTGGACTGTGAGGTCTATCCATGACCTTCGTGTCATTTCTTCTCATCAGATGGGAATCTCAGCACTTGAG
167    Q  W  T  V  R  S  I  H  D  L  R  V  I  S  S  H  Q  M  G  I  S  A  L  E
                                                                  CB2
649   AGCCATTATGGGGCCAAAGATAAGCAGATGTAGCCATTCGCTCATACCTCTGTCTCCCTTTTGATCTAATG
191    S  H  Y  G  A  K  D  K  Q  M  *

721   AAATATTGATAGTTCCCTGGAGCCTAGTTTTCTCAGCATCAATTTTGAACACTTTAGACCACATGCATTTC
793   ATCAAGTAGGGTTGGCCCACATGAATAGATATACATGGTTATTCTGGCTATGCAAATGTGTGCACC
865   CATTTGGTTTGCATTGGGTGGTATAATAAATGGATGGCCCACCTATCCCTTTCACCATAGTAGTGCTTTAA
937   CCTTCCTGATACTAAGTAACCTTTTCAGGTGTTTAACAGTCTTACAGGCAGAAGAGAAATTGTAACTCGTTT
1009  TGGTTGACTTCTGAAAAGACTGAATAAACAAATTGGAAGTCCTAGACTATCTTCATTCAAACTACCCGAATA
1081  AAAAGAGTATTGTTGTACAGAGAAAAAAAAAAA
```

FIG. 1b (cont.)

| Oligo | Sequence (5' - 3') | Position |
|---|---|---|
| 1 | CCCGGGAATTCGARCARAARATHCC | 468 - 481 |
| 2 | CTGCAGATATCTTYTCRAANARNCC | 525 - 538 |
| 3 | CTGCTAGAGTCGACAAGCTTTTGAAAATGAGGCTGATGGGATG | 482 - 503 |
| 4 | CGTCTAGAGTCGACAAGCTTACCATCTCCAACTGTGGCAGG | 504 - 524 |
| 5 | CGGATCCGAATTCTGCAGTTTTTTTTTTTV | ATAIL |
| 6 | CCGGATCCGCGGCCGCCCCCCCCCCCCCC | GTAIL |
| 7 | CCTCTAGACTCGAGTGCTTGCCACTGGTAC | 243 - 263 |
| 8 | AATATCAACCTTGACTCAGTGGAT | 215 - 238 |
| 9 | CCTCTAGAATGGCTTTCGCAGAGCAAACA | 78 - 98 |
| 10 | CCTCTAGACATCTGCTTATCTTTGGCCCC | 657 - 677 |
| 11 | GARAAYGARGCIGAYGGIATGCC | 483 - 505 |
| 12 | CTCCTCIAGCTGRTAIGCAAAKGCRCTIACCTG | 419 - 451 |

IUPAC CONVENTION FOR AMBIGUOUS CODES:

H = A, C, or T but not G

N = any base A, C, G, or T

K = G or T

I = Inosine

Y = C or T (pyrimidine)

R = A or G (purine)

V = A, C or G but not T

FIG. 1c

|     | PURIFIED CNTF | PREDICTED FROM cDNA |
| --- | --- | --- |
| Asx | 17.1 | 16 |
| Thr | 9.9 | 12 |
| Ser | 9.7 | 14 |
| Glx | 30.5 | 30 |
| Pro | n.d. | 5 |
| Gly | 11.7 | 11 |
| Ala | 14.4 | 14 |
| Val | 11.9 | 11 |
| Met | 7.3 | 9 |
| Ile | 7.7 | 8 |
| Leu | 24.5 | 26 |
| Tyr | 4.3 | 4 |
| Phe | 6.4 | 6 |
| His | 6.2 | 8 |
| Lys | 10.2 | 10 |
| Arg | 11.1 | 11 |
| Cys | n.d. | 1 |
| Trp | n.d. | 4 |

FIG. 1D

```
man   R   L   Q   E   N   L   Q   A   Y   R   T   F   H   V   L   L   A   R   L
      GCGACTCCAAGAGAACCTTCAAGCTTATCGTACCTTCCATGTTTTGTTGGCCAGGCTC
                   *** *      *        *    ***  ** ***     *
rat   GCGACTCCAAGAGAACCTCCAGGCTTACCGTACCTTCCAAGGGATGTTAACCAAGTC
      R   L   Q   E   N   L   Q   A   Y   R   T   F   Q   G   M   L   T   K   L man   L   E   D   Q   Q   V   H   F   T   P   T   E   G   D   F   H   Q   A   I   H
      TTAGAAGACCAGCAGGTGCATTTTACCCCAACCGAAGGTGACTTCCATCAAGCTATACAT
                *** *        *            *        *          *
rat   TTAGAAGACCAGAGAGTACATTTCACCCCAACTGAAGGTGACTTCCATCAGGCAATACAT
      L   E   D   Q   R   V   H   F   T   P   T   E   G   D   F   H   Q   A   I   H man   T   L   L   L   Q   V   A   A   F   A   Y   Q   I   E   E   L   M   I   L   L
      ACCCTTCTTCTCCAAGTCGCTGCTTTTGCCTTTGCCTGCATACCAGATAGAGGAGTTAATGATACTCCTG
                                              *                            *
rat   ACTCTTATGCTCCAAGTTTCTGCCTTTGCCTTTGCCTACCAGTTGGAGGAGTTAATGGTGCTTCTG
      T   L   M   L   Q   V   S   A   F   A   Y   Q   L   E   E   L   M   V   L   L man   E   Y   K   I   P   R   N
      GAATACAAGATCCCCGCAATG
                  *   *
rat   GAACAGAAGATCCCTGAAAATG
      E   Q   K   I   P   E   N
```

FIG. 7

CAATCCCATTAGTAGAGAATGCCAGTGGGTTTAGTCTCTTTGAGAGTCACATCTCTTATTTG GTGCA

GACCAGTATAGACAGAAGTAAACCCAGCTGACTTGTTTCCTGGACAGTTGAGTTAAGGG

M  A  F  T  E  H  S  P  L  T  P  H  H  R  R  D  L  C  S  R  S
ATGGCTTTCACAGAGCATTCACCGCTGACCCCTCACCGTCGGGACCTCTGTAGCCGCTCT

I  W  L  A  R  K  I  R  S  D  L  T  A  L  T  E  S  Y  V  K
ATCTGGCTAGCAAGGAAGATTCGTTCAGACCTGACTGCTCTTACGGAATCCTATGTGAAG

H  Q  G  L  N  K  N  I  N  L  D  S  A  D  G  M  P  V  A  S
CATCAGGGCCTGAACAAGAACATCAACCTGGACTCTGCGGATGGGATGCCAGTGGCAAGC

T  D  Q  W  S  E  L  T  E  A  E  R  L  Q  E  N  L  Q  A  Y
ACTGATCAGTGGAGTGAGCTGACCGAGGCAGAGCGACTCCAAGAGAACCTTCAAGCTTAT

FIG. 8A

```
R  T  F  H  V  L  L  A  R  L  L  E  D  Q  Q  V  H  F  T  P
CGTACCTTCCATGTTTTGTTGGCCAGGCTCTTAGAAGACCAGCAGGTGCATTTTACCCCA

T  E  G  D  F  H  Q  A  I  H  T  L  L  L  Q  V  A  A  F  A
ACCGAAGGTGACTTCCATCAAGCTATACATACCCTTCTTCCAAGTCGCTGCCTTTGCA

Y  Q  I  E  E  L  M  I  L  L  E  Y  K  I  P  R  N  E  A  D
TACCAGATAGAGGAGTTAATGATACTCCTGGAATACAAGATCCCCGCAATGAGGCTGAT

G  M  P  I  N  V  G  D  G  G  L  F  E  K  K  L  W  G  L  K
GGGATGCCTATTAATGTTGGAGATGGTGGTCTCTTTGAGAAGAAGCTGTGGGCCTAAAG

V  L  Q  E  L  S  Q  W  T  V  R  S  I  H  D  L  R  F  I  S
GTGCTGCAGGAGCTTTCACAGTGGACAGTAAGGTCCATCGACCTTCGTTTCATTTCT

S  H  Q  T  G  I  P  A  R  G  S  H  Y  I  A  N  N  K  K  M
TCTCATCAGACTGGGATCCCAGCACGTGGGAGCCATTATATTGCTAACAACAAGAAAATG

TAGCAGTTAGTCCCTTCCTCTCTCCTTACTTTCTCCTTCTAATGGAATATGCGTAGTT
```

FIG. 8A (cont.)

```
        Gap Weight:    3.000         Average Match:    0.540
     Length Weight:    0.100         Average Mismatch: -0.396

Quality:   264.5           Length:           200
            Ratio:     1.323         Gaps:               0
Percent Similarity: 89.500           Percent Identity: 84.000

New.Pep x Rcntf.Pep       October 13, 1989   07:57  ..

human   1 MAFTEHSPLTPHRRDLCSRSIWLARKIRSDLTALTESYVKHQGLNKNINL  50
          ||| |:.|| ||||||||||||||||||||||||| ||:|||||||||||
rat     1 MAFAEQTPLTLHRRDLCSRSIWLARKIRSDLTALMESYVKHQGLNKNINL  50 human  51 DSADGMPVASTDQWSELTEAERLQENLQAYRTFHVLLARLLEDQQVHFTP 100
          ||:||:|||||| |||||||||||||||||||:|:|:||||||| |||||
rat    51 DSVDGVPVASTDRWSEMTEAERLQENLQAYRTFQGMLTKLLEDQRVHFTP 100 human 101 TEGDFHQAIHTLLLQVAAFAYQIEELMILLEYKIPRNEADGMPINVGDGG 150
          ||||||||||||:|||||||||| |||||:||||| |||||||| |||||
rat   101 TEGDFHQAIHTLMLQVSAFAYQLEELMVLLEQKIPENEADGMPATVGDGG 150 human 151 LFEKKLWGLKVLQELSQWTVRSIHDLRFISSHQTGIPARGSHYIANNKKM 200
          ||||||||||||||||||||||||||||:||:  :.| .:|||||.|||
rat   151 LFEKKLWGLKVLQELSQWTVRSIHDLRVISSHQMGISALESHYGAKDKQM 200
```

FIG. 8B

```
Gap Weight:     5.000           Average Match:      1.000
Length Weight:  0.300           Average Mismatch:   0.000

Quality:  606.4               Length:  1146
        Ratio:    0.775                 Gaps:     2
Percent Similarity: 84.175     Percent Identity: 84.175

Human.Seq x Cntf.Seq    October 24, 1989  07:05  ..

human    1 GTGCACAATCCCATTAGTAGAGAATGCCAGTGGGTTTAGTCTTTGAGAGT   50
                                                  |||
rat      1 .................................................AGT    3 human   51 CACATCTCTTATTTGGACCAGTATAGACAGAAGTAAACCCAGCTGACTTG  100
           ||||| ||||||||||||||||| ||  ||| ||||  |||| ||||||
rat      4 CACATTTCTTATTTGGACTAGTGAAGACAGAAGCAAA.CCAGCTCACTTG   52 human  101 TTTCCTGGGACAGTTGAGTTAAGGGATGGCTTTCACAGAGCATTCACCGC  150
           | ||||||||||||| ||||| ||||||||||||  |||| |||| ||
rat     53 TGTCCTGGGACAGTTGATTTAGGGGATGGCTTTCGCAGAGCAAACACCTC  102 human  151 TGACCCCTCACCGTCGGGACCTCTGTAGCCGTCTATCTGGCTAGCAAGG  200
           ||||||  |||||  ||||||||||||||| || ||||||||||||||
rat    103 TGACCCTTCACCGCCGGGACCTCTGTAGCCGTTCTATCTGGCTAGCAAGG  152

FIG. 8C
```

```
human  201  AAGATTCGTTCAGACCTGACTGCTCTTACGGAATCCTATGTGAAGCATCA  250
            ||||||||||||||||||||||||||||||||| ||||| |||| ||||
rat    153  AAGATTCGTTCAGACCTGACTGCTCTTATGGAATCTTATGTAAAACATCA  202 human  251  GGGCCTGAACAAGAACATCAACCTGGACTCTGCGGATGGGATGCCAGTGG  300
            ||||||||| |||| || ||  ||||||||||| ||||| ||||||||| 
rat    203  GGGCCTGAATAAAAAATATCAACCTTGACTCAGTGATGGTGTACCAGTGG  252 human  301  CAAGCACTGATCAGTGGAGTGAGTGACCGAGGCAGAGCGACTCCAAGAG   350
            ||||||||||||||||||||||||||| |||||||||||||||||||||
rat    253  CAAGCACTGATCGTTGGAGTGAGTGAGATGACTGAGGCAGAGCGACTCCAAGAG  302 human  351  AACCTTCAAGCTTATCGTACCTTCCATGTTTTGTTGGCCAGGCTCTTAGA  400
            |||| |||||||  ||| ||||| ||| ||   |||  ||||  |||||
rat    303  AACCTCCAGGCTTACCGTACCTTCCAAGGATGTTAACCAAGCTCTTAGA   352 human  401  AGACCAGCAGGTGCATTTTACCCCAACCGAAGGTGACTTCCATCAAGCTA  450
            ||||||| |||| ||||| ||||| |||||| |||||||||||||| ||
rat    353  AGACCAGAGAGTACATTTCACCCCAACTGAAGGTGACTTCCATCAGGCAA  402 human  451  TACATACCCTTCTTCTCCAAGTCGCTGCCTTTGCATACCAGATAGAGGAG  500
            ||||| |||||||||||||||  |||||||||||||  ||| |||||||
rat    403  TACATACTCTTCTTCTCCAAGTTTCTGCCTTTGCCTACCAGCTAGAGGAG  452
```

FIG. 8C (cont.)

```
human  501  TTAATGATACTCCTGGAATACAAGATCCCCCGCAATGAGGCTGATGGGAT  550
              ||||| |||| || ||||| ||||||||||  ||||||||||||||||||
rat    453  TTAATGGTTGCTTCTGGAACAGAAGATCCCTGAAAATGAGGCTGATGGGAT  502 human  551  GCCTATTAATGTTGGAGATGGTGGTCTCTTTGAGAAGAAGCTGTGGGGCC  600
              |||| |||| |||||||||||||| |||||||||||||||| ||||||
rat    503  GCCTGCCACAGTTGGAGATGGTGGTCTCTTTGAGAAGAAGCTATGGGGCT  552 human  601  TAAAGGTGCTGCTGCAGGAGCTTTCACAGTGGACAGTAAGGTCCATCCATGAC  650
              |  ||||||||  |||| ||||||||||| |||||||||| |||||||||
rat    553  TGAAGGTCCTTCAAGAGCTCTCACAGTGGACTGTGAGGTCTATCCATGAC  602 human  651  CTTCGTTTCATTTCTTCTCATCAGACTGGGATCCCAGCACGTGGGAGCCA  700
              |||||||||||| |||||||||||| |||||||||||||   ||||||
rat    603  CTTCGTGTCATTTCTTCTTCATCAGATGGGAATCTCAGACTTGAGAGCCA  652 human  701  TTATATTGCTAACAACAAGAAAATGTAGCAGTTAGTCCCCTTCTCTTCC  750
             ||||  |||||  |||| |||| |||||||||| |  |    ||||
rat    653  TTATGGGCCAAAGATAAGCAGATGTAGCCATTCG.CTCATACCCTCGTC  701 human  751  TTACTTTCTCTTCTAATGGAATATGCGTAGTT..............    782
             |  ||||| ||||| |||| ||| |  ||||
rat    702  TCCCTTTTTGATCTAATGAAATATTGATAGTTCCCTGGAGCCTAGTTTTC  751
```

FIG. 8C (cont.)

FIG. 8d (cont.)

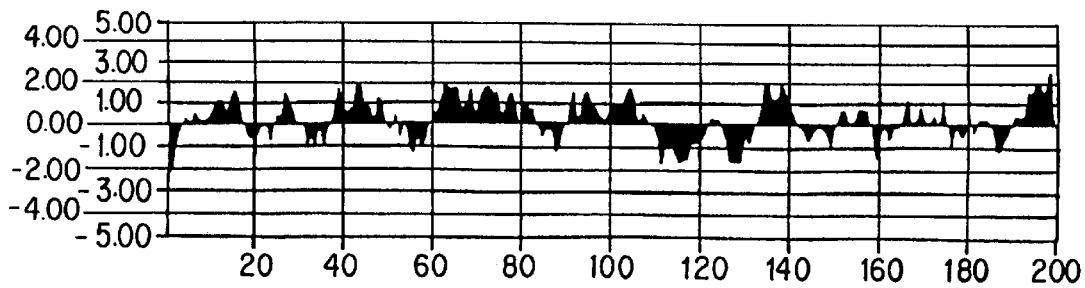
HYDROPHILICITY
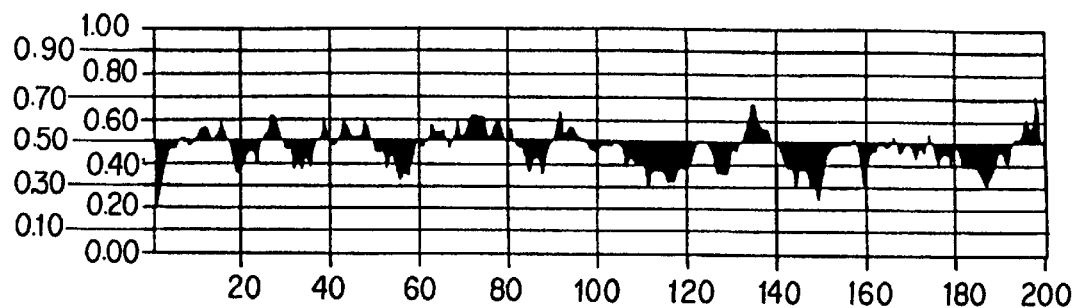
SURFACE PROBABILITY
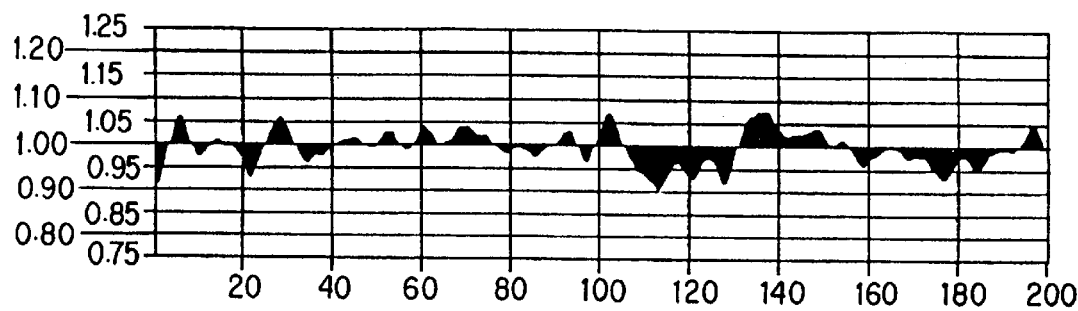
FLEXIBILITY
FIG. 15A ANTIGENIC INDEX
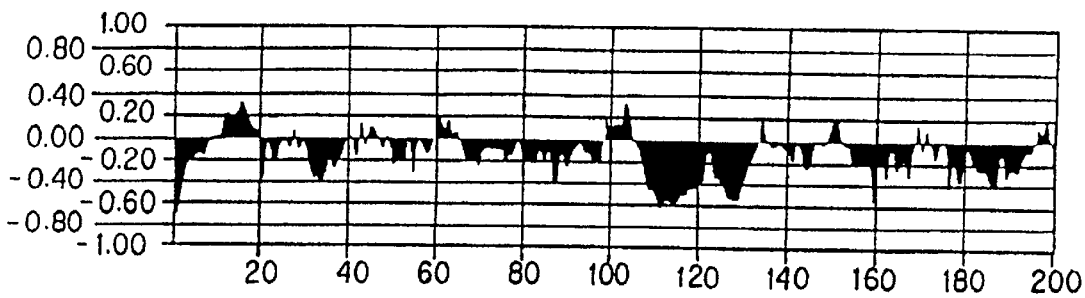
AMPHIPHILIC HELIX
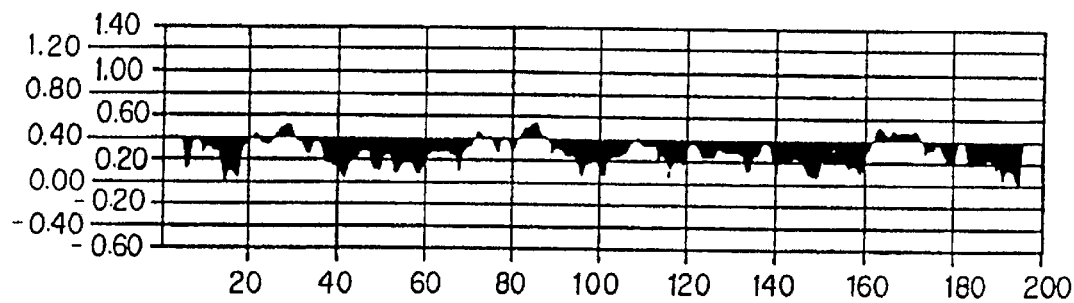
AMPHIPHILIC SHEET
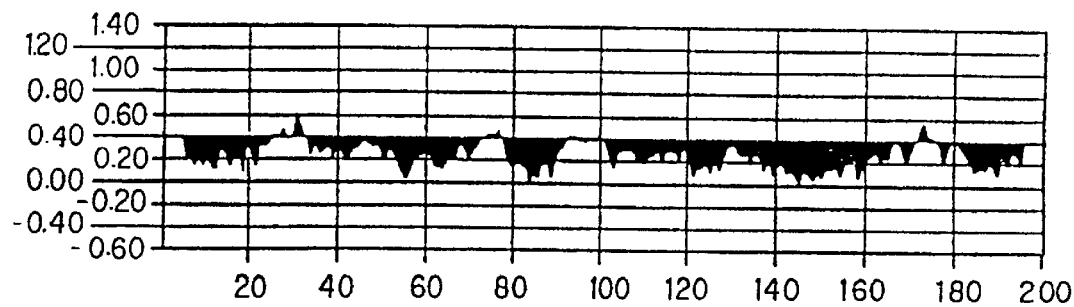
SECONDARY STRUCTURE
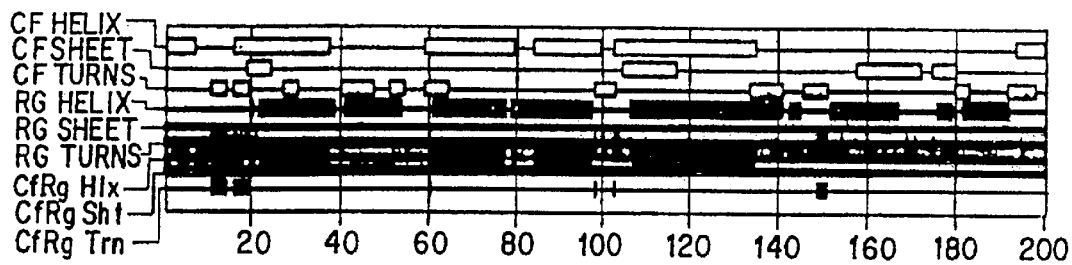
FIG. 15A (cont.)

HYDROPHILICITY
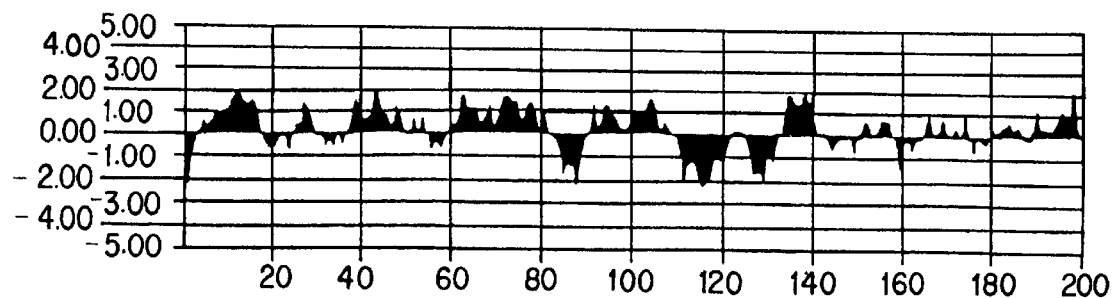
SURFACE PROBABILITY
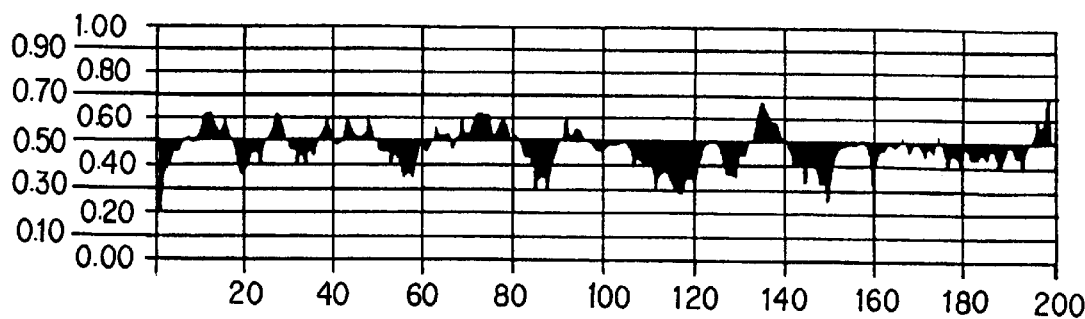
FLEXIBILITY
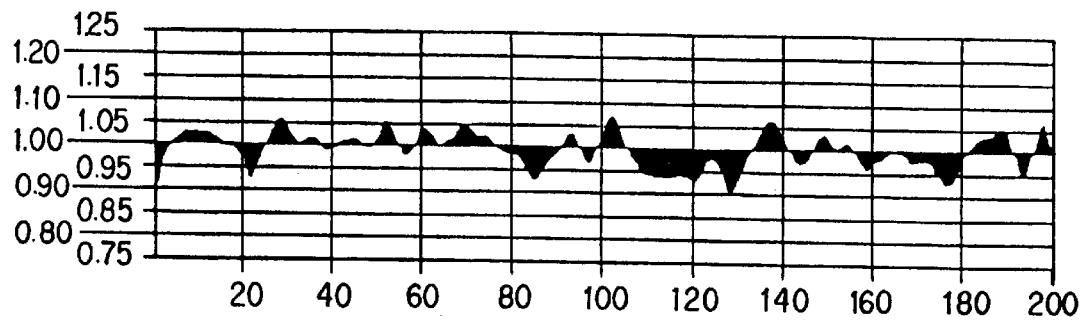
FIG. 15B ANTIGENIC INDEX
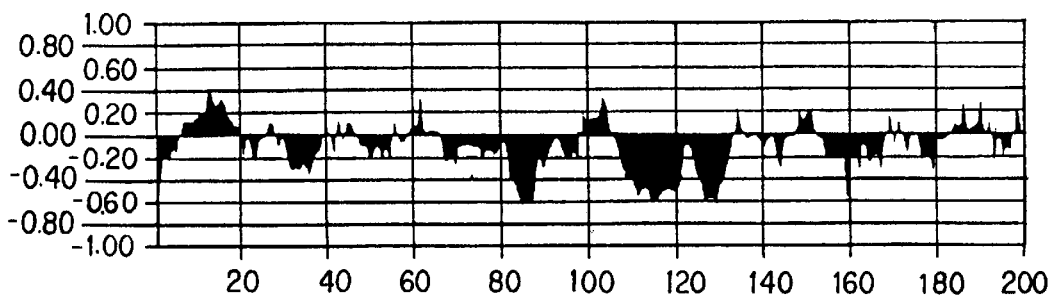
AMPHIPHILIC HELIX
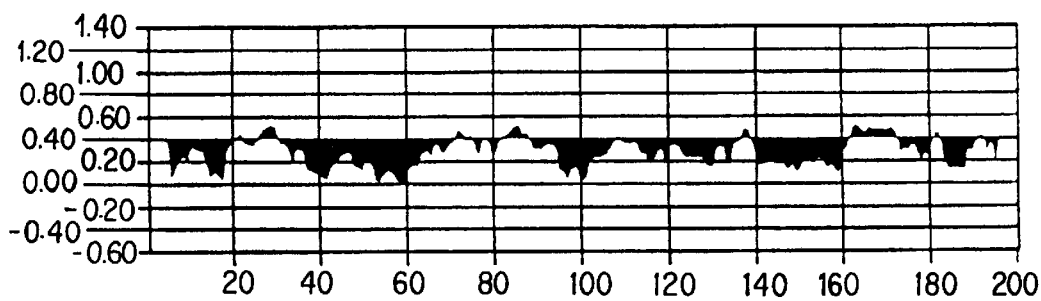
AMPHIPHILIC SHEET
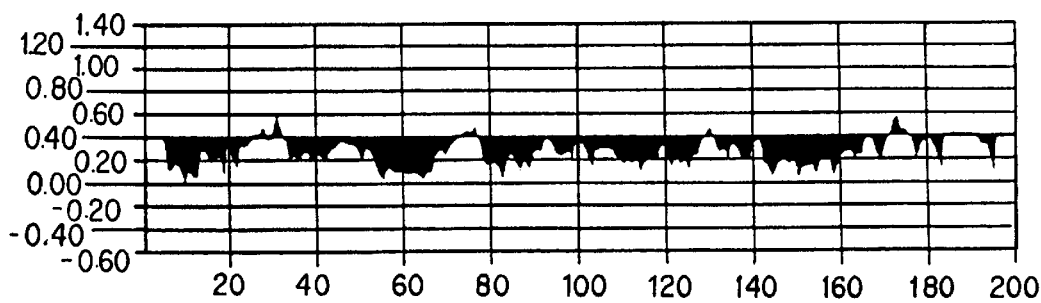
SECONDARY STRUCTURE
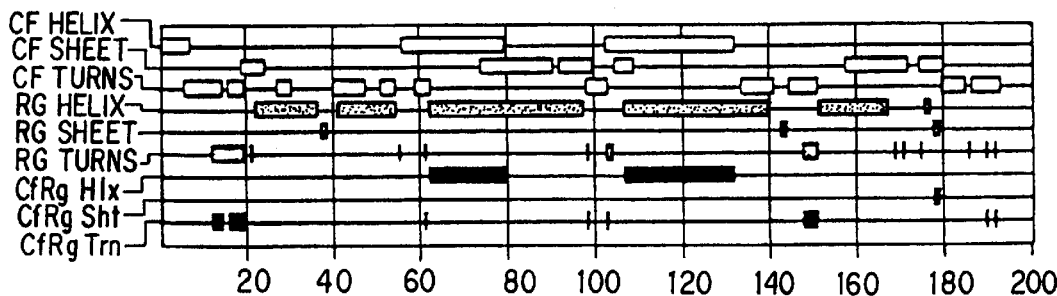
FIG. 15B (cont.)

```
              10              20              30              40              50              60
              .               .               .               .               .               .
                                              MetAlaPheThrGluHisSerProLeuThrPro
TGTTTCCTGGGACAGTTGAGTTAAGGGATGGCTTTCACAGAGCATTCACCGCTGACCCCT
                                              ─────────────────────────────────>
                                                         CNTF.23

HisArgAspLeuCysSerArgSerIleTrpLeuAlaArgLysIleArgSerAspLeu
CACCGTCGGGACCCTCTGTAGCCGCTCTATCTGGCTAGCAAGGAAGATTCGTTCAGACCTG

[GTAAGTTGCCTATT....TGTATCCCTCGGCCAG]
                ▼▼
ThrAlaLeuThrGluSerTyrValLysHisGlnGlyLeuAsnLysAsnIleAsnLeuAsp
ACTGCTCTTACGGAATCCTATGTGAAGCATCAGGGCCTGAACAAGAACATCAACCTGGAC
<─────────────────
      CNTF.21
      ────────────────────────────>
             CNTF.22

SerAlaAspGlyMetProValAlaSerThrAspGlnTrpSerGluLeuThrGluAlaGlu
TCTGCGGATGGGATGCCAGTGGCAAGCACTGATCAGTGGAGTGAGCTGACCGAGGCAGAG
                            **************──────*─────────>
                                       CNTF.11
```

FIG. 17

```
ArgLeuGlnGluAsnLeuGlnAlaTyrArgThrPheHisValLeuLeuAlaArgLeuLeu
CGACTCCAAGAGAACCTTCAAGCTTATCGTACCTTCCATGTTTTGTTGGCCAGGCTCTTA

GluAspGlnValHisPheThrProThrGluGlyAspPheHisGlnAlaIleHisThr
GAAGACCAGCAGGTGCATTTCACCCAACCGAAGGTGACTTCCATCAAGCTATACATACC

LeuLeuLeuGlnValAlaAlaAlaPheAlaTyrGlnIleGluLeuLeuMetIleLeuLeuGlu
CTTCTTCTCCAAGTGCTGCTGCCTTTGCATACCAGATAGAGAGTTAATGATACTCCTGAA
                                         **********************
                                         <──────────
                                            CNTF.10

TyrLysIleProArgAsnGluAlaAspGlyMetProIleAsnValGlyAspGlyGlyLeu
TACAAGATCCCCCGCAATGAGGCTGATGGGATGCCTATTAATGTTGGAGATGGTGGTCTC
***************

PheGluLysLysLeuTrpGlyLeuLysValLeuGlnGluLeuSerGlnTrpThrValArg
TTTGAGAAGAAGCTGTGGGGGCCTAAAGGTGCTGCAGGAGCTTTCACAGTGGACAGTAAGG

SerIleHisAspLeuArgPheIleSerSerHisGlnAspLeuLeuArgGlyIleProAlaArgGlySer
TCCATCCATGACCTTCGTTTCATTTCTTCTCATCAGACTGGGATCCCAGCACGTGGGAGC

HisTyrIleAlaAsnAsnLysLysMet
CATTATATTGCTAACAACAAGAAAATGTAGCAGTTAGTCCCTTCTCTCTTCCTTACTTTC
                             *  ***  ─── *
                             <──────────
                                CNTF.24
```

FIG. 17 (cont.)

FIG. 21A 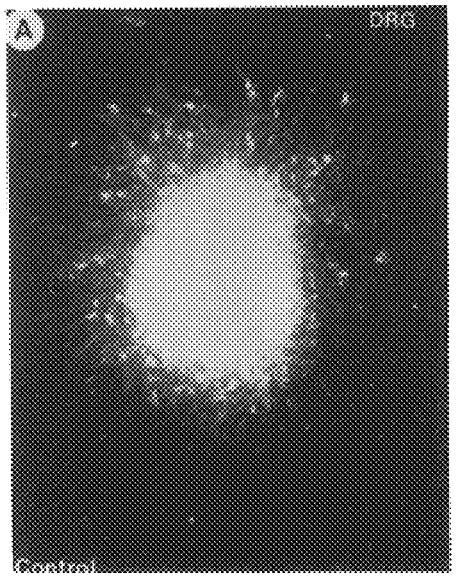 FIG. 21B 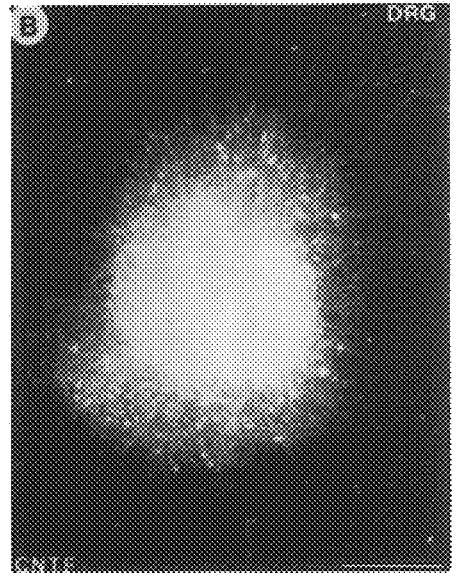
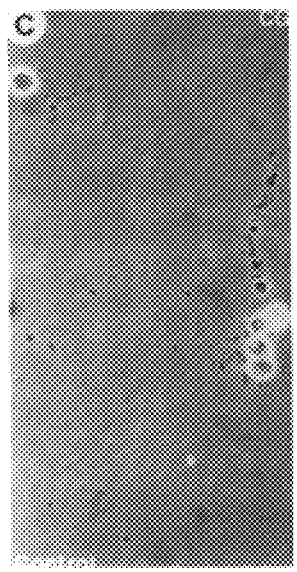 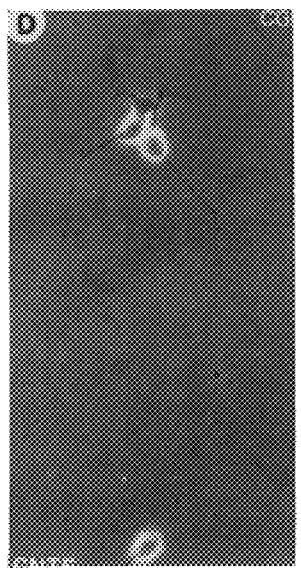 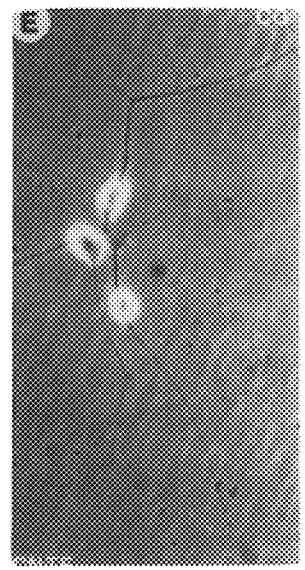
FIG. 21C   FIG. 21D   FIG. 21E

A.

```
               10         20         30         40         50         60         70         80         90        100
hu    MAFTEHSPLTPHRRDLCSRSIWLARKIRSDLTALTESYVKHQGLNKNINLDSADGMPVASTDQWSELTEAERLQENLQAYRTFHVLLARLLEDQQVHFTP
rt    ...A.QT...L.....................M............................V...R..M.................QGM.TK....R....
rb    ...M...A.....E...T.................................V..V............V..M........................IM.....
```

```
              110        120        130        140        150        160        170        180        190        200  pRPH
hu    TEGDFHQAIHTLLLQVAAFAYQIEELMILLEYKIPRNEADGMPINVGDGGLFEKKLWGLKVLQELSQWTVRSIHDLRFISSHQTGIPARGSHYIANNKKM   33
rt    .......M..S......L...V...Q...E......AT.......................V....M..S.LE...G.KD.C.               110
rb    A....HF................V...CN..PKD...T.V-I.GD...................H.....................D.E.
```

B.

```
hu    ............A...........................................................................................    108
hu    ............S...........................................................................................    109
hu    ................................................................mqdstsdlipapplskvplqqnfqddqfqqkwyvgg..     59
hu    ..........................................................................................................  112
rt    .......................................................................................rreagwpspl          12
rt    ........................................................................................N...........        65
hu    ..........................................................................................................   82
```

FIG.22

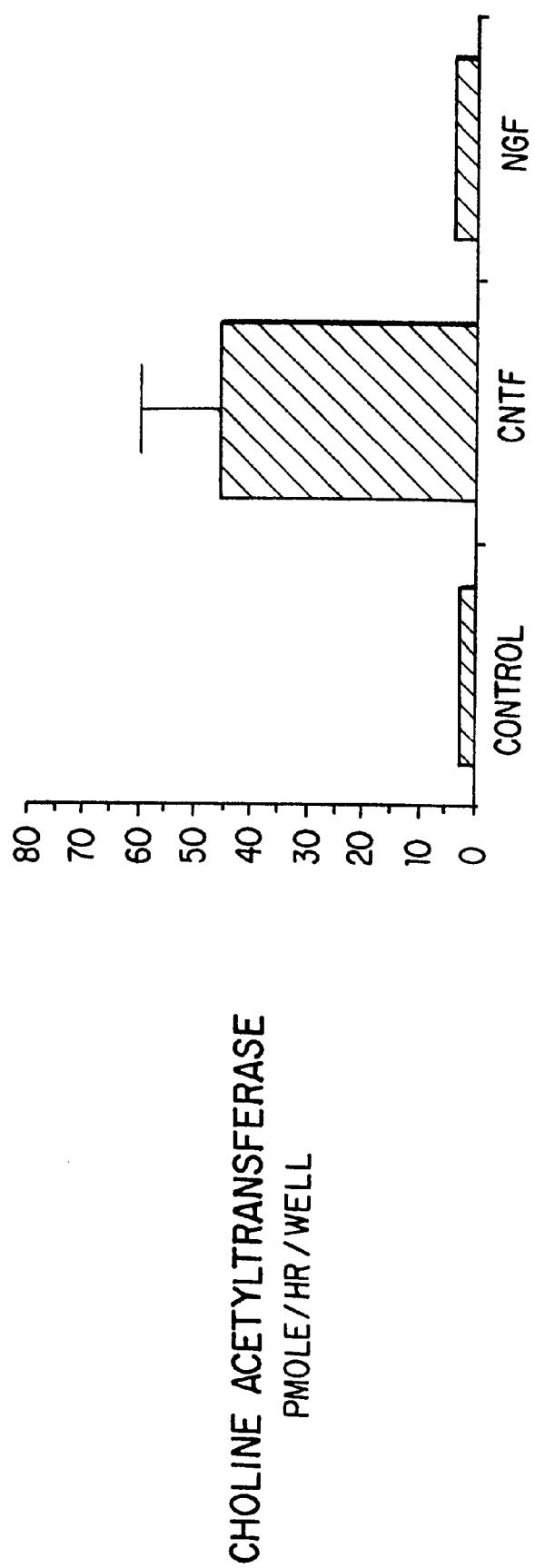

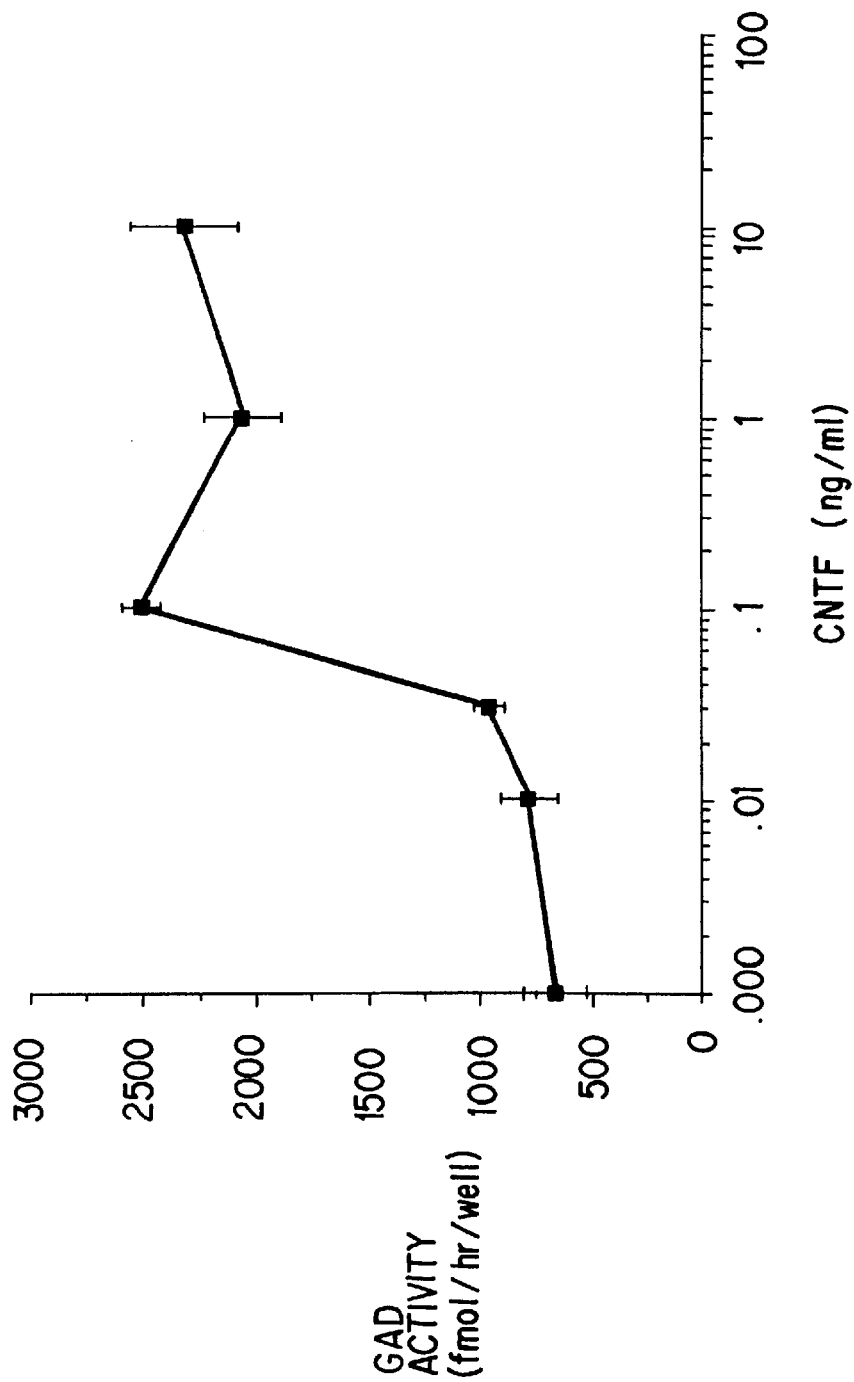

FIG. 42A
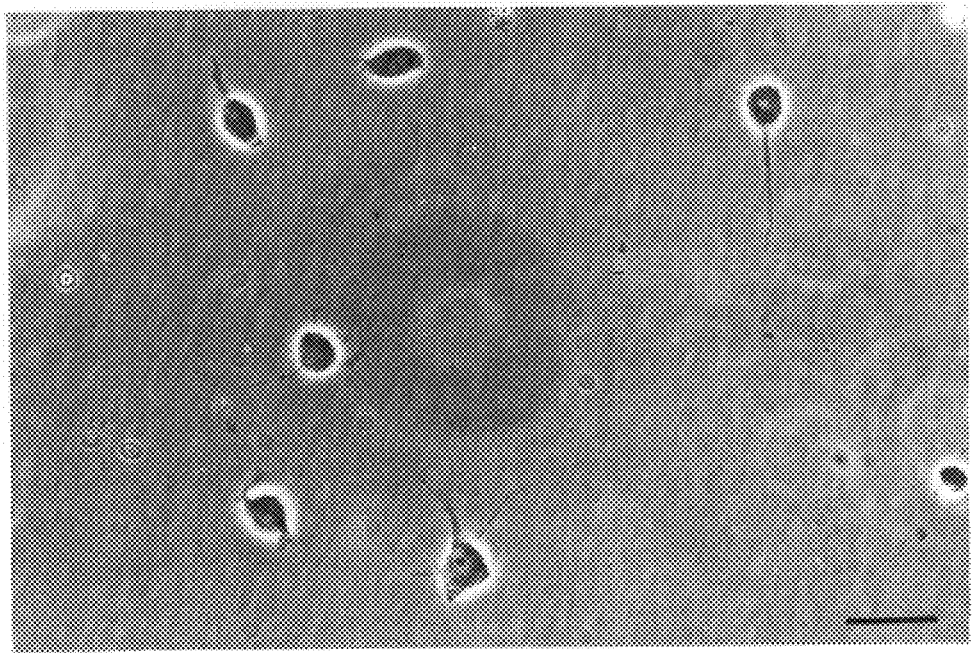
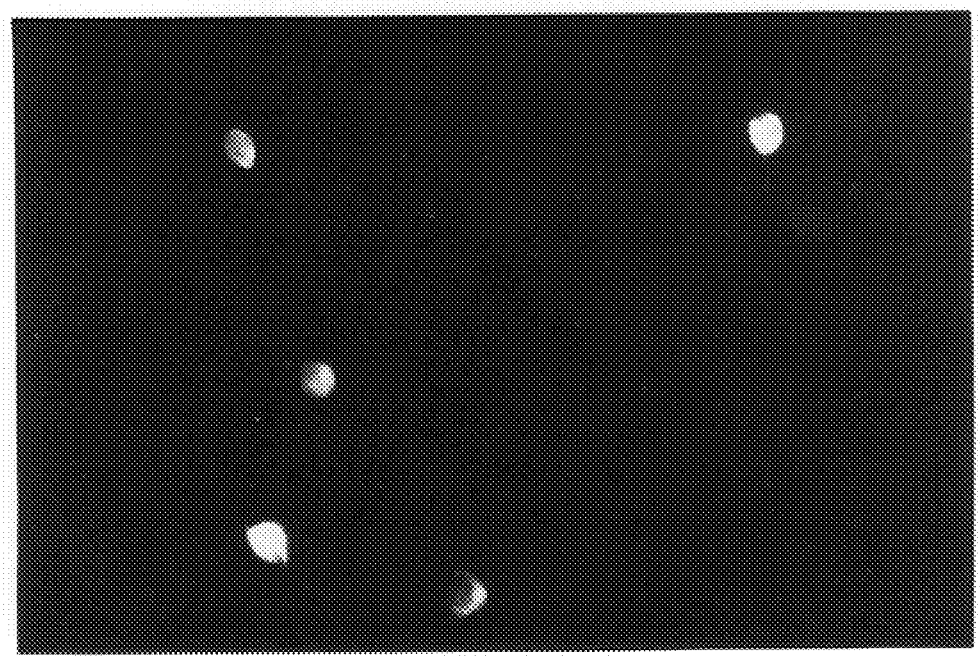
FIG. 42B

Fig. 46

```
    M  A  F  A  E  Q  T  P  L  T  L  H  R  R  D  L  C  S  R  S
    ATGGCTTTCGCAGAGCAAACACCTCTGACCCTTCACCGCCGGGACCTCTGTAGCCGTTCT    RAT

\/
    I  W  L  A  R  K  I  R  S  D  L  T  A  L  M  E  S  Y  V  K
    ATCTGGCTAGCAAGGAAGATTCGTTCAGACCTGACTGCTCTTATGGAATCTTATGTAAAA    RAT
                       ≠       ≠       ≠         ≠         ≠
                       CGTTCAgAcCTGAcTCCTCTTACGGAATCCTAT...
                                                     ...gTGAAG      HUMAN
                       R  S  D  L  T  P  L  T  E  S  Y  V  K
                                                      *     *

H  Q  G  L  N  K  N  I  N  L  D  S  V  D  G  V  P  V  A  S     RAT
    CATCAGGGCCTGAATAAAAATATCAACCTTGACTCAGTGGATGGTGTACCAGTGGCAAGC
          ≠    ≠    ≠    ≠
    CATCAGGgCCTGAACAAGAACAA                              GTGGCAAGC  HUMAN
    H  Q  G  L  N  K  N                                  V  A  S

T  D  R  W  S  E  M  T  E  A  E  R  L  Q  E  N  L  Q  A  Y     RAT
    AcTgatCGTTGGAGTGAGATGACTGAGGCAGAGCGACTCCAAGAGAACCTCCAGGCTTAC
      ≠≠      ≠        ≠                                ≠    ≠
    AcTGATCAGTcGAGTGAGCTGACCGAGGcAGAGCGACTCCAAGAGAACCTTCAAGCTTAT    HUMAN
                                 GCGACTCCAAGAGAACCTTCAAGCTTAT
    T  D  Q  W  S  E  L  T  E  A  E  R  L  Q  E  N  L  Q  A  Y
                      *           *

R  T  F  Q  G  M  L  T  K  L  L  E  D  Q  R  V  H  F  T  P     RAT
    CGTACCTTCCAAGGGATGTTAACCAAGCTCTTAGAAGACCAGAGAGTACATTTCACCCCA
         ≠   ≠≠     ≠      ≠                 ≠≠≠    ≠       ≠
    CGTACCTTCCATGTTTTGTT                                            HUMAN
    CGTACCTTCCATGTTTTGTTGGCCAGGCTCTTAGAAGACCAGCAGGTGCATTTTACCCCA
    R  T  F  H  V  L  L  A  R  L  L  E  D  Q  Q  V  H  F  T  P
              *  *  *  *  *

T  E  G  D  F  H  Q  A  I  H  T  L  M  L  Q  V  S  A  F  A     RAT
    ACTGAAGGTGACTTCCATCAGGCAATACATACTCTTATGCTCCAAGTTTCTGCCTTTGCC
       ≠          ≠  ≠       ≠     ≠  ≠    ≠≠       ≠        ≠
    ACCGAAGGTGACTTCCATCAAGCTATACATACCCTTCTTCTCCAAGTCGCTGCCTTTGCA    HUMAN
    T  E  G  D  F  H  Q  A  I  H  T  L  L  L  Q  V  A  A  F  A
                                         *     *
```

DNA ENCODING HUMAN CILIARY NEUROTROPHIC FACTOR AND METHOD FOR PRODUCING THE PROTEIN ENCODED THEREBY

This application is a divisional application of application Ser. No. 09/570,651, filed Aug. 20. 1990, now abandoned which is a continuation-in-part of application Ser. No. 07/429,517, filed Oct. 31, 1989, now abandoned which is a continuation-in-part of application Ser. No. 07/408,172, filed Sep. 15, 1989, now abandoned which are incorporated by reference herein in their entireties.

1. Introduction
2. Background of the Invention
   2.1. Biology of Neurotrophic Factors
   2.2. Ciliary Neurotrophic Factor
   2.3. Functional Properties of Ciliary Neurotrophic Factor
3. Summary of the Invention
   3.1. Abbreviations
4. Description of the Figures
5. Detailed Description of the Invention
   5.1. Purification of CNTF
   5.2. CNTF Bioassays
   5.3. Sequencing of CNTF Protein
   5.4. Cloning of CNTF-Encoding DNA
   5.5. Expression of a CNTF Gene
      5.5.1. Identification and Purification of the Expressed Gene Product
   5.6. CNTF Genes and Proteins
   5.7. Generation of Anti-CNTF Antibodies
   5.8. Utility of the Invention
      5.8.1. Diagnostic Applications
      5.8.2. Therapeutic Applications
      5.8.3. Pharmaceutical compositions
      5.8.4. Molecular Probes of the Invention May Be Used to Identify Novel CNTF-Homologous Molecules
6. Example: Molecular Cloning, Expression and Regional Distribution of Rat Ciliary Neurotrophic Factor (CNTF)
   6.1. Materials and Methods
      6.1.1. Purification and Cleavage of CNTF
      6.1.2. Generation of cDNA CNTF Clones
      6.1.3. Northern Blot
      6.1.4. Expression Of Recombinant CNTF
   6.2. Results
      6.2.1. Determination of CNTF Amino Acid Sequence
      6.2.2. Generation of CNTF cDNA Clones and Sequence Analysis
      6.2.3. Expression of Recombinant CNTF
      6.2.4. Northern Blot Analysis
   6.3. Discussion
7. Example: Expression of CNTF In *Escherichia Coli*
   7.1. Materials and Methods
      7.1.1 Construction of a CNTF Expression Vector
      7.1.2 Identification of Bacteria Containing the CNTF Expression Vector
   7.2. Results and Discussion
8. Example: Cloning of the Human CNTF Gene
   8.1. Materials and Methods
      8.1.1. DNA, Plasmid and Phage Vectors
      8.1.2. Polymerase Chain Reaction
   8.2. Results and Discussion
      8.2.1. Evidence for the Existence of a Human CNTF Gene
      8.2.2. Cloning of a Fragment of the Human CNTF Gene Amplified by PCR
      8.2.3. Cloning of the Human CNTF Gene from a Genomic Library
9. Example: Utility of CNTF-Derived Peptide Fragments
   9.1. Materials and Methods
      9.1.1. Synthesis of Peptides
      9.1.2. Cell Culture
      9.1.3. Immunization Protocol
   9.2. Results and Discussion
      9.2.1. Ability of Antibodies Directed Toward a Synthetic Peptide to Neutralize CNTF Activity
      9.2.2. Neurotrophic Activity of a Synthetic CNTF Peptide Fragment
      9.2.3. Ability Of Antibodies Directed Toward A Synthetic Peptide To Identify CNTF Containing
10. Example: Ciliary Neurotrophic Factor Promotes Survival of Spinal Cord Neurons
    10.1. Materials and Methods
       10.1.1. Experimental Animals
       10.1.2. Tissue Culture Techniques
    10.2. Results and Discussion
       10.2.1. Effects of Ciliary Neurotrophic Factor (CNTF) on Mediodorsal (MD) Spinal Cord Neurons
       10.2.2. Effects of CNTF on Ventral Spinal Cord Neurons
11. Example: Purified Rat Sciatic Nerve CNTF Prevents Lesion-Induced Cell Death of Motorneurons in the Facial Nerve (VIIth Cranial Nerve) of the Newborn Rat
    11.1. Materials And Methods
    11.2. Results And Discussion
12. Example: High Level Expression And Purification Of Recombinant Human And Rat Ciliary Neurotrophic Factors In *Escherichia Coli*
    12.1. Materials And Methods
       12.1.1. Bacterial Strains And Plasmids
          12.1.1.1. Rat CNTF Vectors
             12.1.1.1.1. pRPN11
             12.1.1.1.2. pRPN12
             12.1.1.3. pRPN37
             12.1.1.1.4. pRPN38
          12.1.1.2. Human CNTR Vectors
             12.1.1.2.1. pRPN32
             12.1.1.2.2.pRPN33, PRPN39 pRPN40
       12.1.2. Induction Of Protein Synthesis
       12.1.3. "RAPID" Protein Extraction
       12.1.4. Chromatography
       12.1.5. Peptide Analysis
          12.1.5.1. Rat CNTF
          12.1.5.2. Human CNTF
       12.1.6. Biological Activity
       12.1.7. Other Methods
    12.2. Results And Discussion
       12.2.1. Expression Of Rat CNTF
          12.2.1.1. Effect Of Copy Number
          12.2.1.2. Effect Of Antibiotic Resistance
       12.2.2. Expression Of Human CNTF
       12.2.3. Purification Of Rat And Human CNTF
          12.2.3.1. Yield
          12.2.3.2. Characterization
       12.2.4. Biological Activity
13. Example: Effects Of Modified And Truncated Ciliary Neurotrophic Factor Protein On Biological Activity
    13.1. Materials And Methods
       13.1.1. Construction Of Parental Expression Vectors
       13.1.2. Construction Of Modified Human Ciliary Neurotrophic Factor Vectors
       13.1.3. Construction Of Modified Rat Ciliary Neurotrophic Factor Vectors 13.1.4. Biological Assay Of Ciliary Neurotrophic Factor Activity
13.2. Results And Discussion
14. Example: Additional Effects Of CNTF On Ventral Spinal Cord Neurons
    14.1. Materials And Methods
        14.1.1. Experimental Animals
        14.1.2. Tissue Culture Techniques
        14.1.3. Neurofilament (NF) Assay
        14.1.4. Choline Acetytransfereaese (CAT) Assay
        14.1.5. Histochemical Staining For Acetylcholinesterase (AchE)
        14.1.6. Fractionation Of Ventral Horn Cells by Metrizamide Density Gradient
    14.2. Results And Discussion
        14.2.1. General Morphologies Of Cultures
        14.2.2. Effects Of CNTF On Neurofilament (NF) Levels
        14.2.3. Effects Of CNTF On Survival Of AChE-Containing Neurons
        14.2.4. Effects Of CNTF In Cat Activity
        14.2.5. Delayed Addition Experiment
        14.2.6. Effects Of CNTF On Ventral Horn Cultures In The Absence Of Glia
        14.2.7. Effects Of CNTF On Metrizamide Gradient-Purified Motorneurons
15. Example: Effect Of Ciliary Neurotrophic Factor On Hippocampal Cultures
    15.1. Materials And Methods
        15.1.1. Hippocampal Cell Cultures
        15.1.2. Assay For GAD Enzyme Activity
        15.1.3. Measurement Of Neurofilament Protein
        15.1.4. Measurement Of High Affinity GABA Uptake
        15.1.5. Immunohistochemical Staining For GAD Or GABA
        15.1.6. Immunohistochemical Staining For Neuron-Specific Enolase (NSE)
        15.1.7. Histochemical Staining For Calbindin
        15.1.8. Histochemical Staining For Acetylcholinesterase
        15.1.9. Ciliary Neurotrophic Factor
    15.2. Results
    15.3. Discussion
16. Example: Novel Monoclonal Antibodies To Ciliary Neurotrophic Factor And A Two-Antibody Sandwich Assay For Human Ciliary Neurotrophic Factor
    16.1. Materials And Methods
        16.1.1. Generation Of Monoclonal Antibodies To Ciliary Neurotrophic Factor
            16.1.1.1. Immunization Protocol
            16.1.1.2. Hybridoma Formations
            16.1.1.3. Screening Of Hybridomas For CNTF Reactivity
        16.1.2. Preparation Of Variants Of Human CNTF
        16.1.3. Methodology For Two-Site Immunoassay
    16.2. Result And Discussion
17. Ciliary Neurotrophic Factor Promotes Survival Of Spinal Motorneurons In Culture
    17.1 Material And Methods
        17.1.1. Tissue Culture Techniques
        17.1.2. Retrograde Labeling Of Motorneurons And Estimation Of The Purity Of The Culture Of Motorneurons
    17.2. Results And Discussion
        17.2.1. Effect of Ciliary Neurotrophic Factor (CNTF) On Chick Embryonic Spinal Motorneurons In Culture
        17.2.2. Survival Effects of Specific Neurotrophic Molecules and Cytokines
        17.2.3. Combination of CNTF, Basic FGF and IGF-I
18. Deposit of Microorganism

1. INTRODUCTION

The present invention relates to recombinant DNA molecules encoding ciliary neurotrophic factor (CNTF), and to peptides and proteins derived therefrom. The CNTF and related molecules produced according to the invention may be used to treat a variety of neurological disorders.

2. BACKGROUND OF THE INVENTION

2.1. Biology of Neurotrophic Factors

A number of factors have been identified which influence growth and development in the nervous system. It is believed that these factors may play an important role in sustaining the survival of neuronal populations in the mature, as well as the immature nervous system.

During the normal development of many neuronal populations, there is a defined period of cell death in which many members of the original population die (Hamburger and Levi-Montalcini, 1949, J. Exp. Zool. III:457–501; Hamburger, 1958, Amer. J. Anat. 102:365:410; Hamburger, 1975, J. Comp. Neurol. 160:535–546; Cowan and Wenger, 1968, Z. Exp. Zool., 168:105–124; Rogers and Cowan, 1973, J. Comp. Neurol. 147:291–320; Clarke and Cowan, 1976, J. Comp. Neurol. 167:143–164; Clarke et al., 1976, J. Comp. Neurol. 167:125–142; Hollyday and Hamburger, 1976, J. Comp. Neurol. 170:311–320; Varon and Bunge, 1978, Annu. Rev. Neurosci. 1:327–362; Cowan et al., 1984, Science 225:1258–1265). Neuronal survival has been shown to be proportional to the size of the territory innervated; the smaller the target area of a given neuronal population, the fewer the number of neurons which will survive the period of cell death. It has been suggested that the amount of neurotrophic factor present in the target area may be related to neuronal survival.

Nerve growth factor (NGF) is by far the most fully characterized of these neurotrophic molecules and has been shown, both in vitro and in vivo, to be essential for the survival of sympathetic and neural crest-derived sensory neurons during early development of both chick and rat (Levi-Montalcini and Angeletti, 1963, Develop. Biol. 7:653–659; Levi-Montalcini et al., 1968, Physiol. Rev. 48:524–569). Injections of purified NGF into the developing chick embryo have been found to cause massive hyperplasia and hypertrophy of spinal sensory neurons and sympathetic neurons (Levi-Montalcini and Booker, 1960, Proc. Natl. Acad. Sci. U.S.A. 46:373–384; Hamburger et al., 1981, J. Neurosci. 1:60–71). Conversely, removal or sequestration of endogenous NGF by daily injection of anti-NGF antibodies into neonatal rats has been associated with virtual destruction of the sympathetic nervous system (Levi-Montalcini and Booker, 1960, Proc. Natl. Acad. Sci. U.S.A. 46:384–391; Levi-Montalcini and Angeletti, 1966, Pharmacol. Rev. 18:619–628). Exposure to NGF antibodies even earlier in development either by antibody injections in utero or by passive transplacental transfer of maternal antibodies has been shown to result in a substantial loss of neural crest-derived sensory neurons such as spinal and dorsomedial trigeminal sensory neurons (Goedert et al., 1984, Proc. Natl. Acad. Sci. U.S.A. 81:1580–1584; Gorin and Johnson, 1979, Proc. Natl. Acad. Sci. U.S.A. 76:5382–5386). Until recently, almost all studies of NGF had focused on its role in the peripheral nervous system, but it now appears that NGF also influences the development and maintenance of specific populations of neurons in the central nervous system (Thoenen et al., 1987, Rev. Physiol. Biochem. Pharmacol. 109:145–178; Whittemore and Seiger, 1987, Brain Res. Rev. 12:439–464).

Neurotrophic factors which have notbeen as well characterized as NGF include brain derived neurotrophic factor (BDNF) and ciliary neurotrophic factor (CNTF).

2.2. Ciliary Neurotrophic Factor

Ciliary neurotrophic factors (CNTFs) are proteins that are specifically required for the survival of embryonic chick ciliary ganglion neurons in vitro (Manthorpe et al., 1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervate the ciliary muscle and sphincter pupillae and also smooth muscle present in the choroid layer of the eye.

Ciliary ganglion neurons have been found to be among the neuronal populations which exhibit defined periods of cell death. In the chick ciliary ganglion, half of the neurons present at embryonic day 8 (E8) have been observed to die before E14 (Landmesser and Pilar, 1974, J. Physiol. 241:737–749). During this same time period, ciliary ganglion neurons are forming connections with their target tissues, namely, the ciliary body and the choroid coat of the eye. Landmesser and Pilar (1974, J. Physiol. 241:715–736) observed that removal of an eye prior to the period of cell death results in the nearly complete loss of ciliary ganglion neurons in the ipsilateral ganglion. Conversely, Narayanan and Narayanan (1978, J. Embryol. Ex. Morphol. 44:53–70) observed that, by implanting an additional eye primordium and thereby increasing the amount of available arget tissue, ciliary ganglion neuronal cell death may be ecreased. These results are consistent with the existence of a neurotrophic factor which acts upon ciliary ganglion neurons.

In culture, ciliary ganglion (CG) neurons have been found to require a factor or factors for survival. Ciliary neurotrophic factor(s) (CNTF) activity has been identified in chick muscle cell conditioned media (Bennett and Nurcombe, 1979, Brain Res. 173:543–548; Nishi and Berg, 1979, Nature 277:232–234; Varon et al., 1979, Brain Res. 173:29–45), in muscle extracts (McLennan and Hendry, 1978, Neurosci. Lett. 10:269–273; Bonhady et al., 1980, Neurosci. Lett. 18:197–201), in chick embryo extract (Varon et al., 1979, Brain Res. 173:29–45; Tuttle et al., 1980, Brain Res. 183:161–180), and in medium conditioned by heart cells (Helfand et al., 1976, Dev. Biol. 50:541–547; Helfand et al., 1978, Exp. Cell Res. 113:39–45; for discussion, see also Adler et al., 1979, Science 204:1434–1436 and Barbin et al., 1984, J. Neurochem. 43:1468–1478).

Adler et al. (1979, Science 204:1434–1436) used an assay system based on microwell cultures of CG neurons to demonstrate that a very rich source of CNTF was found in the intraocular target tissues the CG neurons innervate. Out of 8000 trophic units (TU) present in a twelve-day embryo, 2500 TU were found present in eye tissue; activity appeared to be localized in a fraction containing the ciliary body and choroid coat, with a specific activity approximately twentyfold higher than that found in whole embryo extracts.

Subsequently, Barbin et al. (1984, J. Neurochem. 43:1468–1478) reported a procedure for purifying CNTF from chick embryo eye tissue. CNTF activity was also found to be associated with non-CG tissues, including rat sciatic nerve (Williams et al., 1984, Int. J. Develop. Neurosci 218:460–470). Manthorpe et al. (1986, Brain Res. 367:282–286) reported the purification of mammalian CNTF activity from extracts of adult rat sciatic nerve using a fractionation procedure similar to that employed for isolating CNTF activity from chick eye. In addition, Watters and Hendry (1987, J. Neurochem. 49:705–713) described a method for purifying CNTF activity approximately 20,000-fold from bovine cardiac tissue under non-denaturing conditions using heparin-affinity chromatography. CNTF activity has also been identified in damaged brain tissue (Manthorpe et al., 1983, Brain Res. 267:47–56; Nieto-Sampedro et al., 1983, J. Neurosci. 3:2219–2229).

Carnow et al. (1985, J. Neurosci. 5:1965–1971) and Rudge et al., (1987, Develop. Brain Res. 32:103–110) describe methods for identifying CNTF activity from tissue extracts after blotting cell extracts, separated electrophoretically, onto nitrocellulose paper (Western blotting) and then identifying protein bands containing CNTF activity by inoculating the nitrocellulose with CG neurons and identifying areas of cell survival using vital dyes. These methods were used to determine the apparent molecular weights of the active polypeptides in crude extracts. Using this method, Carnow et al. (1985, J. Neurosci. 5:1965–1971) observed that adult rat sciatic nerve and brain-derived CNTF activities appear to exhibit a different size (24 Kd) than chick CNTF (20.4 Kd).

2.3. Functional Properties of Ciliary Neurotrophic Factor

A number of biologic effects have been ascribed to CNTF although the molecular nature of these activities was not well understood. As discussed above, CNTF was originally described as an activity which supported the survival of neurons of the E8 chick ciliary ganglion, which is a component of the parasympathetic nervous system. A description of other biological properties of preparations known to contain CNTF activity follows:

Saadat et al. (1989, J. Cell Biol. 108:1807–1816) observed that their most highly purified preparation of rat sciatic nerve CNTF induced cholinergic differentiation of newborn rat superior cervical ganglionic neurons in culture. Also, Hoffman (1988, J. Neurochem. 51:109–113) found that CNTF activity derived from chick eye increased the level of choline-O-acetyltransferase activity in retinal monolayer cultures.

Hughes et al. (1988, Nature 335:70–73) studied a population of bipotential glial progenitor cells in the perinatal rat optic nerve and brain; this cell population is believed to give rise to, first, oligodendrocytes and then, second, to type 2 astrocytes. Studies have suggested that oligodendrocyte differentiation occurs from an oligodendrocyte-type 2-astrocyte (O-2A) progenitor cell in the absence of any particular growth factor, whereas type 2 astrocyte differentiation appears to require the presence of a specific inducing protein. Hughes et al. observed that the type 2 astrocyte inducing protein is similar or identical to CNTF (see also Anderson, 1989, Trends Neurosci. 12:83–85).

Heymanns and Unsicker (1987, Proc. Natl. Acad. Sci. U.S.A. 84:7758–7762) observed that high-speed supernatants of neuroblastoma cell extracts produced effects similar to those associated with CNTF activity from chick eye or rat sciatic nerve; the presence of a protein similar but not identical to CNTF (by molecular weight) was indicated.

Ebendal (1987, J. Neurosci. Res. 17:19–24) looked for CNTF activity in a variety of rat and chicken tissues. They observed a fairly wide range of ciliary neuron survival promoting activities among rat, but not chicken, tissues; rat liver, spleen T cells, and submandibular gland cells were found to be associated with low CG survival promoting activity, whereas heart, brain, and skeletal muscle tissues were associated with higher survival promoting activity. Among tissues tested the highest Ciliary Survival promoting activity was observed to be associated with rat kidney.

While the above studies have shown that many tissue and cell extracts contain activities which have similar properties to CNTF, (i.e. they support the survival of E8 chick ciliary ganglion neurons in a tissue culture bioassay), it cannot be assumed that a single or identical protein is responsible for these activities. As shown for the family of fibroblast growth factors (FGFs), for example, a number of distinct polypeptides or protein may possess identical biological activity in a single bioassay.

The neuronal specificity of chick eye and rat sciatic nerve CNTF were initially found to overlap with neuronal populations responsive to NGF. However, distinguishing characteristics between CNTF and NGF became most apparent in studies of the roles of CNTF and NGF in developing neuron populations. Skaper and Varon (1986, Brain Res. 389:39–46) examined the survival requirements of chick dorsal root ganglion (DRG) neurons between embryonic day 6.5 (E6.5) and E15. These DRG neurons, initially responsive only on NGF, were observed to subsequently become responsive to CNTF as well, and eventually appeared increasingly unresponsive to either factor. In addition to differing roles in development, CNTF may also be distinguished from NGF by molecular weight, isoelectric point, inability to be inactivated by antibodies to NGF, and by CNTF's ability to support the in vitro survival of NGF-unresponsive CG neurons (Barbin et al., 1984, J. Neurochem. 43:1468–1478).

3. SUMMARY OF THE INVENTION

The present invention relates to nucleic acid sequences encoding ciliary neurotrophic factor (CNTF) and to the proteins, peptides, and derivatives produced therefrom. In various embodiments of the invention, the nucleic acid sequences, proteins, and peptides of the invention may be used in the treatment of a variety of neurological diseases and disorders, including but not limited to Alzheimer's disease and Parkinson's disease.

In additional embodiments, the CNTF nucleic acids, proteins, and peptides of the invention may be used to treat motorneuron diseases, including but not limited to amyotrophic lateral sclerosis (Lou Gehrig's disease). In a specific embodiment of the invention, CNTF may be used to restore facial nerve function in Bell's palsy. In a further specific embodiment of the invention, CNTF may be used to support the growth of spinal cord neurons, thereby providing a method of treating spinal cord damage caused by trauma, infarction, infection, nutritional deficiency or toxic agents.

Further, the present invention provides a novel method for producing chemically pure CNTF.

The invention also relates to pharmaceutical compositions comprising effective amounts of CNTF gene products which may be used in the diagnosis and treatment of a variety of neurologial diseases and disorders.

The present invention relates to the cloning, sequencing, and expression of CNTF and provides, for the first time, a means for producing human CNTF utilizing human CNTF-encoding nucleic acid sequences. Furthermore, the CNTF nucleic acid sequences of the invention may be used to identify nucleic acid sequences encoding CNTF or CNTF-homologous molecules in a variety of species and tissues. In additional specific embodiments of the invention, a peptide fragment having CNTF activity has been identified, and antibody to a CNTF peptide that neutralizes CNTF activity has been produced.

3.1. Abbreviations

| | |
|---|---|
| BRCN | cyanogen bromide |
| CG | ciliary ganglion |
| CNTF | ciliary neurotrophic factor |
| DRG | dorsal root ganglion |
| E8, E9, etc. | embryonic day 8 or 9, etc. |
| GFAP | glial fibrillary acidic protein |
| NGF | nerve growth factor |
| TU | trophic unit. One trophic unit per ml equals the amount of CNTF activity supporting half-maximal neuronal survival per ml of culture medium. |

4. DESCRIPTION OF THE FIGURES

FIG. 1. cDNA cloning (a), nucleotide and deduced amino acid sequence of rat CNTF (b). The oligonucleotides used as primers are shown in (c) and their corresponding positions in b). Underlined amino acids in b) correspond to the peptide sequences obtained from tryptic (T1–8) and BRCN (CB1–4) fragments of CNTF. At the nucleotide level, sequences corresponding to the coding region are bold-faced and the polyadenylation signal sequence is underlined. Amino acid composition of CNTF as derived from purified CNTF and as predicted from CNTF cDNA(d).

FIG. 2. Two-dimensional gel electrophoresis of CNTF which was purified (a) using DEAE-ion exchange chromatography and preparative SDS-polyacrylamide gel electrophoresis; and (b) using DEAE-ion exchange chromatography, preparative SDS-polyacrylamide gel electrophoresis,and further purified by chromatography using a Bakerbond Gold C4 Widepore column.

Figure 3A:
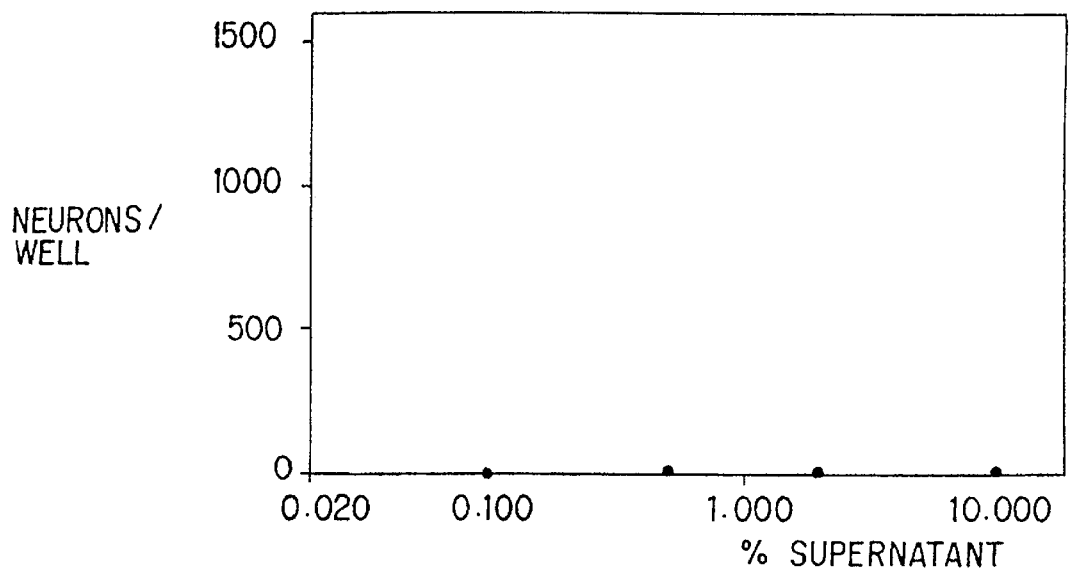
Figure 3B:
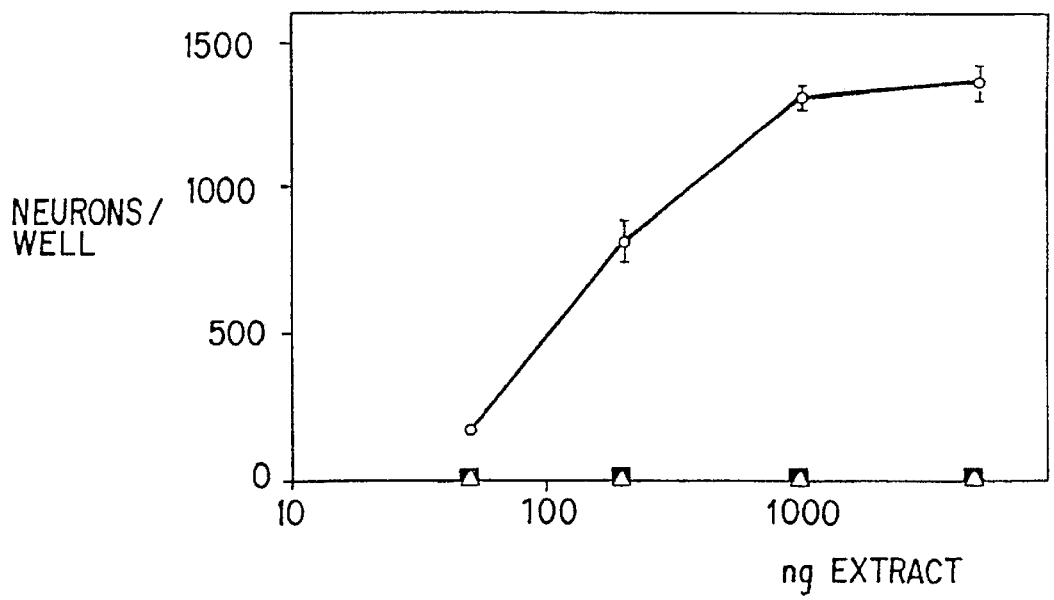

FIG. 3. Survival of cultured E8 chick ciliary neurons in the presence of supernatants and extracts of transfected HeLa cells: Embryonic day 8 ciliary neurons were grown in the presence of supernatants (a) and extracts (b) of HeLa-cells transfected with plasmid without insert (Δ) and plasmid containing rat CNTF cDNA clone E in sense (○) and antisense (■) orientation.

Figure 4A:
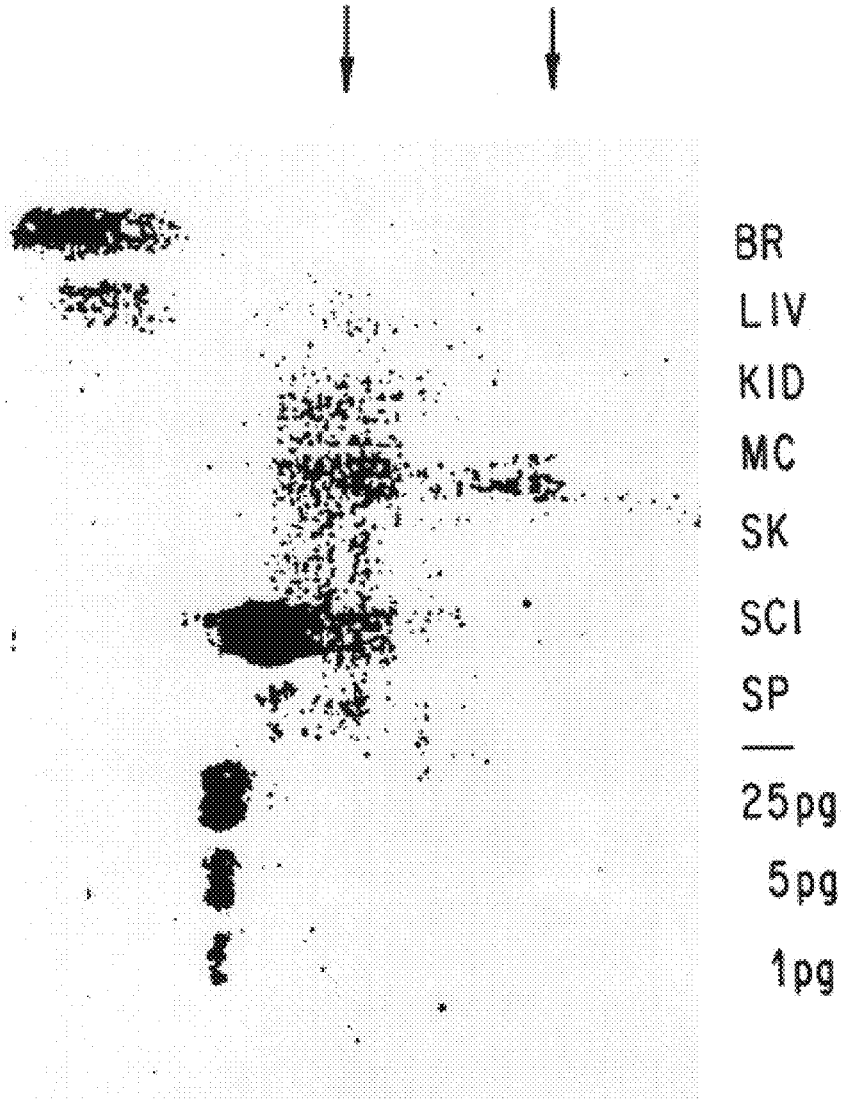
Figure 4B:
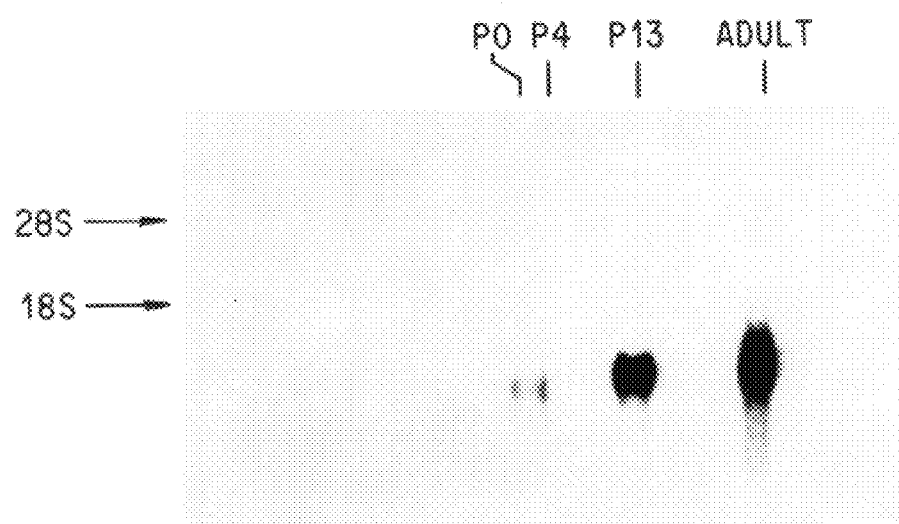

FIG. 4. Northern blot analysis of CNTF-mRNA in tissues of the adult rat (abbreviations used are: BR, brain; LIV, liver; KID, kidney; MC, muscle; SK, skin; SCI, sciatic nerve; SP, spinal cord); (b) RNA derived from sciatic nerve of newborn (PO), four day old (P4) and 13 day old rat pups.

Figure 5:
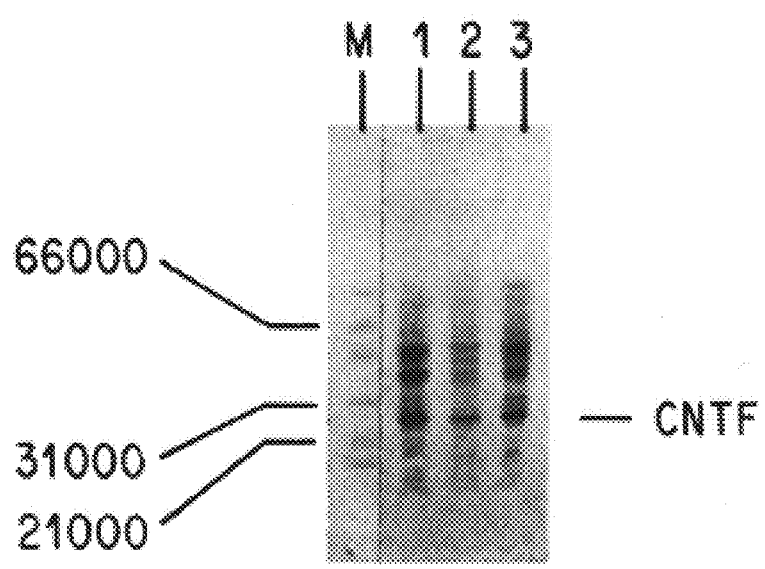

FIG. 5. Recombinant rCNTF in three different E. coli strains. Lane M=Standard protein markers; the molecular weights of three proteins are indicated. Lanes 1–3: total protein extracted from E. coli W3110qF-, E. coli HB101 and E. coli MC1061 each hosting pCP-rCNTF-C-1. Extracts were prepared and analysed on a 8–25% polyacrylamide gradient gel as previously described. (Panayotatos, N. and Fontaine, A., 1988, J. Biol. Chem. 260:3173–3177).

Figure 6A:
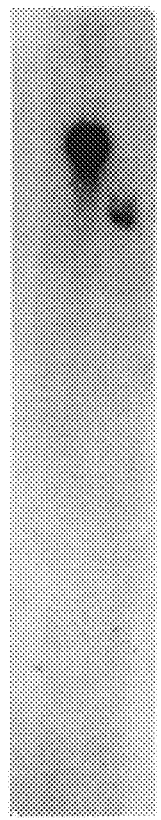
Figure 6B:
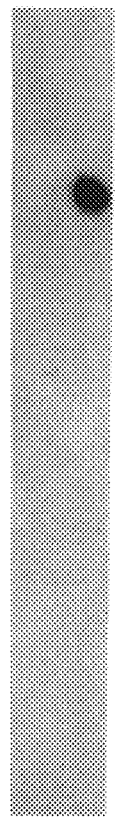

FIG. 6. a) PCR generated human CNTF probe in Southern blot hybridization to Eco Rl digests of human and rat genomic DNAs. b) Radioactive rat CNTF probe in Southern blot hybridization to Eco R1 digests of human and rat genomic DNAs.

FIG. 7. Partial CNTF coding sequence from human genomic DNA amplified by PCR; comparison with known rat CNTF coding sequence. Differences between human and rat in deduced amino acid sequence are shown by an asterisk (*). Differences in DNA sequence indicated by a not equal sign (≠).

FIG. 8. Sequence of Human CNTF. (a) human nucleic acid and amino acid sequence; (b) comparison of human and rat amino acid sequences; (c) comparison of human and rat nucleotide sequence; and (d) full restriction map of human genomic CNTF sequence.

Figure 9:
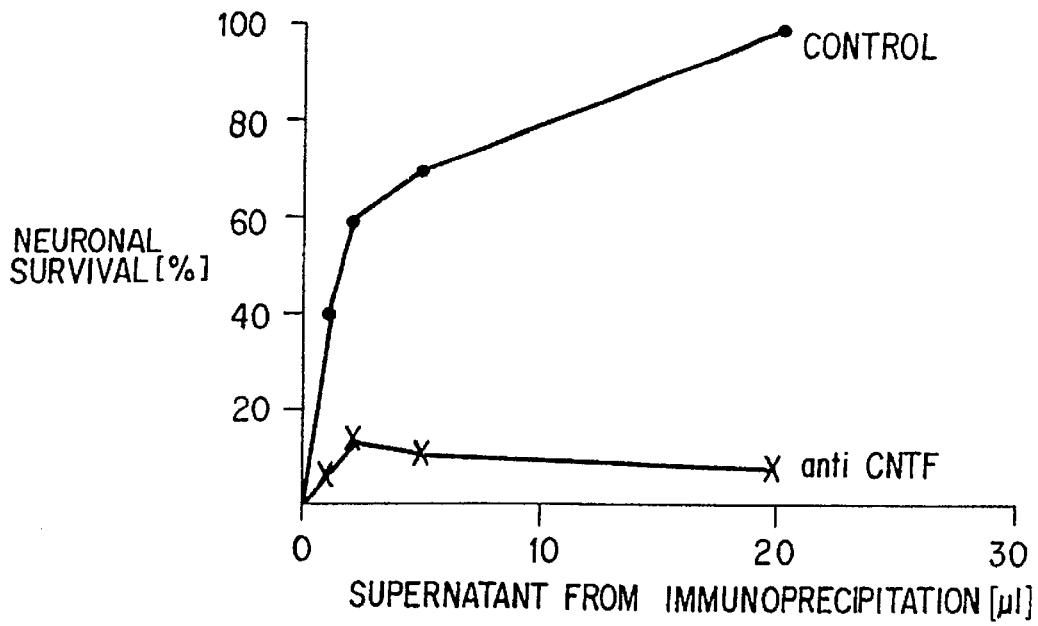

FIG. 9. Antibodies to a synthetic peptide (14 amino acids—I S A L E S H Y G A K D K Q) based on the sequence of CNTF (C-terminal region) are able to inhibit the biological activity of purified rat CNTF after immunoprecipitation.

Figure 10:
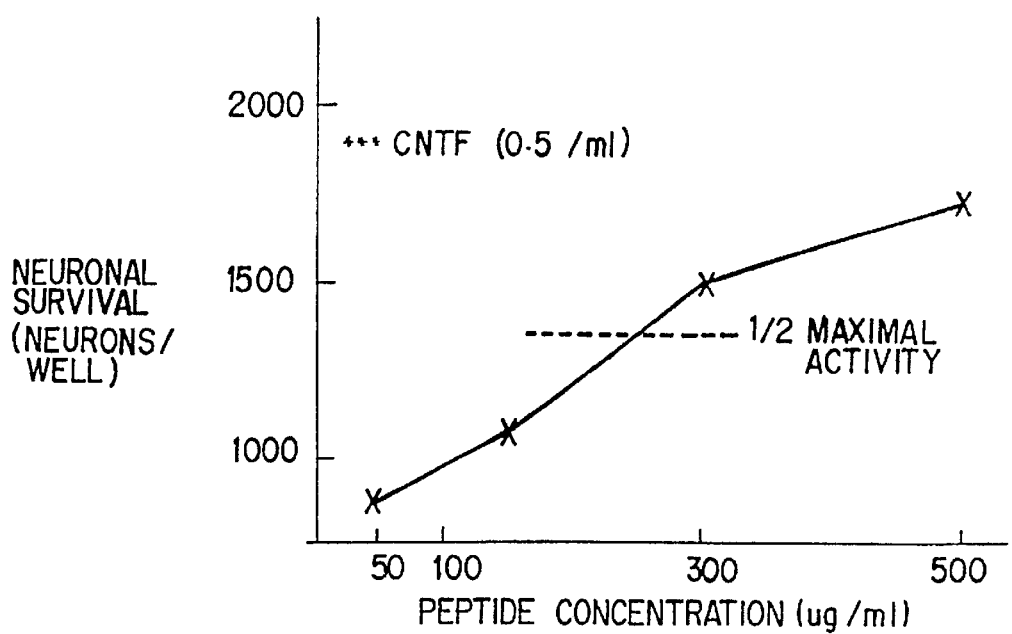

FIG. 10. Demonstration of neurotrophic activity of a 28 amino acid synthetic CNTF peptide fragment.

Figure 11:
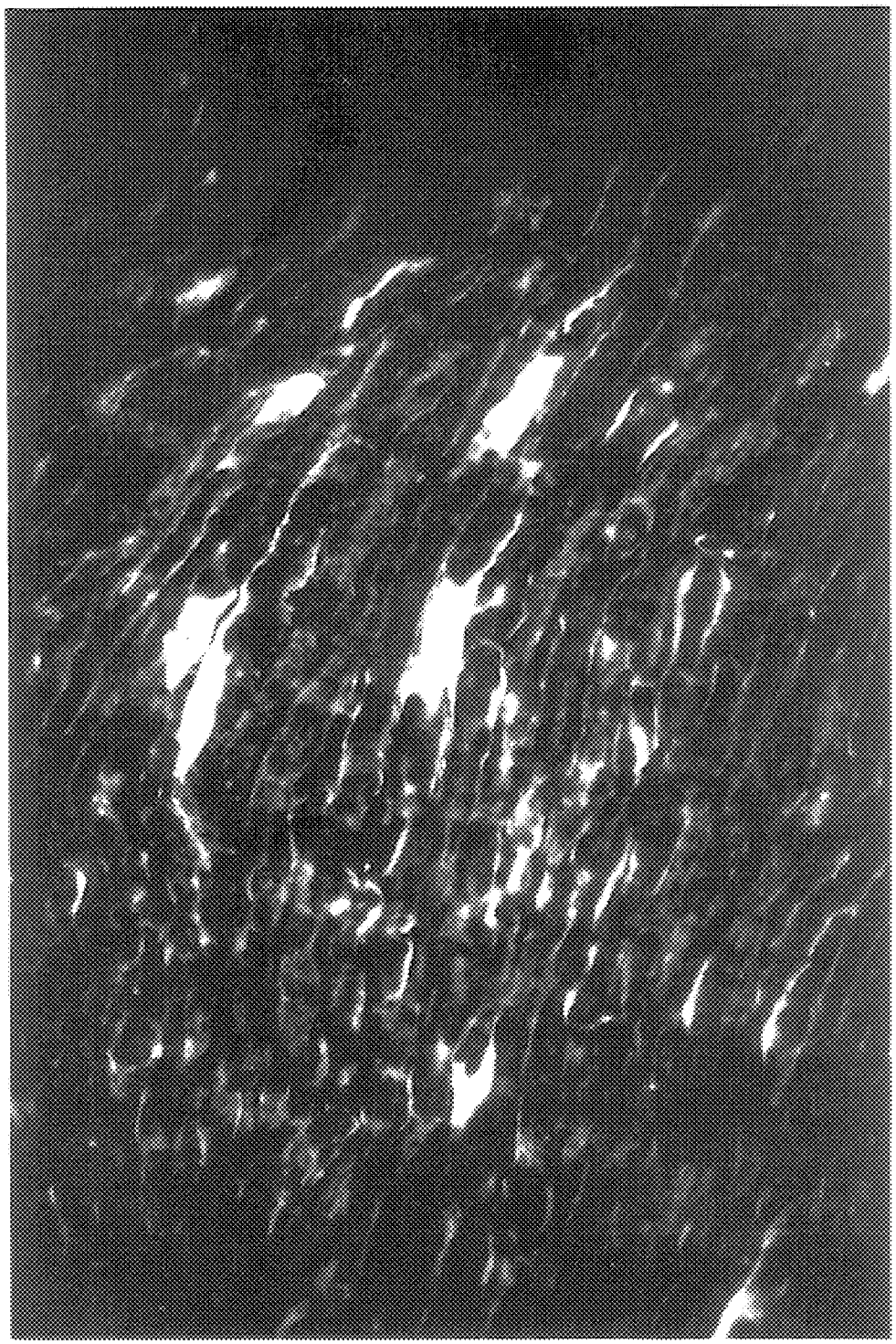

FIG. 11. Indirect immunofluorescence studies using rabbit antibodies toward a 28 amino acid CNTF biologically active peptide bound to fixed rat sciatic nerve sections and subsequently reacted with rhodamine labelled anti-rabbit IgG. Large arrow indicates periaxonal staining; small arrow points to labelled axonic structures.

Figure 12A:
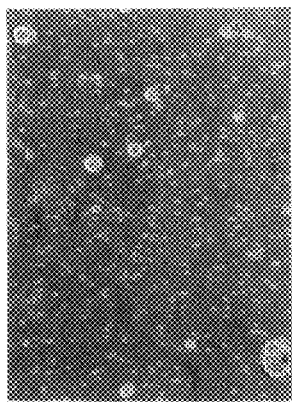
Figure 12B:
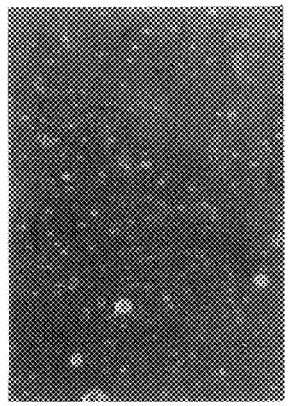
Figure 12C:
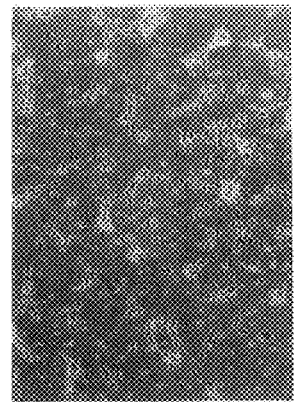

FIG. 12. Phase-contrast photomicrographs of dissociated cultures of E14 rat mediodorsal spinal cord cells grown for 72 hours on a polyornithine substrate in the presence of:
A. Control medium;
B. Medium supplemented with mouse nerve growth factor (NGF) or;
C. Medium supplemented with recombinant rat ciliary neuronotrophic factor (CNTF) produced in E. coli.
Note extensive neuronal survival and neurite outgrowth in the presence of CNTF Scale Bar=100 µm.

FIG. 13. Motor neuron and glial cell changes in facial nerve nuclei of newborn rats with unilateral facial nerve lesions. Unilateral nerve lesion bearing BSA containing gelfoam implant (A) Nissl-stained motorneurons in facial nucleus on lesioned side; (B) Nissl-stained motor neurons in facial nucleus on unlesioned side (control); (C) facial nucleus on lesioned side stained with anti-GFAP antibody; and (D) facial nucleus on unlesioned side stained with anti-GFAP antibody.

FIG. 14. Motor neuron and glial cell changes in facial nerve nuclei of newborn rats with unilateral facial nerve lesions. Unilateral nerve lesion bearing CNTF containing gelfoam implant (A) Nissl-stained motorneurons in facial nucleus on lesioned side; (B) Nissl-stained motor neurons in facial nucleus on unlesioned side (control); (C) facial nucleus on lesioned side stained with anti-GFAP antibody; and (D) facial nucleus on unlesioned side stained with anti-GFAP antibody.

FIG. 15. Computer generated plots of hydrophilicity, surface probability, flexibility, antigenic index, amphiphilic helix, amphiphilic sheet, and secondary structure of (a) rat and (b) human CNTF.

Figure 16:
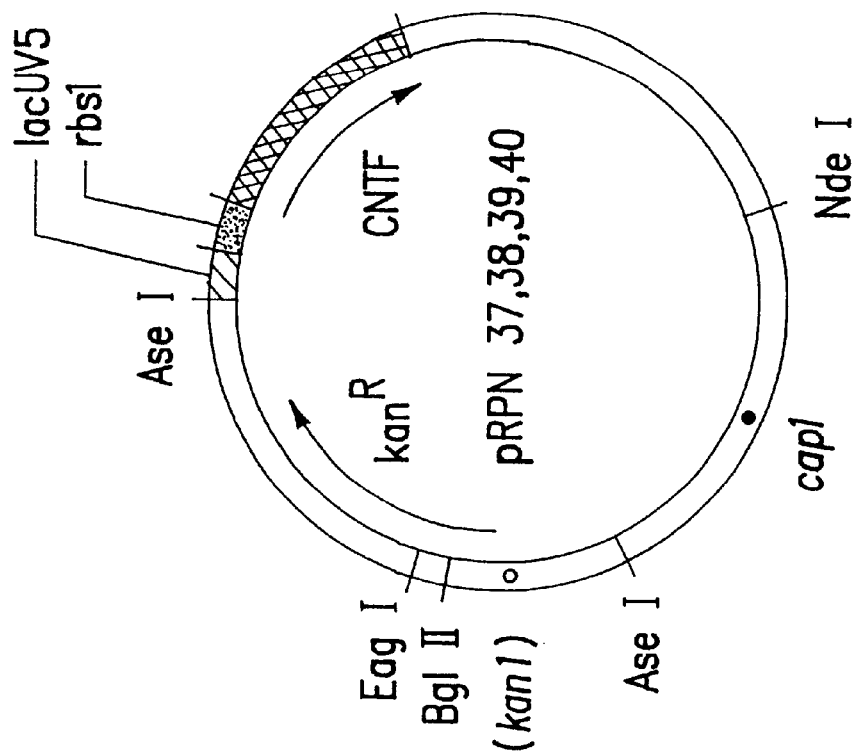
Figure 16:
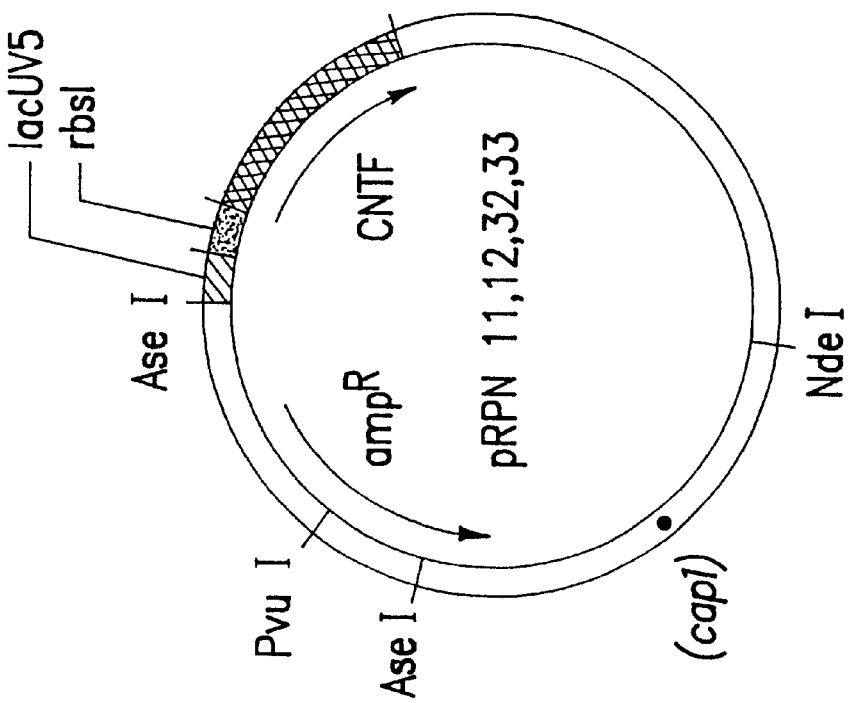

FIG. 16. Main features of the expression plasmids. The promoter (lacUV5), the ribosome binding site (rbs1), the CNTF, ampR and kanR genes, as well as the cop1 (0) and kan1 (0) mutations are indicated. The restriction sites AseI, EagI, NdeI and PvuI were used in plasmid constructions, as described in the text.

FIG. 17. Sequence of human CNTF and the PCR primers used in cloning. The DNA sequence of the protein-coding region is shown in bold with the deduced protein sequence above. Solid arrowheads indicate the last nucleotide of exon 1 and the first nucleotide of exon 2; the 5'- and 3'-terminal intron sequences are shown in brackets above the arrowheads. The location and 5' to 3' polarity of selected oligodeoxynucleotide primers is shown by arrows. Asterisks denote mismatches. The oligodeoxynucleotide sequences of the primers (5' to 3') are as follows:

CNTF.23: GCTTTCACAGAGCATTCACCG;
CNTF.21: AGGCCCTGATGCTTCACATAGGATTC-CGTAAGAG;
CNTF.22: CTCTTACGGAATCCTATGTGAAGCAT-CAGGGCCT;
CNTF.24: GAGACGGCCGTAACTGTTACATTTTCT-TGTTGTTAG;
CNTF.10: CCAAGCTTCTAGAATTCGCAGGCATC-CCATCAGCCT;
CNTF 11: GACTCGAGTCGACATCGGAGATGACT-GAGGCAGA.

Figure 18A:
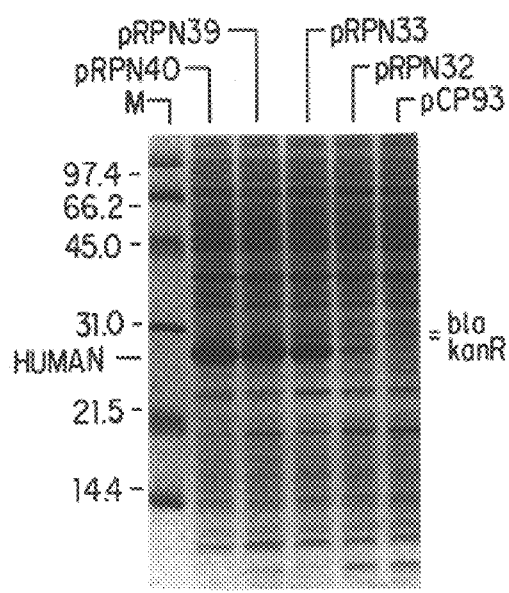
Figure 18B:
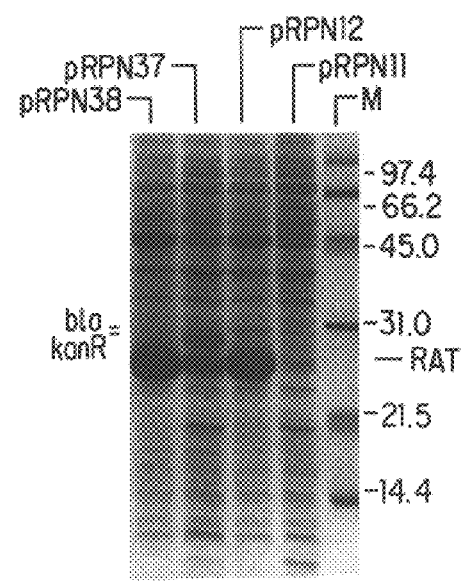

FIG. 18. Comparison of human and rat CNTF expression using various vectors. Total protein from the indicated strains was analyzed on 8–25% polyacrylamide gels stained with Coomassie. Molecular weights of the markers (in hundreds) are indicated (M), as well as the positions of bands corresponding to the human CNTF, rat CNTF, ampR and kanR proteins.

FIG. 19. Purification of CNTF. (A): rat CNTF; (B): human CNTF. Lysate: total cellular protein; 8 M GuHCl: dialyzed extract; 0.5, 5, 10, and 50: amount of protein in µg loaded on each lane after DEAE-Sephacel or Fast-S.

Figure 20:
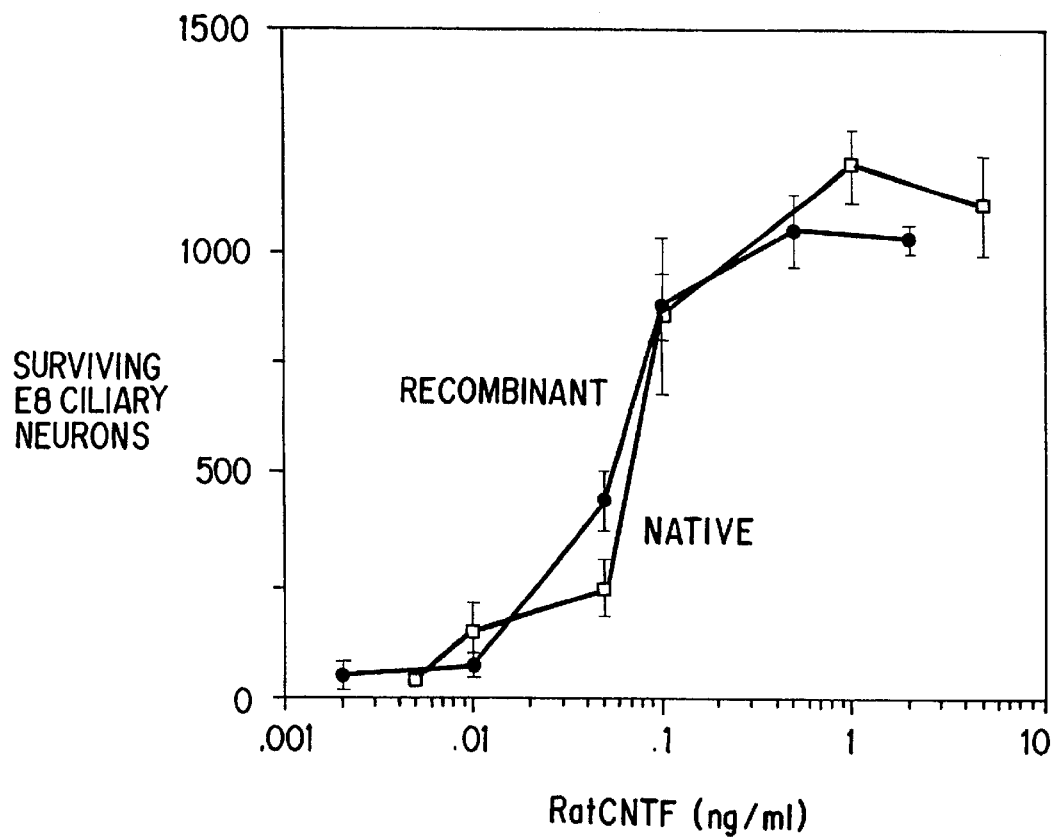

FIG. 20. Dose response of ciliary neurons to native and recombinant rat CNTF. Survival of dissociated E8 chick ciliary neurons in the presence of increasing amounts of rat CNTF was measured as described in Section 12.7.

FIG. 21. Photomicrographs of explant cultures (A, B) of E10 chick embryo dorsal root ganglia (DRG) and dissociated, neuron-enriched cultures (C, D, E) of E8 chick embryo ciliary ganglia (CG). A, B are darkfield micrographs of control (A) and CNTF treated (B; 5 ng/ml) explants of DRG after 48 hr in culture. C, D, E are phase contrast micrographs of control (C) and CNTF-treated (D, 100 pg/ml; E, 5 ng/ml) dissociated cultures of ciliary ganglion neurons. Scale bar=400 µm (A,B) and 50 µm (C,D,E).

FIG. 22. Aligned sequences of CNTF proteins. The amino acid sequences of human (hu), rat (rt) and rabbit (rb) CNTF are shown. The expression vector encoding each of these molecules is indicated on the right hand side. In panel (A), dots indicate residues identical to the wild type human CNTF sequence. In panel (b), dots indicate residues identical to the wild type of sequence from the same species. Residues different from the wild type are shown in capital letters. Extra residues fused as part of a foreign peptide are shown in small italic characters.

Figure 23:
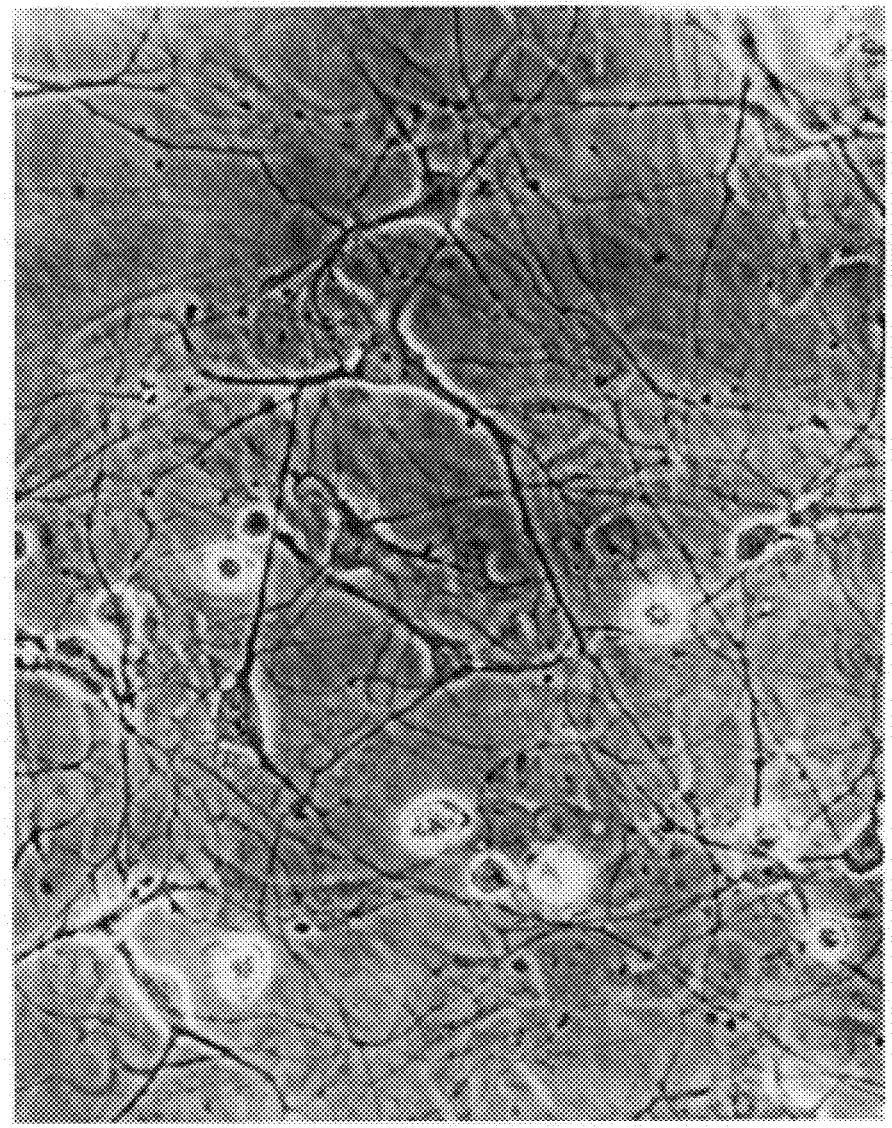

FIG. 23. Phase contrast micrograph of ventral spinal cord cells after 6 days in culture. The cells were plated at $0.5 \times 10^6$ cells/35 mm dish and maintained in $F12MEMHS_5FCS_5$. 20×.

Figure 24:
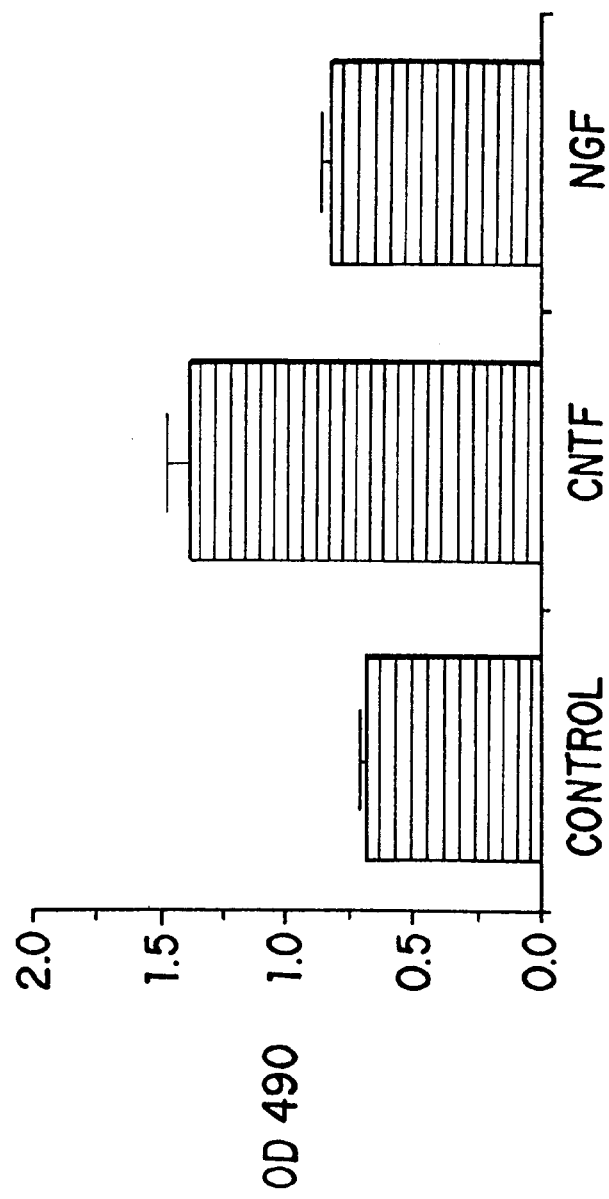

FIG. 24. Neurofilament (NF) levels in ventral spinal cord neuron cultures. Cultures were treated at the day of plating with CNTF (10 ng/ml) or NGF (50 ng/ml), and assayed for NF levels on day 7. NF protein was detected with NF-antibody (RT97), reaction products were visualized using OPD as a substrate, and OD (mean±SEM) was measured at 490 nm. n=3.

Figure 25:
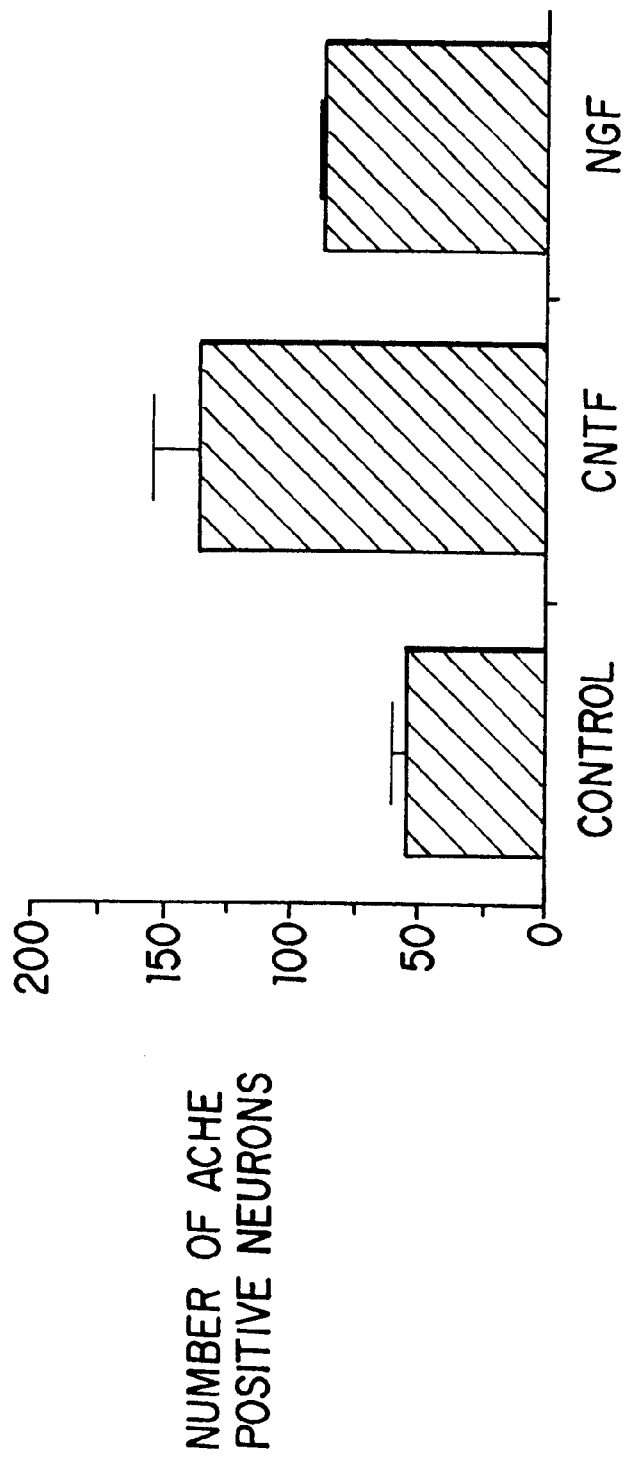

FIG. 25. Effects of CNTF on survival of AchE-containing neurons. Ventral spinal cord neurons were grown in culture for 7 days and then processed for AchE histochemistry. Stained cells were counted under 32× and expressed as total number per 35 mm dish. n=3.

Figure 26A:
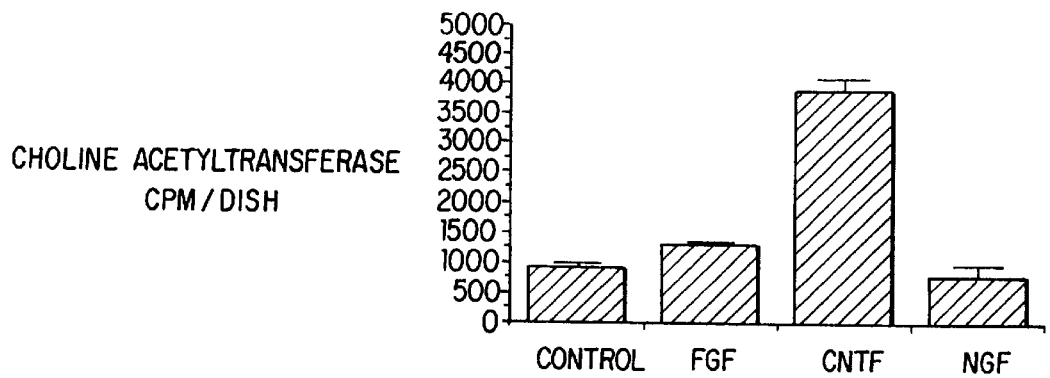

FIG. 26. A. Effects of growth factors on CAT activity in ventral spinal cord culture. Cultures were treated with FGF (50 ng/ml), CNTF (10 ng/ml), NGF (50 ng/ml), or PBS/BSA (0.5 mg/ml) on the day of plating. They were then harvested on day 7 and assayed for CAT levels. CAT is expressed in CPM/35 mm dish (mean SEM). n=3. B. Effects of increasing doses of CNTF on CAT activity. Ventral horn cells were treated with different doses of CNTF (ng/ml) on the day of plating. On day 7 the cultures were harvested for measurement of CAT activity (expressed in pmole/hr/35 mm dish; mean±SEM). n=3 for each dose.

Figure 27A:
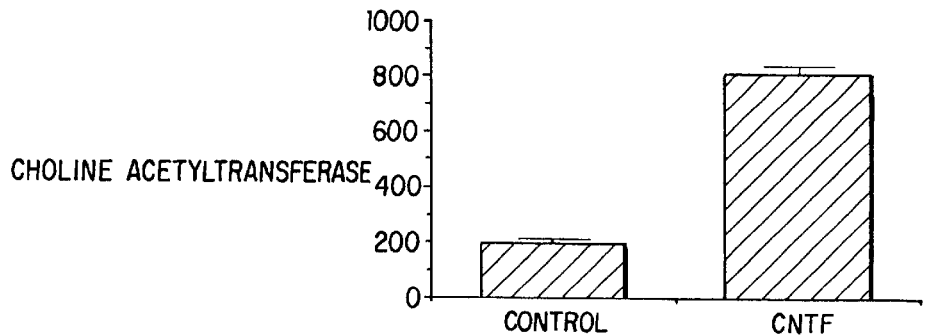
Figure 27B:
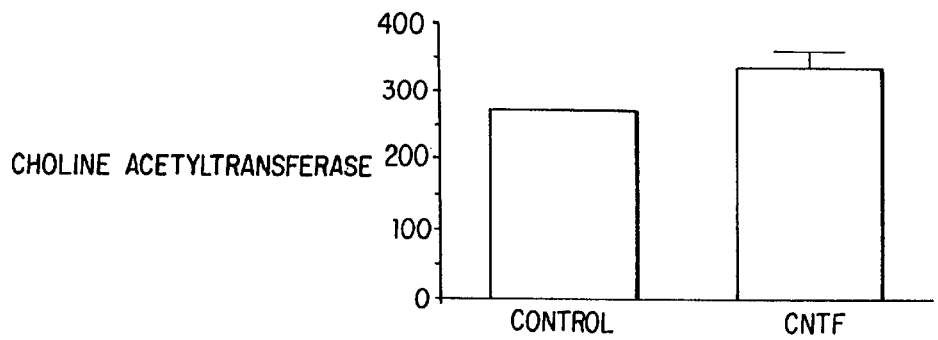
Figure 27C:
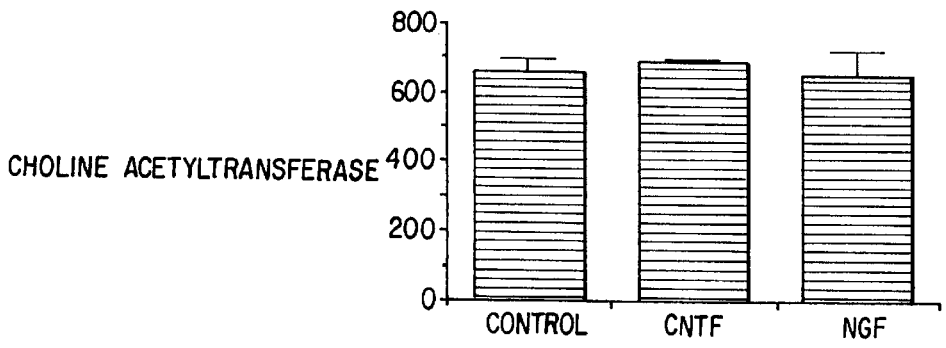

FIG. 27. Effects of CNTF on CAT activity after delayed addition. CNTF (10 ng/ml) was added to cultures on either day 0, 2, or 6 and harvested for measurement of CAT activity on day 7, 9, and 13, respectively. CAT is expressed in CPM/ug protein/35 mm dish (mean±SEM). n=3.

Figure 28:
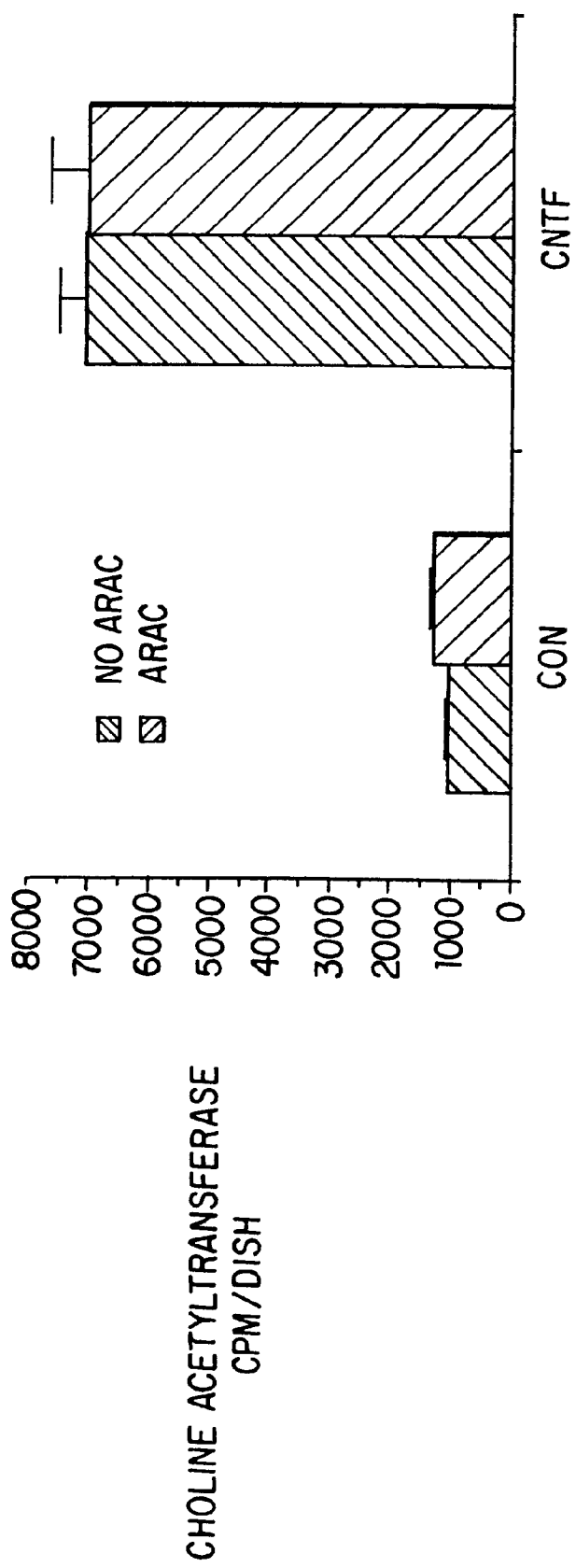

FIG. 28. Effects of CNTF (10 ng/mlL) on CAT activity in ventral spinal cord cultures with reduced glia. Ara C (0.5 uM) was added to cultures on day 2. On day 7, cells were harvested and assayed for CAT activity (Expresed in CPM/35 mm dish; mean±SEM). n=3.

FIG. 29. Effects of CNTF (10 ng/ml) and NGF (50 ng/ml) on CAT activity in metrizamide gradient purified ventral spinal cord neurons. CAT (mean±SEM) is expressed in pmole/hr/16 mm well. n=3.

FIG. 30. Time course of the increase in high affinity GABA uptake in CNTF-treated hippocampal cultures. Hippocampal neurons were put into culture and maintained in the presence or absence of CNTF (10 ng/ml) for various periods of time prior to measurement of GABA uptake (A) and neurofilament protein levels (B). Results represent percentage of activity in treated cultures when compared to non-treated control cultures.

FIG. 31. Dose responsive curves of hippocampal neurons to CNTF. Hippocampal neurons were cultured in the presence or absence of various concentrations of CNTF (0.001–10 ng/ml) for 8 days. At the end of the culture period, high affinity GABA uptake (A), neurofilament protein levels (B), and GAD enzyme activity (C) were measured.

FIG. 32. Effect of CNTF on the number of NSE-, GAD- and calbindin-positive cells. Hippocampal neurons were maintained in culture in the presence or absence of CNTF (10 ng/ml) for 8 days. Immunostaining for NSE, GAD and calbindin were performed, as shown in A and B.

Figure 33A:
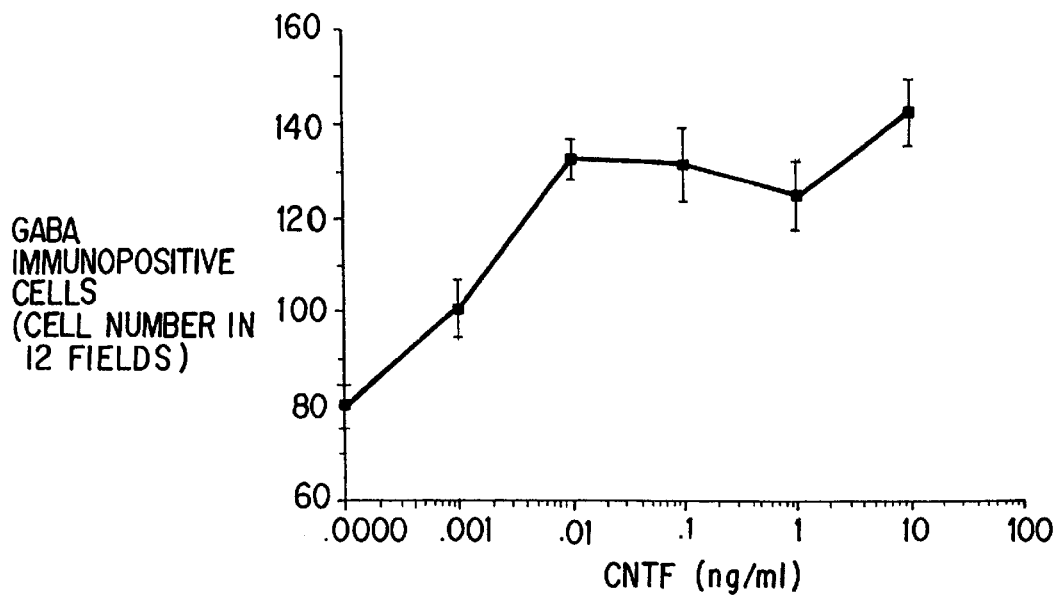

FIG. 33. Dose-dependent response of CNTF on the number of GABA- and AchE-immunopositive neurons. Hippocampal neurons were grown in culture in the presence of various concentrations of CNTF (0.001–10 ng/ml). Immunostaining for GABA and AchE were performed, as shown in A and B.

FIG. 34. Effects of delaying the addition of CNTF on the CNTF-induced increase in high affinity GABA uptake. A. CNTF (10 ng/ml) was added following a delay of 0, 1, 2, 3 or 4 days after the hippocampal cells were put into culture. High affinity GABA uptake was determined on the eighth day in culture. B. CNTF (10 ng/ml) was added to the hippocampal cells following a delay of 0 or 3 days, and high affinity GABA uptake was determined on the eleventh day in culture.

FIG. 35. Effects of delaying the addition of CNTF on the CNTF-induced increase in neurofilament protein levels. A. CNTF (10 ng/ml) was added at different times (0, 1, 2 or 3 days) after the hippocampal cells were put into culture. Neurofilament protein levels were measured on the eighth day. B. CNTF (10 ng/ml) was added to the hippocampal cells following a delay of 0 or 3 days, and neurofilament protein level was determined on the eleventh day.

Figure 36:
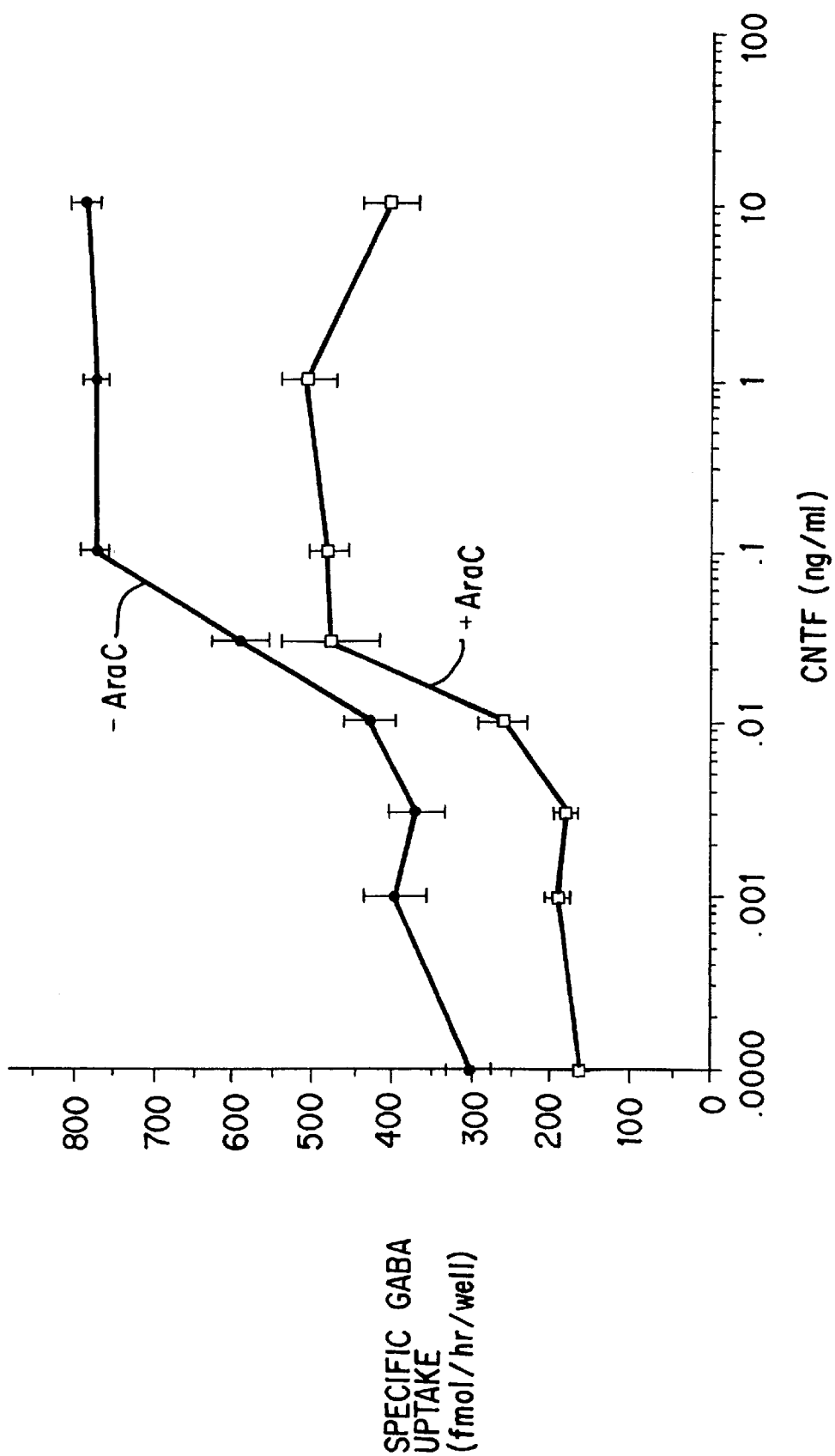

FIG. 36. Effect of CNTF in neuron-enriched cultures. Hippocampal cultures were maintained in the presence or absence of various concentrations of CNTF (0.001–10 ng/ml) for 8 days. Cytosine arabinoside (0.3 uM) was added to the hippocampal cultures for 24 h to reduce the number of glia. High affinity Gaba uptake was measured on the eighth day in culture.

FIG. 37. Density-dependence of CNTF-induced increase in GABA uptake and neurofilament protein levels. Hippocampal cells were plated at a density of 71, 400 cells/cm$^2$. The cells were maintained in the presence or absence of CNTF (10 ng/ml) for 8 days prior to the measurement of GABA uptake (A) and neurofilament protein levels (B).

Figure 38:
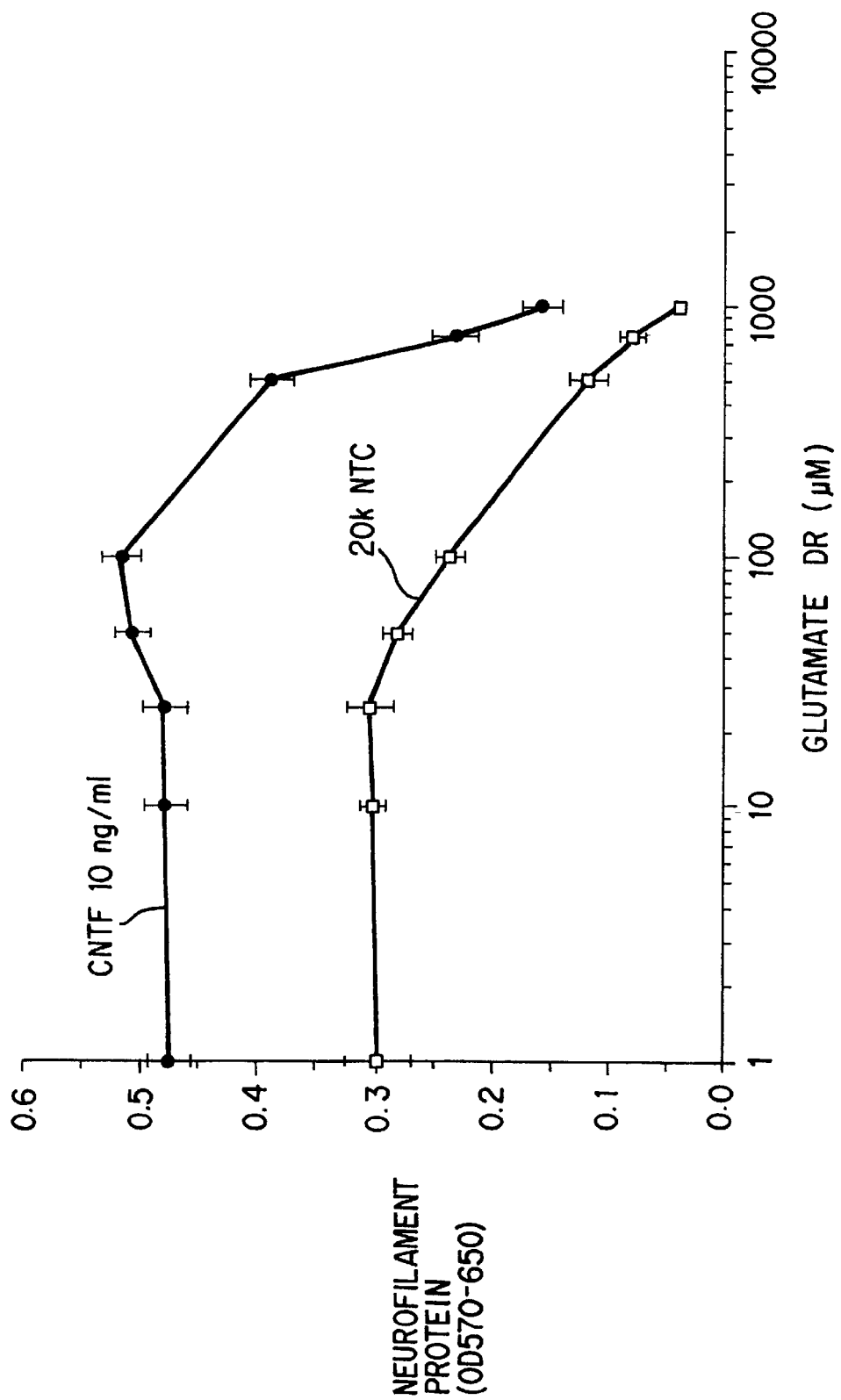

FIG. 38. Protective effect of CNTF on glutamate-induced toxicity in hippocampal cultures. Hippocampal neurons were maintained in culture in the presence or absence of CNTF (10 ng/ml) for 7 days. Glutamate at various concentations (100–1000 uM) was added for 15 minutes, after which the cells were cultured in the absence of glutamate or CNTF for 20 h. Survival of cells at the end of the culture period was assessed by MTT assay based on the conversion of MTT (3-(4,5-dimethylthiazol-2-yl)-2,5-diphenyl tetrazolium bromide) to a purple product by vital cells. MTT dye was added to a final concentration of 0.5 mg/ml. Dyes taken up by live cells were solubilized by the addition of 0.08N HCI in isopropranol 5 hours later, and O.D. (570–650 nm) was measured.

Figure 40:
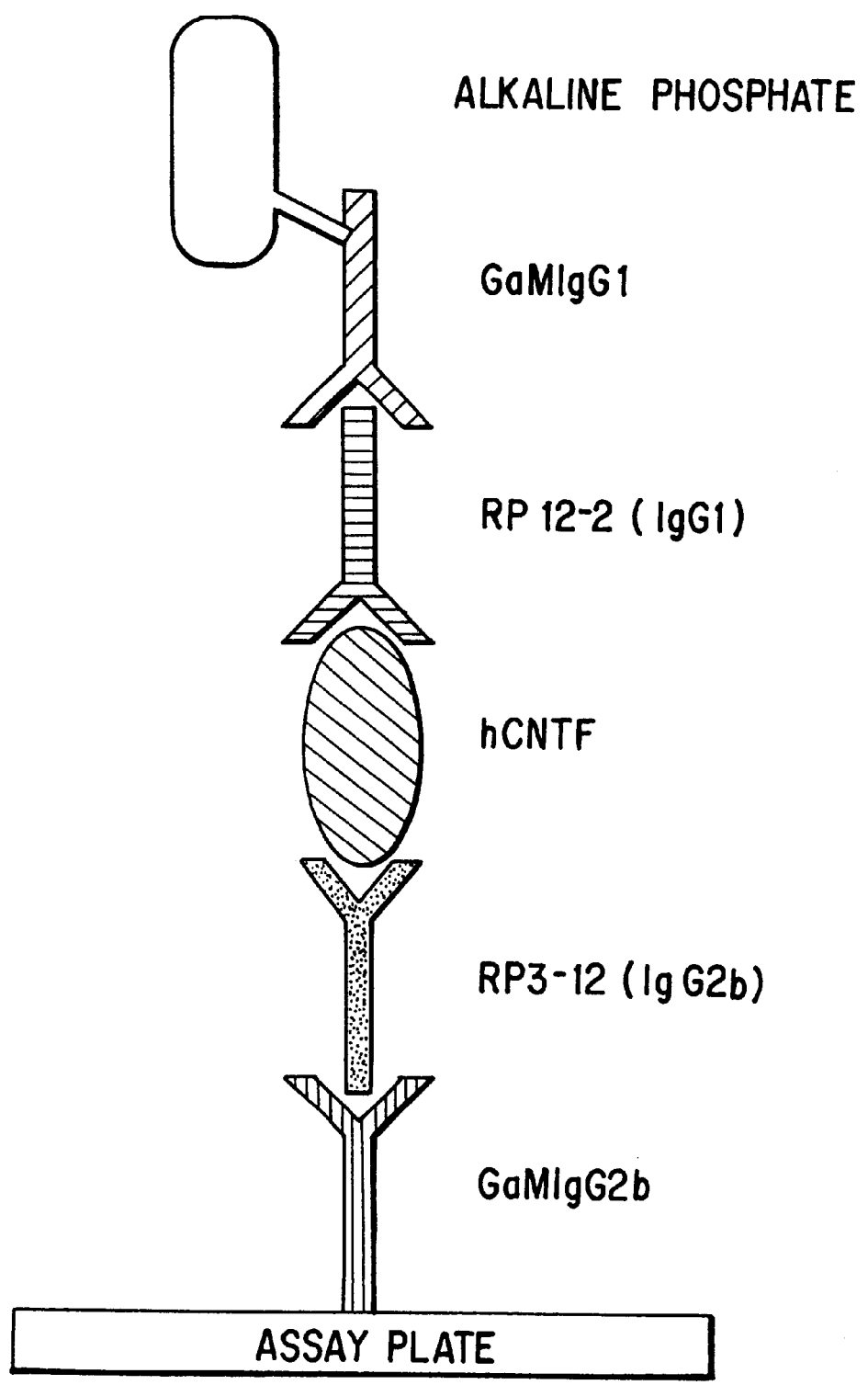

FIG. 40. Two antibody sandwich assay for CNTF. ELISA plates (Falcon 3915 probind) were coated with 50 $\mu$l/well of 4 $\mu$g/ml goat anti-mouse IgG2b (GaMIgG2b, Caltag). Plates were incubated for 4° overnight, washed and blocked for 2 hrs. at r.t. in 50 mM bicarbonate buffer, pH9.b. After washing, 50 $\mu$l/well of capture antibody RP3-12 (1:5 dilution of hybridoma culture supermnatant) was added and incubated for 1 hr. at r.t. After washing, serial dilutions of a human CNTF standard was added (range 10 ng/ml–7 pg/ml) or serial dilutions of a test sample. After 1 hr. at r.t., followed by washing, 50 $\mu$l/well of a reporter antibody RP12-2 (1:5 dilution of culture supernatant) was added, and incubated for 1 hr. at r.t. After washing, 50 $\mu$l/well of a 1:1000 dilution of alkaline phosphatase labelled goat anti-mouse IgG1 (GaMIgG1, Caltag) reagent was added. The plate was incubated, for 1 hr. at r.t. followed by washing, developed with pNPP and read at 405 nM in an ELISA reader (Molecular Devices Thermo Max).

Figure 41:
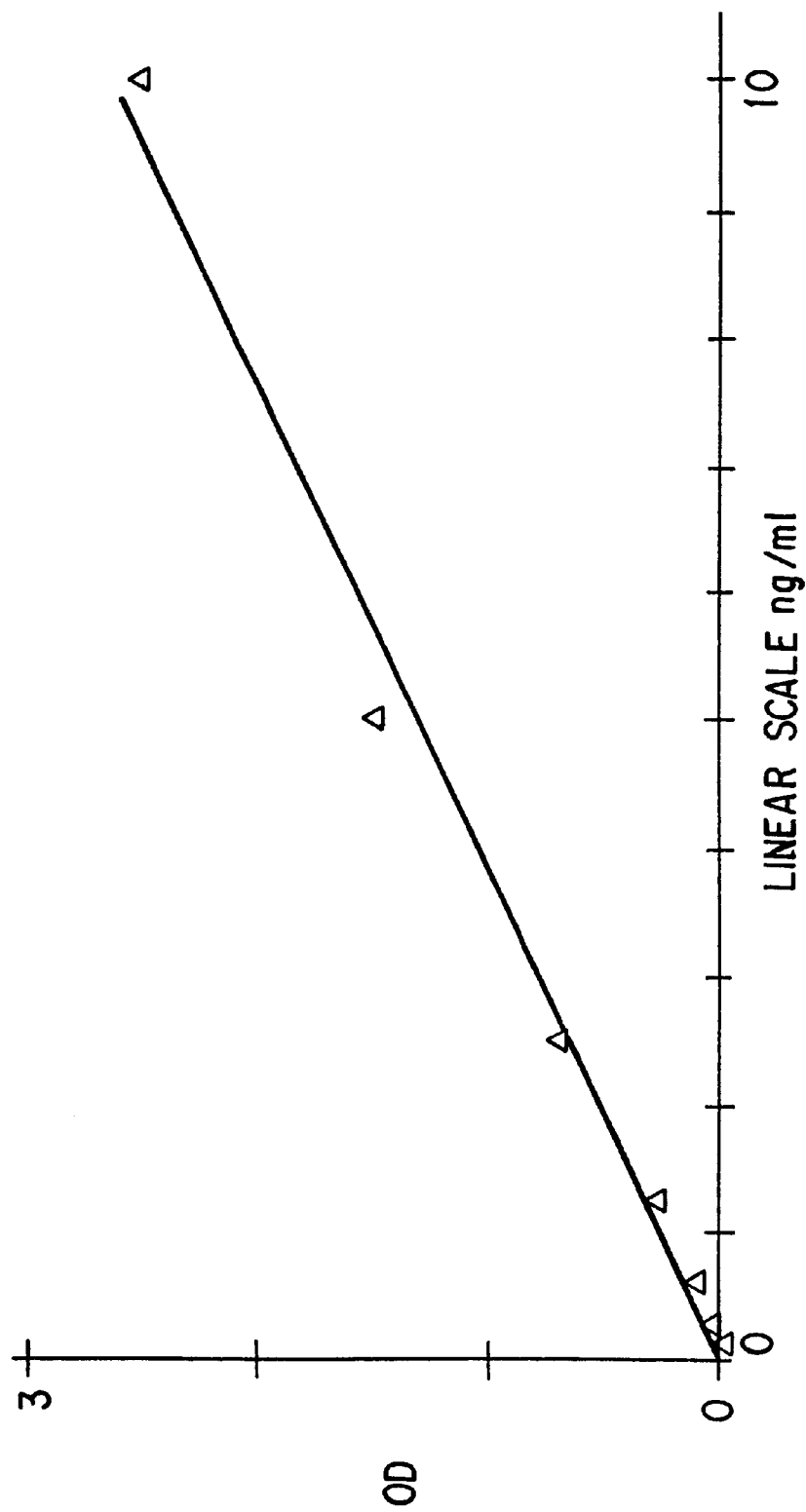

FIG. 41. Results of 2 antibody sandwich assay for human CNTF. Increasing amounts of recombinant human CNTF were assayed using monoclonal antibodies RP3-12 and RP12-2, in the reaction described in FIG. 40.

FIG. 42. Chick embryonic spinal motor neurons retrogradely labeled with rhodamine isothiocyanate. Cells were fixed with 4% formaldehyde after 5 hrs in culture. (A) Phase-contrast and (B) fluorescence pictures of the same field. Scale bar=25 $\mu$m. Note that the smaller cell at the right is not labeled.

Figure 43:
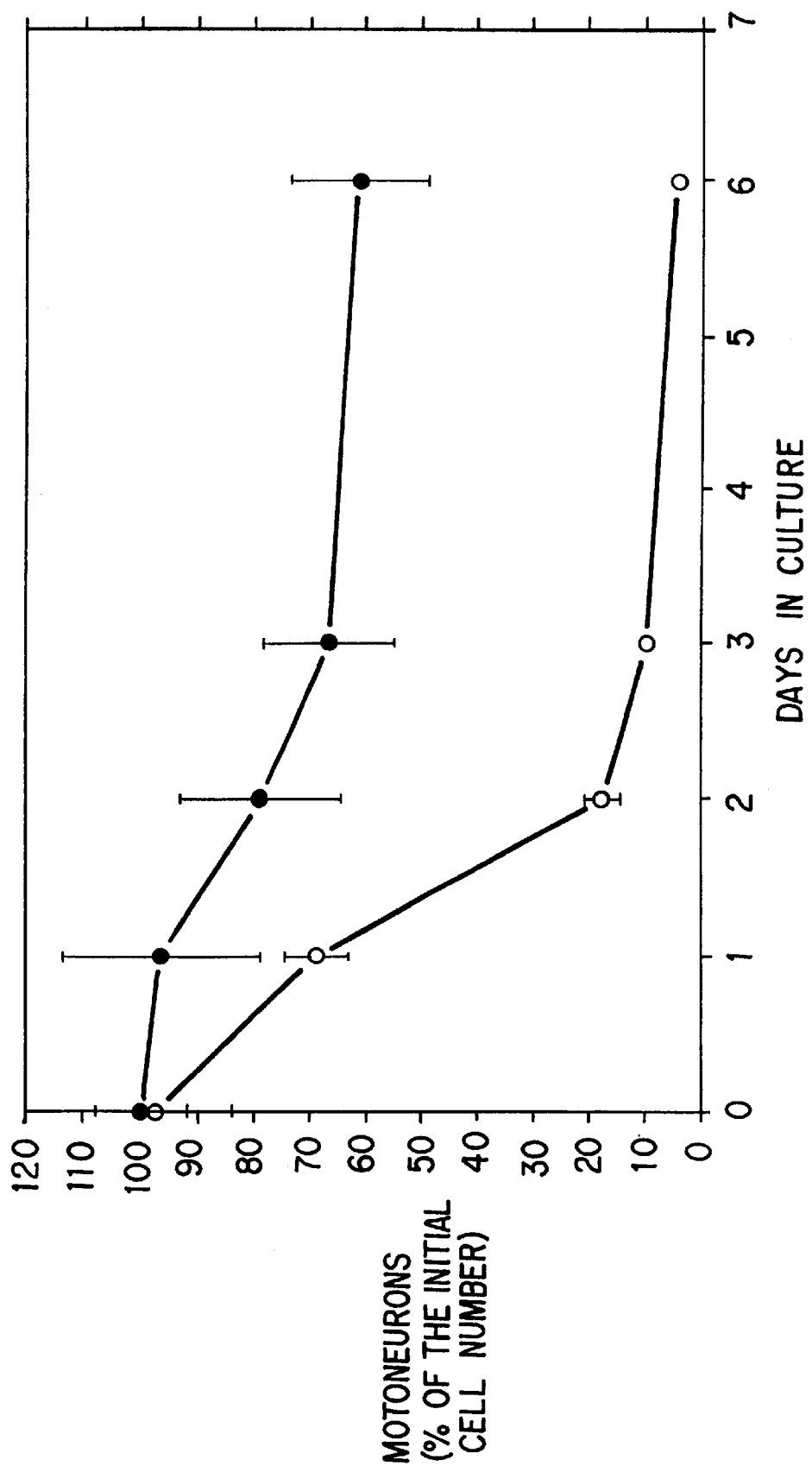

FIG. 43. Time-course of survival of chick embryonic spinal motorneurons in the presence (closed circles) or in the absence (open circles) of recombinant rat CNTF, 5 ng/ml.

Figure 44A:
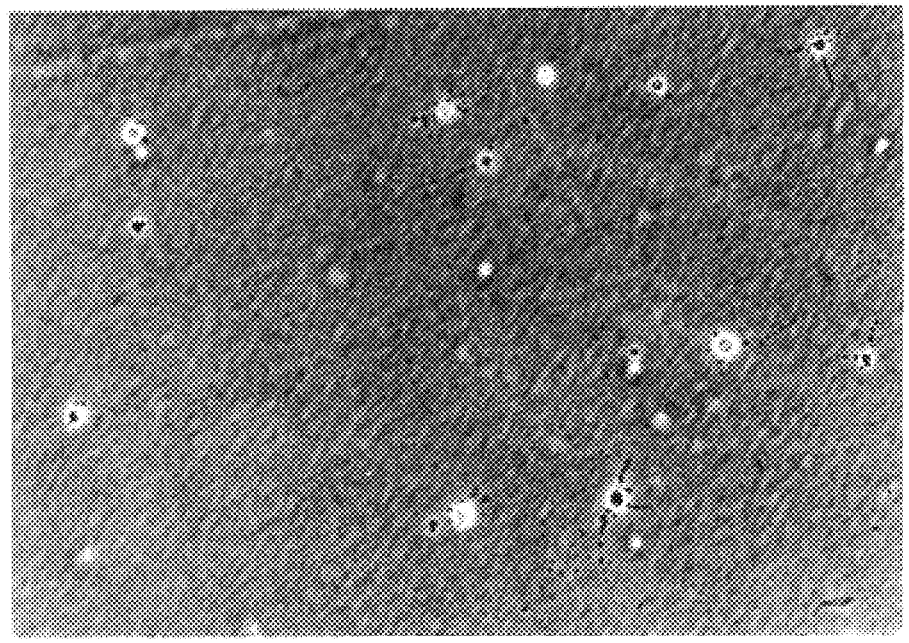
Figure 44B:
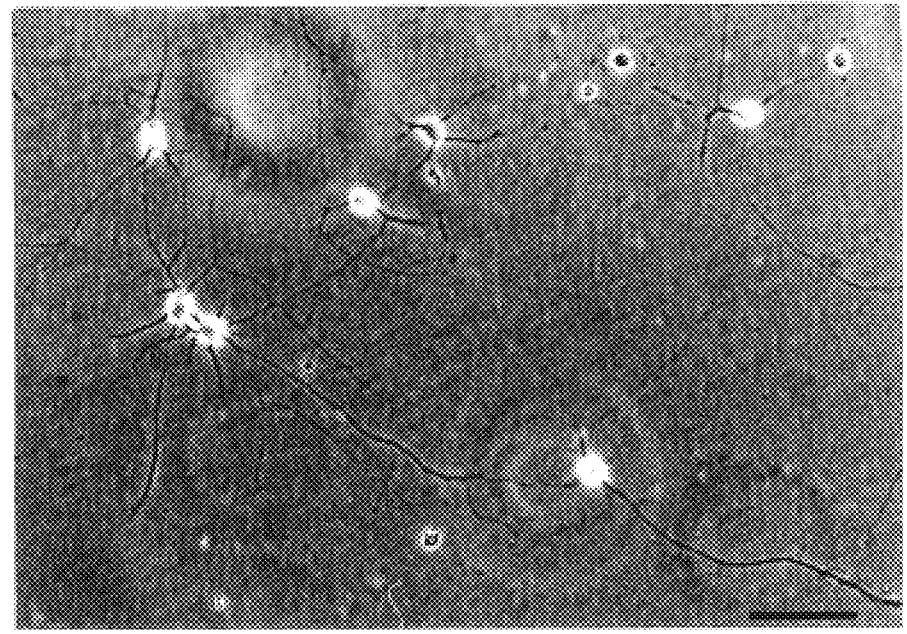

FIG. 44. Chick embryonic spinal motorneurons after 6 days in culture in the absence (A) or in the presence (B) of recombinant rat CNTF, 1 ng/ml. Scale bar=100 $\mu$m.

Figure 45A:
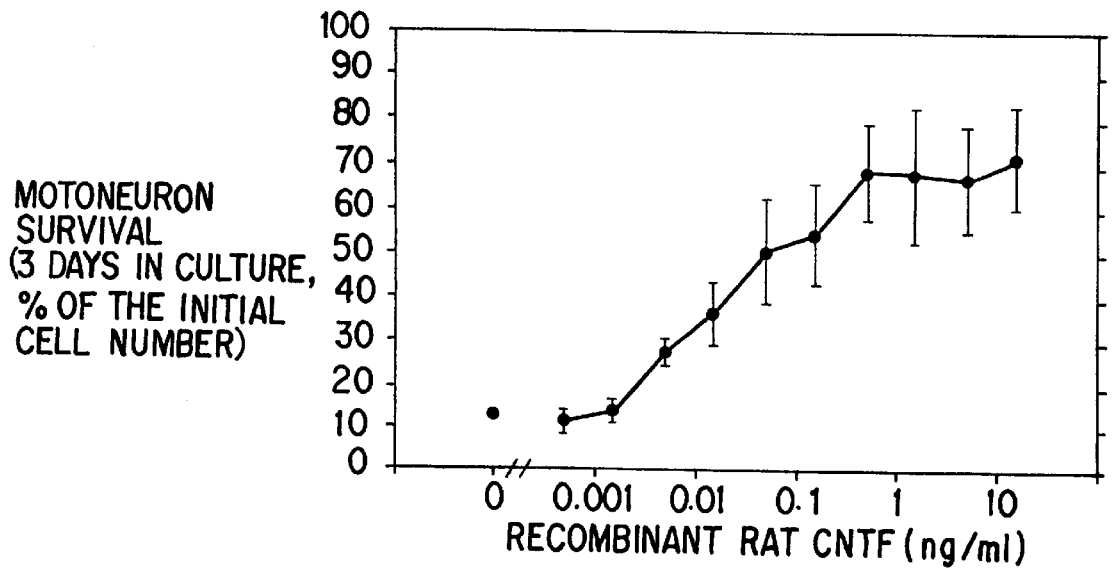
Figure 45B:
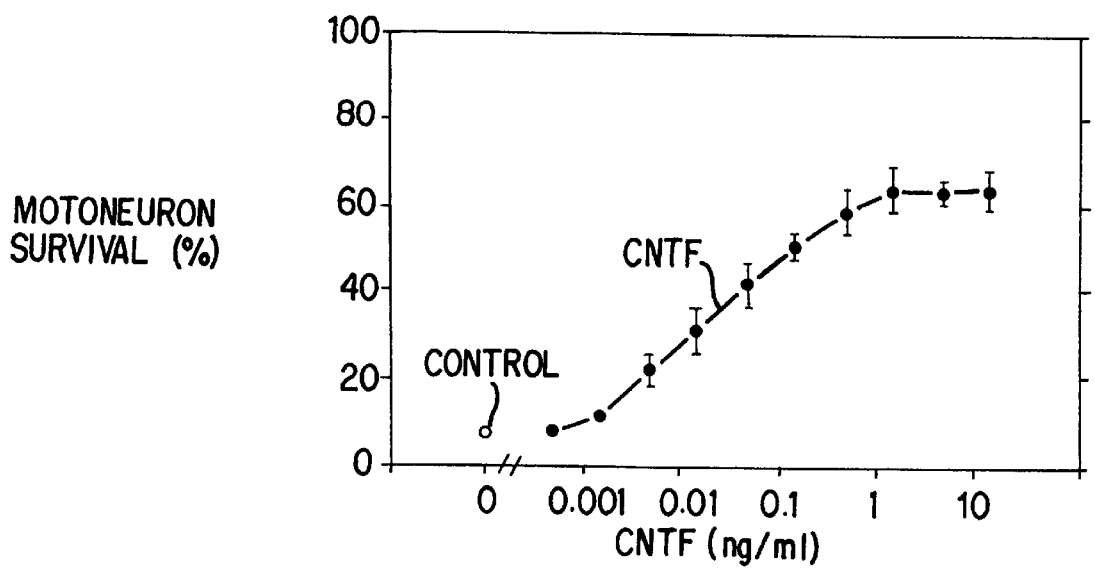
Figure 45C:
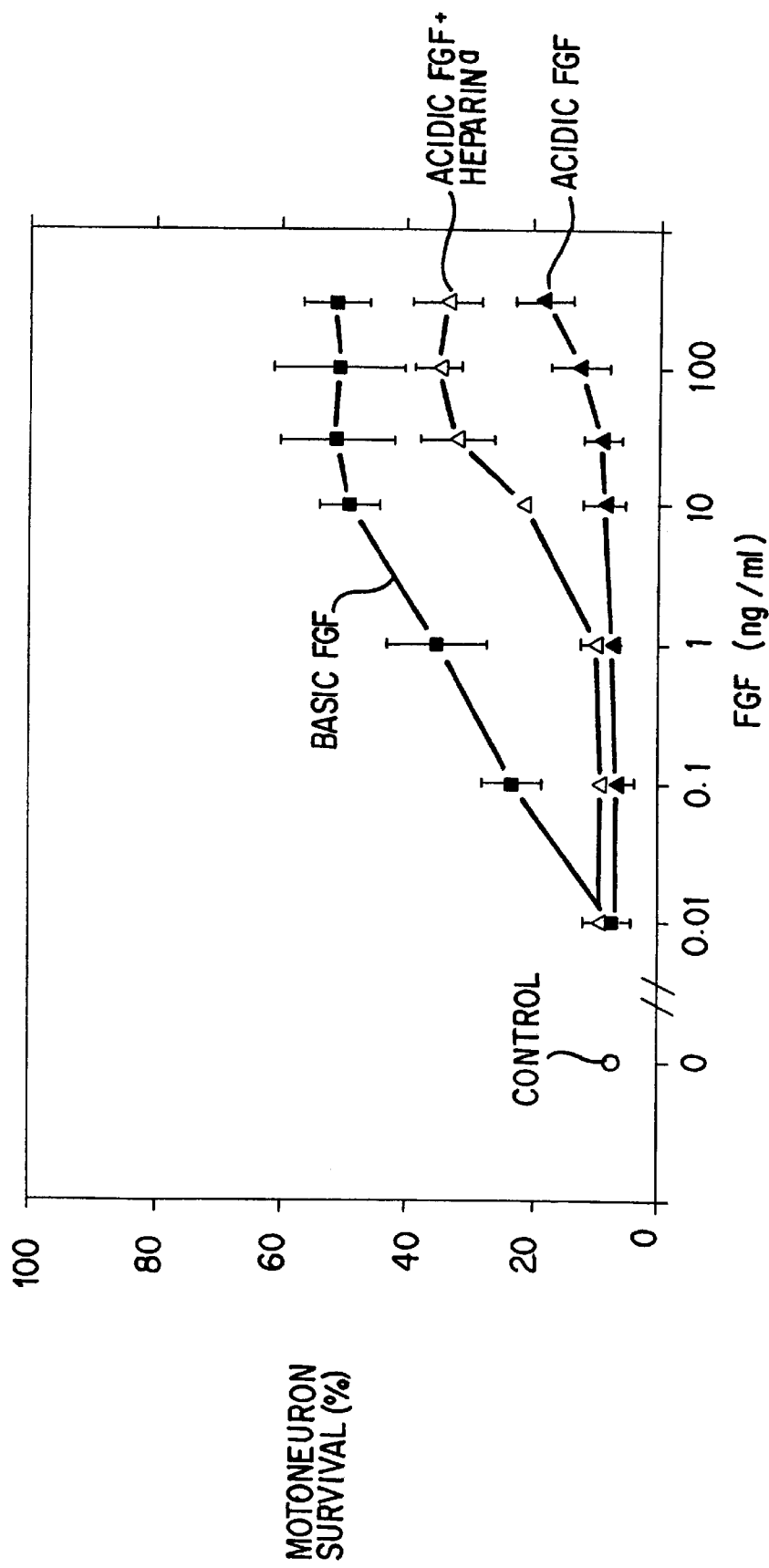

FIG. 45. Survival activity of recombinant rat CNTF for chick embryonic spinal motorneurons in culture (A) and concentration-response curves for CNTF (B) and FGFs (C). Survival activities were assayed after 3 days in culture. a in B, Heparin (1 $\mu$g/ml) was added to the culture only for the first 24 hr to avoid cell detachment induced by excess heparin, while acidic FGF was present for 3 days.

FIG. 46. Protein-coding portion of rat CNTF cDNA as compared with human sequences. Differences in deduced amino acid sequence are marked with an asterisk (*); differences in DNA sequences are indicated by a not equal sign (≠).

5. DETAILED DESCRIPTION OF THE INVENTION

The present invention relates to nucleic acid sequences encoding ciliary neurotrophic factor (CNTF) as well as CNTF proteins, peptide fragments, and derivatives produced in quantity therefrom. In addition, the invention relates to pharmacologic compositions and therapeutic and diagnostic uses of ciliary neurotrophic factor.

For purposes of clarity of description, and not by way of limitation, the invention will be described in the following parts.

i) Purification of CNTF
ii) CNTF bioassays
iii) Sequencing of CNTF
iv) Cloning of CNTF-Encoding DNA
v) Expression of a CNTF Gene
vi) CNTF Genes and Proteins
vii) Generation of Anti-CNTF Antibodies
viii) Utility of the Invention

5.1. Purification of Ciliary Neurotrophic Factor

CNTF may be purified from any available source including, but not limited to, chick embryo eyes, sciatic nerve, and cardiac muscle using techniques known in the art.

For example, and not by way of limitation, CNTF may be prepared from chick embryo eyes according to the method described in Barbin et al. (1984, J. Neurochem. 43:1468–1478, which is incorporated by reference in its entirety herein). Briefly, choroid, iris-ciliary body, and adherent pigment epithelium, collectively referred to as CIPE, may be dissected from 15-day chick embryo eyes as described in Manthorpe et al. (1980, J. Neurochem. 34:69–75) and collected in balanced salt solution. Preferably, extracts are derived from about three hundred embryo eyes which are homogenized in about 76 ml of cold water using a Teflon glass homogenizer and then centrifuged at $10^5$×g for one hour at about 4° C. The supernatant may then be collected and made 0.01 M in $NaH_2PO_4$, pH7, and then applied to an ion exchange column (i.e. Whatman DE52 cellulose equilibrated in phosphate buffer). The column may then be eluted at a flow rate of about 30 ml/hour with 20 ml each of 0.07, 0.25, and 0.5 M NaCl in phosphate buffer. The 0.25 M NaCl eluate may then be concentrated to a volume of about 2 ml by ultrafiltration (e.g., using a 50 ml Amicon cell and PM10 (10,000 dalton cutoff) ultrafiltration membrane). The retentate may then be collected, combined with two 0.5 ml washes of the cell with 0.25 M NaCl buffer, and further concentrated to 0.4 ml (e.g. using a 3 ml Amicon cell and PM 10 filter). Purified extract may then be layered on sucrose gradients (e.g. 200 μl extact on to 4.6 ml 5–20% linear sucrose gradients) and then centrifuged (e.g. using an SW 65 rotor at 65,000 rpm for 15 hours at 4° C.). The 4.8 ml gradients may then be harvested in five fractions; fraction I (2 ml) fraction II (0.3 ml), fraction III (1.2 ml) fraction IV (0.3 ml) and fraction V (1.0 ml). Fraction III may then be made 0.1% in Triton X-100, and then concentrated to 0.2 ml using ultrafiltration as above.

For analytical gel electrophoresis, purified CNTF may be analyzed using a 15% resolving and 4.5% stacking slab SDS-polyacrylamide gel. Purified CNTF or molecular weight standards may be electrophoresed and the gel cut out and processed as follows: the polypeptides may be visualized without fixation by precipitating the protein-associated SDS during an incubation of the gel in 0.25 M KCl and recording the positions of the standards and CNTF bands. Lanes may then be fixed and stained with Coomassie blue. Other lanes may then be cut into slices, eluted by incubation with Triton X-100, and then the eluates may be assayed for CNTF activity.

Sciatic nerve extract may be fractionated through the same steps (DEAE ion-exchange chromatography, sucrose density gradient centrifugation and preparative SDS-PAGE) as those used for the purification of the chick eye CNTF (supra) except that, preferably, the following three modifications may be made to the procedure: (1) after loading the nerve extract, the DEAE ion-exchange column may be batch-eluted directly with 0.15 M NaCl (instead of washing with 0.07 M NaCl and eluting with 0.25 M NaCl); (ii) slices are cut from the 24 Kd region (instead of the 20 Kd region) of the preparative SDS gel; and (iii) the CNTF activity may eluted from individual gel slices by homogenization in 0.1% Triton X-100 detergent followed by incubation overnight at 4° C. (rather than electrophoretic elution overnight through urea gels). The Triton X-100 detergent may then be removed by incubating the supernatant with 100 μl suspension of Extractagel (Pierce Chemicals, Rockford, Ill.) beads for 2 h at 4° C. Protein concentration may then be determined according to any method known in the art.

Preferably, the methods above may be further modified as follows: Following elution from a preparative SDS-PAGE gel, CNTF may be purified to homogeneity and freed of SDS by reversed phase chromatography, using an FPLC or HPLC column which constitutes a biocompatible fluidic system contained within an inert column; in a most preferred embodiment, the FPLC column is a Bakerbond Gold C4 Widepore column (a 7.75 mm×10 cm column lined with gold and able to operate at a back pressure of 200–250 psi with 1.0 ml/min in an aqueous mobile phase), eluted with a 0 to 60 percent acetonitrile gradient. CNTF has been observed to elute as a single peak at 50–55 percent acetonitrile (See Section 6, infra). The single peak containing CNTF may be concentrated in a Speed Vac in which the air had been flushed out with an inert gas such as argon. The inert gas appears to be important in preventing loss of CNTF activity, which occurs upon oxidation of one or more of the methionine residues. CNTF appears to be most vulnerable to oxidation when it is no longer in solution.

Likewise, a ciliary neuron survival promoting activity may be prepared from cardiac tissue using heparin affinity chromatography, as described in Watters and Hendry (1987, J. Neurochem. 49:705–713, which is incorporated by reference in its entirety herein).

5.2. Ciliary Neurotrophic Factor Bioassays

Ciliary neurotrophic factor activity may be evaluated using any CNTF-sensitive in vivo or in vitro system known in the art. For example, and not by way of limitation, in vitro systems have been developed which measure CNTF activity by quantitating 24-hour survival of embryonic (E8) chick ciliary ganglion (CG) neurons in monolayer cultures.

For example, ciliary ganglia may be collected from E8 chick embryos, dissociated (yielding approximately 20,000 cells per ganglion) and then diluted in HEBM medium containing 20 percent horse serum as described in Varon et al. (1979, Brain Res. 173:29–45). About fifty microliters of cell suspension containing neurons (2,000 cells) may then be seeded into microliter dishes and putative CNTF activity may be added. Culture plates may then be maintained at 37° C. in 5% $CO_2$ for 24 hours, after which the cultures may be fixed by the addition of 200 μl 2 per cent glutaraldehyde in HEBM medium, and the number of surviving neurons may be determined visually by direct count under phase contrast microscopy.

5.3. Sequencing of Ciliary Neurotrophic Factor Protein

The CNTF protein may be sequenced directly or initially cleaved by any protease or other compound known in the art, including, but not limited to, *Staphylococcus aureus* V8, trypsin, and cyanogen bromide. Peptides may be sequenced by automated Edman degradation on a gas phase microsequencer according to the method of Hewick et al. (1981, J. Biol. Chem. 256:7990–7997) and Hunkapillar et al. (1983, Methods Enzymol. 91:399–417). Detection of phenylthiohydantoin amino acids may then be performed according to Lottspeich (1985, Chromatography 326:321–327). Overlapping fragments of amino acid sequence may be determined and used to deduce longer stretches of contiguous sequence.

5.4. Cloning of Ciliary Neurotrophic Factor-Encoding DNA

The purification of suitable amounts of CNTF protein from rat sciatic nerve to permit microsequencing made possible the cloning of a CNTF cDNA. A standard strategy for such cloning might be to generate a complementary oligonucleotide probe, based on a segment of known amino acid sequence, and to use this probe to screen cDNA libraries generated from tissue presumed to synthesize mRNA encoding CNTF. However, this strategy was rendered problematic because of the relatively low abundance of mRNA, and because the actual sequence of the CNTF peptides determined by microsequencing (FIG. 1) would have required in every case an unfavorably high degree of degeneracy in the oligonucleotide probes, in order to accommodate all of the possible codon choices for particular amino acid residues. The instant invention provides for the cloning of the gene by synthesis of cDNA, the derivation of a pair of degenerate oligonucleotide primers, based on the microsequencing of CNTF peptides, use of these primers to amplify a segment of the CNTF coding sequence, use of a third degenerate oligonucleotide to confirm the identity of the amplified segment, determination of the exact nucleotide sequence of that segment, and the synthesis and use of exact oligonucleotide primers to amplify the remainder of the CNTF gene. In this method of the invention, the preferred procedure for amplification utilizes the amplification of tissue nucleic acid sequences by polymerase chain reaction (PCR) (Saiki et al., 1985, Science 230:1350–1354). A detailed description of the preferred method follows:

First, the amino acid sequence derived from purified CNTF protein may be used to deduce oligonucleotide primers for use in PCR. Because of the degeneracy of the genetic code, in which several triplets may specify the same amino acid, several oligonucleotides should be synthesized for a given amino acid sequence, in order to provide for multiple potential nucleotide sequence combinations; the resulting oligonucleotides are referred to as degenerate primers.

PCR requires sense strand as well as anti-sense strand primers. Accordingly, a degenerate oligonucleotide primer corresponding to one segment of CNTF amino acid sequence may be used as primer for one DNA strand (e.g. sense), and another degenerate oligonucleotide primer, homologous to a second segment of CNTF amino acid sequence, may be used as primer for the second DNA strand (e.g. anti-sense). Preferably, these primers should be chosen based on a contiguous stretch of known amino acid sequence, so that the relevant DNA reaction product resulting from the use of these primers in PCR may be of a predictable size (i.e. the length of the product, in number of basepairs, should equal the sum of the lengths of the two primers plus three times the number of amino acid residues in the segment of protein bounded by the segments corresponding to the two primers). These primers may then be used in PCR with nucleic acid template presumed to contain CNTF encoding sequences, such as genomic DNA or, preferably, cDNA prepared from mRNA collected from tissue or cells presumed to synthesize CNTF. The DNA reaction products may then be analyzed by electrophoresis, to determine whether a DNA reaction product has a molecular size similar to that predicted. The DNA reaction products may be further analyzed by hybridization with a labeled probe prepared from a degenerate oligonucleotide corresponding to amino acid sequences between the segments of the two primers used for PCR. Sequence analysis of the DNA reaction product of the predicted size may be compared to the ascertained amino acid sequence to corroborate that the amplified nucleic acid sequence may, in fact, encode the CNTF peptide fragment. Although any method of nucleic acid sequencing known in the art may be utilized, it is preferable to use the dideoxynucleotide chain termination method (Sanger et al., 1979, Proc. Natl. Acad. Sci. U.S.A. 72:3918–3921). Sequencing may be accomplished using gel purified or, preferably, cloned DNA reaction product. A "tail" containing known target sequences for selected restriction endonucleases may be incorporated at the 5' end of each oligonucleotide primer utilized for PCR, in order to facilitate cloning of DNA reaction products.

The sequence of the DNA reaction product may then be used toward designing an oligonucleotide primer corresponding to exact CNTF-encoding sequence. This primer may then be used together with a second primer in PCR to extend the amount of CNTF-encoding sequence beyond that represented by the fragment of exact sequence initially determined. For example, and not by way of limitation, the protocol for "rapid amplification of cDNA ends" (RACE) (M. A. Frohman, M. K. Dush, G. R. Martin, 1988, Proc. Natl. Acad. Sci. U.S.A. 85:8998–9002) may be used to clone segments from within the region of known exact sequence to the 5' and 3' ends of CDNA molecules, respectively. Thus, in order to obtain a clone extending to the 3' end, the sense strand primer may correspond to exact CNTF nucleotide sequence, whereas the anti-sense strand primer may be homologous to a segment of known sequence likely to be found downstream of the sequenced fragment, e.g. the 3' polyadenosine tail of mRNA, as reverse transcribed in the cDNA; the primer in this case would include a stretch of oligo-dT. It may then be necessary to use a similar method to retrieve sequence upstream of the sequenced fragment; for example, the anti-sense strand primer may correspond to exact CNTF nucleotide sequence and the sense strand primer ay be homologous to a region upstream of the sequenced fragment, e.g. a 5' polyguanosine tail added at the 5' end of cDNA using terminal deoxynucleotide transferase (the primer in this case would include a stretch of oligo-dC).

The amplified fragments may then be sequenced, or, preferably, cloned and then sequenced. Once exact oligonucleotides from the 5' and 3' ends of the cDNA have been determined, the exact nucleotides may then be used in PCR reaction to obtain the intervening nucleic acid sequences, and the products of the PCR reaction may then be cloned.

DNA reaction products may be cloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or BLUESCRIPT® (Stratagene) plasmid derivatives. Recombinant molecules can be introduced into host cells via transformation, transfection, infection, electroporation, etc.

The CNTF gene is inserted into a cloning vector which can be used to transform, transfect, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. It may prove advantageous to incorporate restriction endonuclease cleavage sites into the oligonucleotide primers used in polymerase chain reaction to facilitate insertion into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and CNTF gene may be modified by homopolymeric tailing.

In specific embodiments, transformation of host cells with recombinant DNA molecules that incorporate an isolated CNTF gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

According to a preferred embodiment of the invention, once a cDNA-derived clone encoding CNTF has been generated, a genomic clone encoding CNTF may be isolated using standard techniques known in the art. For example, a labeled nucleic acid probe may be derived from the CNTF clone, and used to screen genomic DNA libraries by nucleic acid hybridization, using, for example, the method set forth in Benton and Davis (1977, Science 196:180) {Both the DNA and phage are denatured and fixed in situ by dipping the filters in 0.1 N NaOH and 1.5 M NaCl for 20 seconds; the filters are then neutralized by dipping in 0.2 M tris, pH 7.5, and 2×SSCP (standard saline citrate phosphate buffer (SSCP) is (1×) 120 mM NaCl, 15 mM sodium citrate, 13 mM $KH_2PO_4$, 1 mM EDTA, titrated to pH 7.2 with NaOH) for 20 seconds. Filters are blotted and baked at 80° C. in a vacuum for 1.5 to 2 hours. Hybridization to the nitrocellulose replicas is carried out in a siliconized glass petri dish. The $^{32}$P-labeled probe ($10^5$ to $10^6$ counts per minute per filter) is placed in enough 5×SSCP and 50 percent formamide to cover all filters. The hybridization mixtures were usually incubated for 12 to 18 hours. Buffer and probe can be recovered and reused for at least 2 weeks. After hybridization, the filters are washed in a large (10 to 15 ml per filter) volume of 5×SSCP and 50 percent formamide at 42° C. for 30 minutes and then for 20 to 30 minutes in 2×SSCP at room temperature.} for bacteriophage libraries and Grunstein and Hogness (1975, Proc. Natl. Acad. Sci. U.S.A. 72:3961–3965) {The dry filter is moistened with a 5×SSC, 50% formamide solution containing the labeled RNA, using 10–15 $\mu$l/cm$^2$ of filter. The filter is covered with mineral oil, incubated for 16 hr at 37° allow hybridization, and then washed for 10 min in a beaker containing chloroform that is gently agitated on a shaking platform. Two more identical chloroform washes are followed by 10 min washes in 6×SSC, 2×SSC, and 2×SSC containing 20 $\mu$g/ml of pancreatic ribonuclease.} for plasmid libraries. Retrieved clones may then be analyzed by restriction-fragment mapping and sequencing techniques according to methods well known in the art.

Furthermore, additional cDNA clones may be identified from a cDNA library using the sequences obtained according to the invention.

5.5. Expression of a Ciliary Neurotrophic Factor Gene

The nucleotide sequence coding for a CNTF protein, or a portion thereof, can be inserted into an appropriate expression vector, i.e., a vector which contains the necessary elements for the transcription and translation of the inserted protein-coding sequence. The necessary transcriptional and translation signals can also be supplied by the native CNTF gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding CNTF protein or peptide fragment may be regulated by a second nucleic acid sequence so that CNTF protein or peptide is expressed in a host transformed with the recombinant DNA molecule. For example, expression of CNTF may be controlled by any promoter/enhancer element known in the art. Promoters which may be used to control CNTF expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 30 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing CNTF gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted CNTF gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the CNTF gene is inserted within the marker gene sequence of the vector, recombinants containing the CNTF insert can be identified by the absence of the marker gene function. In the third approach, recombinant expression vectors can be identified by assaying the foreign gene product expressed by the recombinant. Such assays can be based, for example, on the physical or functional properties of the CNTF gene product in bioassay systems as described supra, in Section 5.2.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered CNTF protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous CNTF protein. Furthermore, different vector/host expression systems may effect processing reactions such as proteolytic cleavages to different extents.

In a specific embodiment of the invention, DNA encoding CNTF may be cloned into pCMV plasmid, amplified, and then used to transform HeLa cells by the DEAE-dextran method; CNTF activity may then be collected from cell extracts (see Example Section 6, infra).

In another specific embodiment of the invention, DNA encoding CNTF may be incorporated into an appropriate expression vector and used to transform E. coli, resulting in biologically active CNTF (see Example Section 7, infra).

In particular embodiments of the invention expression of CNTF in E. coli is preferably performed using vectors which comprise one of the following: a lac UV5 promoter which may be controlled by the lactose operon repressor; a strong ribosome binding site, for example, the ribosome binding site of bacteriophage T7; a mutation in the replication control region of the plasmid which may increase copy number; or a mutation which limits the expression of the antibiotic resistance protein. In a preferred specific embodiment of the invention, expression of CNTF is performed using the vector pRPN12, which may result in a 30 to 50 fold increase in expression of CNTF relative to other vectors (Section 12, infra). In another preferred embodiment of the invention expression vector pRPN38 may be used to produce CNTF in E. coli. In other preferred embodiments of the invention, human CNTF may be expressed in E. coli using the vector pRPN40. The invention also provides for molecules which are functionally equivalent to plasmids pRPN12, pRPN38, pRPN39 and pRPN40 which comprise equivalent elements (promoter, ribosome binding site, etc.) which result in comparable levels of expression of CNTF.

5.5.1. Identification and Purification of the Expressed Gene Product

Once a recombinant which expresses the CNTF gene is identified, the gene product should be analyzed. This can be achieved by assays based on the physical or functional properties of the product.

Once the CNTF protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any known CNTF assay, including, but not limited to, chick embryo ciliary ganglion neurons.

Importantly, methods used to prepare CNTF from sciatic nerve tissue, because they involve, as a final step, preparative gel electrophoresis, would produce CNTF which may not be fully active due to the presence of residual SDS. In contrast, the present invention provides a method of purifying CNTF with optimal biological activity and which is suitable for protein sequencing, using an FPLC column; the present invention also permits the isolation of recombinant CNTF which is produced from recombinant nucleic acid molecules or chemically synthesized and which is therby free of SDS and fully active.

5.6. Ciliary Neurotrophic Factor Genes and Proteins

Using the methods detailed supra and in Example Sections 6 and 8, infra, the following nucleic acid sequences were determined, and their corresponding amino acid sequences deduced. The rat CNTF cDNA sequence was determined, and is depicted in FIG. 1. Human genomic CNTF sequence was determined, and is depicted in FIG. 8. Each of these sequences, or their functional equivalents, can be used in accordance with the invention. Additionally, the invention relates to CNTF genes and proteins isolated from porcine, ovine, bovine, feline, avian, equine, or canine, as well as primate sources and any other species in which CNTF activity exists. The invention is further directed to subsequences of CNTF nucleic acids comprising at least ten nucleotides, such subsequences comprising hybridizable portions of the CNTF sequence which have use, e.g., in nucleic acid hybridization assays, Southern and Northern blot analyses, etc. The invention also provides for CNTF proteins, fragments and derivatives thereof, according to the amino acid sequences set forth in FIGS. 1 and 8 or their functional equivalents. The invention also provides fragments or derivatives of CNTF proteins which comprise antigenic determinant(s) or which are functionally active. As used herein, functionally active shall mean having positive activity in assays for known CNTF function, e.g. chick embryo ciliary ganglion-assays.

For example, the nucleic acid sequences depicted in FIGS. 1 and 8 can be altered by substitutions, additions or deletions that provide for functionally equivalent molecules. Due to the degeneracy of nucleotide coding sequences, other DNA sequences which encode substantially the same amino acid sequence as depicted in FIGS. 1 and 8 may be used in the practice of the present invention. These include but are not limited to nucleotide sequences comprising all or portions of the CNTF genes depicted in FIGS. 1 and 8 which are altered by the substitution of different codons that encode a functionally equivalent amino acid residue within the sequence, thus producing a silent change. Likewise, the CNTF proteins, or fragments or derivatives thereof, of the invention include, but are not limited to, those containing, as a primary amino acid sequence, all or part of the amino acid sequence substantially as depicted in FIGS. 1 and 7 including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are CNTF proteins or fragments or derivatives thereof which are differentially modified during or after translation, e.g., by glycosylation, proteolytic cleavage, linkage to an antibody molecule or other cellular ligand, etc. Section 8, infra exemplifies the expression of biologically active recombinant CNTF in E. coli, thereby indicating that non-glycosylated CNTF is biologically active.

In addition, the recombinant CNTF encoding nucleic acid sequences of the invention may be engineered so as to modify processing or expression of CNTF. For example, and not by way of limitation, a signal sequence may be inserted upstream of CNTF encoding sequences to permit secretion of CNTF and thereby facilitate harvesting or bioavailability.

Additionally, a given CNTF can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TAB® linkers (Pharmacia), etc.

5.7. Generation of Anti-Ciliary Neurotrophic Factor Antibodies

According to the invention, CNTF protein, or fragments or derivatives thereof, may be used as immunogen to generate anti-CNTF antibodies. By providing for the production of relatively abundant amounts of CNTF protein using recombinant techniques for protein synthesis (based upon the CNTF nucleic acid sequences of the invention), the problem of limited quantities of CNTF has been obviated.

To further improve the likelihood of producing an anti-CNTF immune response, the amino acid sequence of CNTF may be analyzed in order to identify portions of the molecule which may be associated with increased immunogenicity. For example, the amino acid sequence may be subjected to computer analysis to identify surface epitopes, as illustrated by FIGS. 15(a) and (b), which present computer-generated plots of hydrophilicity, surface probability, flexibility, antigenic index, amphiphilic helix, amphiphilic sheet, and secondary structure of rat and human CNTF, respectively. Alternatively, the deduced amino acid sequences of CNTF from different species could be compared, and relatively non-homologous regions identified; these non-homologous regions would be more likely to be immunogenic across various species.

For preparation of monoclonal antibodies directed toward CNTF, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of CNTF. For the production of antibody, various host animals can be immunized by injection with CNTF protein, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, *Corynebacterium parvum*.

A molecular clone of an antibody to a CNTF epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be.generated by reducing the disulfide bridges of the $F(ab')_2$ fragment, and the 2 Fab or Fab fragments which can be generated by treating the antibody molecule with papain and a reducing agent.

Example Section 9 describes the preparation of polyclonal antisera directed toward a fourteen amino acid peptide fragment of CNTF protein.

Example Section 17 describes four anti-CNTF monoclonal antibodies that are provided for by the present invention, namely RP3-12, RP12-1, RP12-2, and RP12-9.

5.8. Utility of the Invention

The present invention relates to the nucleic acid sequence of CNTF and to substantially pure proteins, peptide fragments, or derivatives produced therefrom. CNTF proteins, peptides, and derivatives, anti-CNTF antibodies, and CNTF nucleic acid probes, may be utilized in diagnostic and therapeutic applications. For most purposes, it is preferable to use CNTF genes or gene products from the same species for diagnostic or therapeutic purposes, although cross-species utility of CNTF may be useful in specific embodiments of the invention.

5.8.1. Diagnostic Applications

The present invention, which relates to nucleic acids encoding CNTF and to proteins, peptide fragments, or derivatives produced therefrom, as well as antibodies directed against CNTF protein, peptides, or derivatives, may be utilized to diagnose diseases and disorders of the nervous system which may be associated with alterations in the pattern of CNTF expression.

In various embodiments of the invention, CNTF genes and related nucleic acid sequences and subsequences, including complementary sequences, may be used in diagnostic hybridization assays. The CNTF nucleic acid sequences, or subsequences thereof comprising at least about 10 nucleotides, can be used as hybridization probes. Hybridization assays can be used to detect, prognose, diagnose, or monitor conditions, disorders, or disease states associated with changes in CNTF expression, including, in particular, conditions resulting in damage and degeneration of neurons known to respond to CNTF, such as parasympathetic neurons, cholinergic neurons, spinal cord neurons, neuroblastoma cells and cells of the adrenal medulla. Such diseases and conditions include but are not limited to CNS trauma, infarction, infection, degenerative nerve disease, malignancy, or post-operative changes including but not limited to Alzheimer's Disease, Parkinson's Disease, Huntington's Chorea, and amyotrophic lateral sclerosis. For example, total RNA in a tissue sample from a patient can be assayed for the presence of CNTF mRNA, wherein the decrease in the amount of CNTF mRNA is indicative of neuronal degeneration.

In alternate embodiments of the invention, antibodies directed toward CNTF protein, peptide fragments, or derivatives can be used to diagnose diseases and disorders of the nervous system, including, in particular, those neuronal populations and clinical disorders and diseases listed supra. Antibodies directed toward CNTF proteins of the invention can be used, for example, for immunohistochemical identification of CNTF activity in tissue section or biopsy from a patient in need of such evaluation. In a further example, the antibodies of the invention can be used in ELISA procedures to detect and/or measure amounts of CNTF present in tissue or fluid samples; similarly, the antibodies of the invention can be used in Western blot analysis to detect and/or measure CNTF present in tissue or fluid samples. An antibody of the invention which binds and immunoprecipitates CNTF is described in Section 11, infra.

In further embodiments of the invention, CNTF protein, peptide fragments or derivatives can be used to diagnose diseases and disorders of the nervous system. In a particular embodiment and not by way of limitation, labeled CNTF protein or peptide fragments can be used to identify tissues or cells which express the CNTF receptor in order to identify aberrancies of CNTF receptor expression and consequently, potential abnormalities in the tissue or cellular response to CNTF.

The present invention also provides for an immunological assay for measuring the amount of CNTF in a liquid sample which is a two antibody anti-mouse anti-IgG noncovalently attached to sandwich method comprising binding a first anti-CNTF antibody to a solid support, exposing the bound first antibody to a solution which comprises CNTF under conditions which permit the binding of first antibody to CNTF to occur, and then exposing the CNTF bound to the first antibody to a second anti-CNTF antibody which preferably is directed to a different CNTF epitope than the first anti-CNTF antibody, under conditions which permit the binding of CNTF to second antibody to occur, and then detecting the binding of second antibody to CNTF using techniques known in the art, including, but not limited to, binding second antibody to an anti-immunoglobulin antibody conjugated to an indicator substance such as a flourescent compound, or a compound comprising radioisotope, or an enzyme, or a substance than can produce a signal in a calorimetric assay. In a preferred embodiment of the invention, monoclonal antibodies RP3-12 and RP12-2 may be utilized in such a two antibody sandwich assay for human CNTF (see Section 17, infra). Such a technique may be used as a sensitive assay for measuring levels of CNTF, and may be used in the diagnosis of neurologic disorders associated with abnormalities in CNTF expression.

5.8.2. Therapeutic Applications

The present invention, which relates to nucleic acids encoding CNTF, and to proteins, peptide fragments, or derivatives produced therefrom, as well as to antibodies directed against CNTF protein, peptides, or derivatives, may be utilized to treat diseases and disorders of the nervous system which may be associated with alterations in the pattern of CNTF expression or which may benefit from exposure to CNTF or anti-CNTF antibodies.

In various embodiments of the invention, CNTF protein, peptide fragments or derivatives can be administered to patients in whom the nervous system has been damaged by trauma, surgery, ischemia, infection (e.g. polio or A.I.D.S.), metabolic disease, nutritional deficiency, malignancy, toxic agents or degenerative disease of as yet unknown origin. In various specific embodiments of the invention, CNTF can be administered to spinal cord neurons which have been damaged, for example, by trauma, infarction, infection, degenerative disease or surgical lesion; Example Section 10 illustrates the use of CNTF in promoting the survival of spinal cord neurons.

The CNTF nucleic acids, peptides, and derivatives of the present invention may be used to treat disorders of motorneurons. Example Section 11 illustrates the remarkable effectiveness of CNTF in promoting the survival of motorneurons in severed facial nerve. Accordingly, in particular embodiments of the invention, CNTF, or peptides or derivatives therefrom, may be used to treat Bell's palsy or other (a paralyses involving the facial nerve) as well as other diseases of the motor system (Motor Neuron Diseases), including, but not limited to, amyotrophic lateral sclerosis, progresive spinal muscular atrophy, progressive bulbar paralysis, primary lateral sclerosis, and spinal muscular atrophies (Werdning-Hoffman disease and Kugelberg-Welander disease), and Post-Polio Syndrome.

Degeneration and death of motorneurons in the ventral horn of the spinal cord is a major aspect of the pathophysiologic process in amyotrophic lateral sclerosis (ALS; Lou Gehrig's disease), spinal cord injury, and related diseases. The result of Sections 10 and 14, infra show that CNTF may be used to enhance survival and promote cholinergic expression in spinal cord motorneurons in treating these diseases.

In addition, as supported by data presented in Example section 18, infra, pharmaceutical compositions comprising basic fibroblast growth factor or, most preferably, CNTF and basic fibroblast growth factor, may be used to promote the survival of motorneurons and used in the treatment of the abovementioned motorneuron diseases.

The present invention can also be used, for example, in hastening the recovery of patients suffering from diabetic neuropathies, e.g. mononeuropathy multiplex or impotence. In further embodiments of the invention, CNTF protein or peptide fragments or derivatives derived therefrom, can be used to treat congenital conditions or neurodegenerative disorders, including, but not limited to, Alzheimer's disease, aging, peripheral neuropathies, Parkinson's disease, Huntington's chorea and diseases and disorders of motorneurons; in particular, the invention can be used to treat congenital or neurodegenerative disorders associated with cholinergic neuron dysfunction. Alzheimer's disease has been shown to involve selective loss of cholinergic neurons in the basal forebrain, and it has been shown that approximately 35 per cent of patients with Parkinson's disease suffer from Alzheimer-type dementia; CNTF produced according to the invention may prove to be useful single agent therapy for this disease complex. Similarly, CNTF produced according to the invention may be used therapeutically to treat Alzheimer's disease in conjunction with Down's Syndrome. CNTF produced according to the invention can be used in the treatment of a variety of dementias as well as congenital learning disorders.

As exemplified in Section 15, infra, CNTF has been observed to exhibit a number of activities on hippocampal cells, including increased GABA uptake, increased expression of neurofilament protein and GAD enzyme, increased survival of GABAergic neurons and, increased survival of hippocampal neurons. Accordingly, in various embodiments of the invention, CNTF may be used to exert these activites on hippocampal cells in vitro or in vivo, and may be used in the treatment of neurologic disorders involving the hippocampus, including but not limited to Alzheimer's disease, infarction, and toxic injuries.

The CNTF, CNTF peptides, antibodies or derivatives of the invention may also be used to treat tumors originating from nervous system tissue, including glioblastoma and melanoma, which arises from neural crest derived melanocytes.

It may be desirable to administer the CNTF-related peptides or CNTF protein by adsorption onto a membrane, e.g. a silastic membrane, gel, or foam that could be implanted in the proximity of the damaged nerve. In a specific embodiment of the invention, administration of CNTF protein, peptide fragments or derivatives can be used in conjunction with surgical implantation of tissue or other sustained release compositions, including microspheres, microcapsules, or synthetic implants, in the treatment of Alzheimer's disease, amyotrophic lateral sclerois and other motorneuron diseases (including, for example, Werdnig-Hoffman disease), and Parkinson's disease.

In further embodiments of the invention, CNTF protein, fragments or derivatives can be used in conjunction with other cytokines to achieve a desired neurotrophic effect. For example, and not by way of limitation, according to the invention CNTF can be used together with NGF to achieve a stimulatory effect on growth and survival of neurons. It is envisioned that CNTF may function synergistically with other CNS-derived peptide factors yet to be fully characterized, in the growth, development, and survival of a wide array of neuronal subpopulations in the central and peripheral nervous system.

It is further envisioned that, based on the full characterization of the CNTF molecule, novel peptide fragments, derivatives, or mutants of CNTF may be developed which are capable of acting as agonists or antagonists of some, or all of the biological functions of CNTF.

In still further embodiments of the invention, antibodies directed toward CNTF protein, or peptide fragments or derivatives thereof, can be administered to patients suffering from a variety of neurologic disorders and diseases and who are in need of such treatment. For example, patients who suffer from excessive production of CNTF may be in need of such treatment. Anti-CNTF antibodies can be used in prevention of aberrant regeneration of sensory neurons (e.g. post-operatively), or in the treatment of chronic pain syndromes.

5.8.3. Pharmaceutical Compositions

The active compositions of the invention, which may comprise all or portions of the CNTF gene product, including protein, peptide fragments or derivatives produced therefrom, or antibodies (or antibody fragments) directed toward CNTF protein, peptide fragments, or derivatives, or a combination of CNTF and a second agent, such as NGF may be administered in any sterile biocompatible pharmaceutical carrier, including, but not limited to, saline, buffered saline, dextrose, and water.

CNTF protein, peptide fragment or derivative may comprise an amino acid sequence or subsequence thereof substantially as depicted in FIG. 1 (rat) or FIG. 8 (human sequence). CNTF may be derived from sequences corresponding to the CNTF genes of any suitable species, including, but not limited to, human, pig, rat, chicken, cow, dog, sheep, goat, cat, rabbit, etc.

The amount of CNTF protein, peptide fragment, derivative, or antibody which will be effective in the treatment of a particular disorder or condition will depend on the nature of the disorder or condition, and can be determined by standard clinical techniques. Where possible, it is desirable to determine the dose-response curve of the pharmaceutical compositions of the invention first in vitro, e.g. in the CNTF bioassay systems described supra, and then in useful animal model systems prior to testing in humans. Based on in vitro data, in a specific embodiment of the invention, a pharmaceutical composition effective in promoting the survival of ciliary ganglion neurons may provide a local CNTF protein concentration of about 2 μg/ml. In an additional specific embodiment of the invention, a pharmaceutical composition effective in promoting the growth and survival of cholinergic neurons may provide a local CNTF protein concentration of about 40 trophic units per milliliter.

Methods of introduction include but are not limited to intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

Further, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers.

The invention also provides for pharmaceutical compositions comprising CNTF proteins, peptide fragments, or derivatives administered via liposomes, microparticles, or microcapsules. In various embodiments of the invention, it may be useful to use such compositions to achieve sustained release of CNTF and CNTF-related products.

It is envisioned that it may be possible to introduce cells actively producing CNTF, CNTF related substances, CNTF-antagonists, or CNTF-agonists, anti-CNTF antibodies into areas in need of increased or decreased concentrations of CNTF.

5.8.4. Molecular Probes of the Invention May be Used to Identify Novel CNTF-Homologous Molecules Molecules exhibiting CNTF-like activity but differing in their molecular weights have been identified among various species and tissues, including chick embryo eye, rat sciatic nerve, damaged brain tissue, cardiac cells, neuroblastoma cell supernatants (Heymanns and Unsicker, 1987, Proc. Natl. Acad. Sci. U.S.A. 84:7758–7762) and adrenal medullary cells (Unsicker et al., 1985, Neurosci. Lett. 60:127–132). It is not known how many of these are identical to or distinct from the CNTF described here; additional sources and species of CNTF are likely to be found. The recombinant DNA molecules of the invention, or antibodies directed to CNTF proteins or peptide fragments of the invention, may be used to characterize novel CNTF-homologous molecules.

For example, and not by way of limitation, the CNTF encoding recombinant DNA molecules may be used as probes to identify novel molecules that are homologous with but not identical to the CNTF molecules depicted in FIGS. 1 and 8. These homologous molecules may or may not exhibit CNTF activity, and may arise from the same or different genomic sequences relative to molecules set forth in FIGS. 1 and 8. Preferably, these novel molecules could be identified using portions of the CNTF-encoding sequences set forth in FIGS. 1 or 8 as oligonucleotide primers in PCR reactions using, as template, either genomic DNA or RNA from the cells believed to express the CNTF-homologue. Likewise, anti-CNTF antibodies could be used to precipitate polysomes synthesizing CNTF homologous proteins; the RNA so collected could then be subjected to PCR amplification using the oligonucleotide primers of the invention. Using this technique, it is believed that a number of CNTF-related molecules may be identified and cloned.

6. EXAMPLE: MOLECULAR CLONING, EXPRESSION AND REGIONAL DISTRIBUTION OF RAT CILIARY NEUROTROPHIC FACTOR (CNTF)

6.1. Materials and Methods

6.1.1. Purification and Cleavage of CNTF

CNTF was purified as described (Saadat, et al., 1989, J. Cell Biol, 108: 1807–1816): Additionally, after electroelution from preparative polyacrylamide gels CNTF was applied to a 7.75×100 mm Bakerbond Gold C4 Widepore column and eluted with 0.1% trifluoracetic acid and a 0 to 60 percent gradient of acetonitrile. The biologically active protein eluted in one peak at 50 to 55% acetonitrile. 2D-gel analysis of 4 μg of purified CNTF, in which the first dimension consisted of isoelectric focusing on a gradient of pH 3.5–10.0 and the second dimension consisted of 12% SDS polyacrylamide gel electrophroesis, showed that this protein migrated as a single spot (Saadat et al., 1989, J. Cell Biol. 108:1807–1816) (FIG. 2). 2D-gel analysis of CNTF which was not subjected to the additional step of purification on the Bakerbond Gold C4 Widepore column was run in parallel.

The single peak containing CNTF was concentrated in a Speed Vac in which the air had been flushed out with argon. The argon was found to be important in preventing loss of CNTF activity, which occurs upon oxidation of one or more of the methionine residues. For BRCN-cleavage, formic acid (final concentration 70% v/v) and BRCN (10% v/v) were added to 30 μg of purified CNTF. After 3 h at room temperature, 500 μl of $H_2O$ were added and the material was concentrated to 50 μl and applied immediately to the Bakerbond Gold C4 Widepore column. For tryptic cleavage, 30 μg of chromatography-purified CNTF were dried, redissolved in 50 μl of 0.1 M TRIC/HCL (pH 8.0) containing 10 mM CaCl$_2$ and 3 µg TPK-treated trypsin (Sigma), and incubated overnight at 37°. The resulting fragments were loaded on the Bakerbond Gold C4 Widepore column and eluted using the same conditions (flow rate 1 ml/min$^{-1}$, gradient 0–60% acetonitrile in 60 minutes, monitoring at 214 nm). Peaks were collected manually. The amino acid sequences of the peptides were determined by use of an automated Applied Biosystems sequencer (Eckerskorn et al., 1988, Electrophoresis, 9:830–838).

The amino acid composition of purified CNTF was determined by hydrolysis of 5 µg of CNTF and derivatisation with ninhydrin (Tsugita et al., 1987, Biochem., 102:1593–1597).

6.1.2. Generation of cDNA CNTF Clones cDNA was synthesized from total RNA of cultured rat astrocytes (Okayama et al., 1987, Methods Enzymol. 154:3–29) using oligo primer 5 (oligonucleotide primers are presented in FIG. 1C) and reverse transcriptase (Bethesda Research Laboratories). The first strand of cDNA served as a template for amplification of specific segments of CNTF using PCR (Saiki et al., 1988, Science, 239:487–491). Clone A was generated using the degenerate primer-oligos 1 and 2, and the PCR product was identified with oligo 11, subcloned and sequenced. The sequence of this partial clone was used to synthesize primers 3 and 4 for amplification of cDNA ends (RACE) according to described methods (Frohmann et al., 1988, Proc. Natl. Acad. Sci USA, 85:8998–9002). The cDNAs obtained were subcloned into the Bluescript SK+vector and sequenced (clones B and C). Oligonucleotide 7 was derived from the sequence of a genomic clone (Carroll, unpublished results). This primer was used to create clone D using the same RACE protocol as for clone C. A full length cDNA clone (E) for expression in eucaryotic cells was obtained using primers 9 and 10 for PCR.

6.1.3. Norhtern Blot Analysis

RNA was extracted from various rat tissues using the guanidinium thiocyanate extraction method (Chomczynski, P. and Sacchi, N., 1987, Anal. Biochem., 162:156–159). An equal amount of total RNA (30 µg RNA, except mRNA from muscle which was 50 µg) was glyoxylated and electrophoresed through a 1.2% agarose gel (Lindholm et al., 1988, Biol. Chem. 263:16348–16351). To evaluate the developmental expression of CNTF mRNA in the sciatic nerve of the rat, 25 µg of total RNA derived from rat sciatic nerve were electrophoresed as described supra; PO, P4 and P13 in FIG. 4(b) refer to RNA derived from sciatic nerve of newborn, 4 day old, and 13 day old rats, respectively. Known amounts of a 847 bp CNTF transcript (synthesized in vitro using the riboprobe system, PROMEGA) were also coelectrophoresed in separate lanes to permit quantification of CNTF-mRNA in the samples. Following electrophoresis, RNA was vacuum-blotted to nylon filters (Hybond-N, Amersham) and the filters were hybridized at 50° C. in 50% formamide (Lindholm et al., supra) using a double-stranded $^{32}$P-labelled cDNA probe for the coding region of CNTF (600 bp). The filters were subsequently washed, exposed for 60 h to x-ray films and the autoradiogram was photographed.

6.1.4. Expression of Recombinant CNTF

An expression vector with cytomegalo-virus-promotor (gift of David Russell) was used for subcloning a full-length CNTF clone in both orientations. HeLa cells were used for transfections, as no basal expression of survival promoting activity for embryonic chick ciliary neurons could be detected in these cells. Each culture dish (100 mm diameter) was transfected with 10 µg of vector by the DEAE-Dextran method (Spandidos, D. A., and Wilhie, N. M., 1984, Transcription and Translation—A Practical Approach, 1–48). After 48 h in culture the supernatants were removed, the cells washed 3 times with cold PBS and lysed in a 5 mM Phosphate buffer containing 30 mM NaCl (pH 7.0). After ultracentrifugation (100,000×g, 30 min.) of the lysate protein concentrations were determined and different concentrations of the supernatants were added to cultured E8-ciliary neurons. Surviving neurons were counted after 24 h of culture as described previously (Hughes et al., 1988, Nature, 335:70–73). Each point in FIG. 3 shows the mean of three determinations; the bars represent the standard errors.

6.2. Results

6.2.1. Determination of CNTF Amino Acid Sequence

CNTF was purified from rat sciatic nerve as described supra. For amino acid quantification, production of cyanogen bromide (BRCN) and tryptic fragments (the N-terminus was blocked), the additional Bakerbond Gold purification step was necessary. The amino acid sequence of the various fragments determined by gas phase-microsequencing represented more than 50% of the total sequence which matched perfectly with that deduced from the cDNA and are presented with the nucleotide sequence shown in FIG. 1. The amino acid composition of the purified CNTF is shown in FIG. 1(d).

6.2.2. Generation of CNTF cDNA Clones and Sequence Analysis

Rat brain astroglial cell cultures were used as the RNA source for molecular cloning; these cells have previously shown to produce substantial quantities of CNTF (Lillien et al., 1988, Neuron, 1:485–494). After various PCR steps (using, as primers, synthetic oligonucleotides derived from the amino acid sequence data obtained as described in 6.2.1., supra), the nucleotide sequences of clones A, B, C revealed a short 5' untranslated region of 77 bp and an open reading frame of 600 bp, predicting a protein of 200 amino acid length with a 3' untranslated region of 436 bp, which ends in a Poly(A) tail (FIG. 1). One in-frame initiation site for translation was localized at position 78–80 of the nucleotide sequence. A stop-codon located 5' to this initiation site at position 72–74 and G's in position 75 and 81 fulfill the requirements for a convenient translation initiation site according to Kozak, M. J. (1989, J. Cell Biol. 108:229–241). A stop codon in position 678–680 follows a sequence coding for peptide CB2. The last amino acid identified by microsequencing was homoserine, indicating that the methionine, predicted from the nucleotide sequence had been posttranslationally modified and represents the C-terminus.

Although the dibasic (Arg-Arg) sequence in position 13 and 14 of the predicted sequence represents a potential posttranslational cleavage site, the amino acid composition of purified CNTF (FIG. 1(d)) speaks against such a cleavage: The amino acids phenylalanine, arginine and alanine present in the N-terminal region are not reduced relative to other amino acids which are absent from this region (e.g. isoleucine). Moreover, the predicted MW for the 200 amino acid sequence (22.8 KD) is in complete agreement with that estimated from PAGE analysis (22.5 KD) (Saadat et al., supra). Thus, the amino acid sequence of CNTF shows the features of a cytosolic protein, i.e. no signal peptide, no consensus sequences for glycosylation and only one cysteine residue at position 17. Comparison of the determined CNTF sequence with those of the FIR and EMBL databases did not reveal significant similarities with any other known protein. In particular, there was no homology with nerve growth factor (NGF), brain-derived neurotrophic factor (BDNF), or fibroblast growth factor (FGF) and Purpurin, each of which are associated with survival activities similar to those of CNTF (Unsicker et al., 1987, Proc. Natl. Acad. Sci. USA, 84:5459–5463; Schubert et al., 1986, J. Cell Biol., 102:2295–2301).

6.2.3. Expression of Recombinant CNTF

The likelihood that CNTF is a cytoplasmic protein was supported by the observation that expression of a full-length cDNA clone in HeLa cells resulted in active CNTF being expressed but not being released into the culture medium (FIG. 3). CNTF therefore appears to be a molecule similar to FGF and Interleukin-1 (IL-1) which exert profound effects on cells but which are cytosolic proteins. For FGF, no release mechanism has been established (Abraham et al., 1986, Science, 233:545–548). In contrast, IL-1 has been demonstrated to be released from stimulated macrophages by an unconventional mechanism after cleavage by a specific enzyme (convertase) (Kostura et al., 1989, Proc. Natl. Acad. Sci., USA, 86:5227–5231). Of particular interest is the recent finding that macromolecles may be exported from the yeast cytosol by carriers which show structural homologies with the multidrug-resistance glycoprotein in mammalian cells (McGrath and Varshasky, 1989 Nature 340:400–404). Whether this glycoprotein can also act as a protein carrier in mammalian cells remains to be established.

6.2.4. Northern Blot Analysis

Northern blot analysis (FIG. 4) of the distribution of CNTF-mRNA in tissues of adult rat revealed a single band about 1.2 kb in size. By far the strongest signal was present in Northern blots of the sciatic nerve and a faint band was present in extracts of the spinal cord. However, there was no detectable signal in mRNA of muscle and skin, i.e. <2 $\mu$g of CNTF-mRNA in 50 $\mu$g of total RNA. The low levels of CNTF-mRNA in muscle and skin indicates that the large amount of CNTF present in the sciatic nerve does not represent CNTF transported retrogradely from the periphery, as is the case for NGF, but represents locally synthesized CNTF.

Moreover, the developmental time-course of CNTF-mRNA expression differs from that of NGF (Thoenen et al., 1987, Biochem. Pharmacol., 109:145–178). CNTF-mRNA was undetectable in sciatic nerves of newborn rats, only becoming apparent by day 4 (FIG. 4(b)). The developmental time-course of CNTF-mRNA expression suggests that CNTF is not involved in the regulation of neuronal survival in the perinatal period as target-regulated neuronal cell death is already over by the time the increase in CNTF synthesis begins (Oppenheim, 1986, J. Comp. Neurol. 246:281–286; Johnson et al., 1980, Science 210:916–918).

6.3. Discussion

Figure 2A:
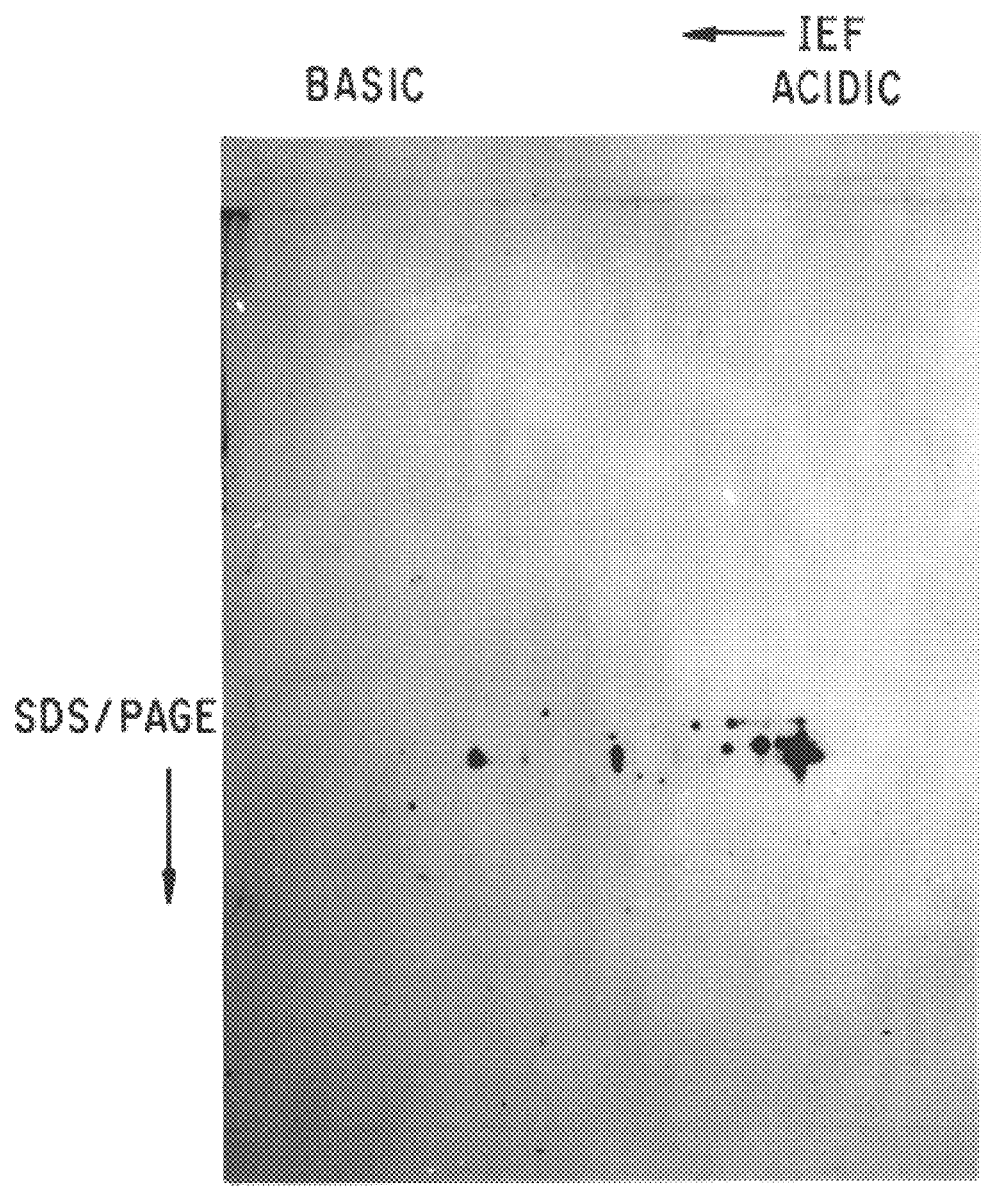
Figure 2B:
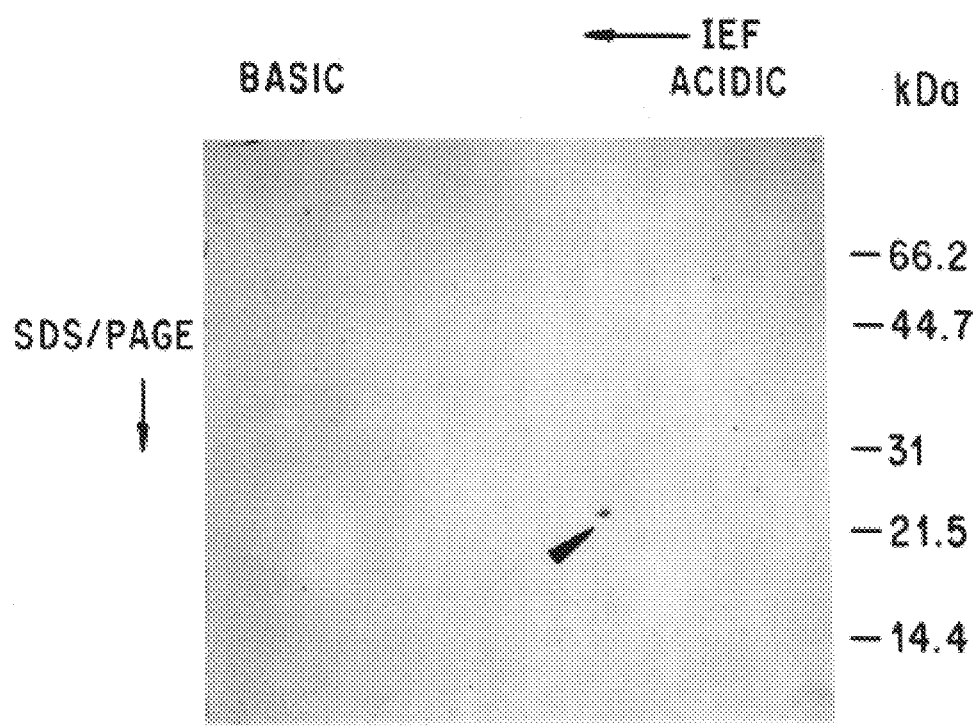

The methods of purifying CNTF described above provides, for the first time, a means of producing CNTF suitable for amino acid sequencing. Absent the final step of purification on the Bakerbond Gold C4 Widepore column, a number of contaminating peptides were present in the CNTF preparation, as shown in FIG. 2(a). However, following purification on the Bakerbond Gold C4 Widepore FPLC/ HPLC column, only a single spot was identified by 2D gel electrophoresis (FIG. 2(b)) indicating virtually complete purification. It should be noted that a number of HPLC columns had been used in unsuccessful attempts to purify CNTF before the Bakerbond Gold C4 Widepore column was found to be effective. It is hypothesized that the inert character of the gold plating facilitates purification of CNTF.

Although CNTF activity was originally characterized as a survival factor for chick ciliary neurons in vitro (Adler, et al., 1979, Science, 204:1434–15362), more recently, activities described as CNTF, derived from either chick or rat tissue, have been shown to promote the survival of a variety of other neuronal cell types (Barbin et al., 1984, J. Neurochem., 43:1468–1478; Manthorpe et al., 1986, Brain Res., 367:282–286) and rat sciatic nerve CNTF has been shown to affect the differentiation of E7 chick sympathetic neurons by blocking their replication and by inducing vasointestinal peptide (VIP) immunoreactivity, and (Ernsberger et al., 1989, Neuron 2:1275–1284) and choline acctutransferase (ChAT) activity in newborn rat sympathetic chain ganglia neurons (Saadat et al., 1989, J. Cell Biol. 108 : 1807–1816). Moreover, purified rat sciatic nerve CNTF promoted the differentiation of bipotental O2A progenitor cells to type-2-astrocytes (Hughes, 1988, Nature 335:70–73)) in vitro. To help establish which, if any, of these functions CNTF exerts in vivo, it is necessary to determine its primary structure, cellular expression, developmental regulation and localization. The cDNA-deduced amino acid sequence and subsequent expression of full-length cDNA clones in HeLa-cells now demonstrates that CNTF is a cytosolic protein. This, together with its regional distribution and its developmental expression, suggest that CNTF may not be a target-derived neurotrophic factor. CNTF thus seems to exhibit neurotrophic and differentiation properties only after becoming available either by cellular lesion or by a release mechanism(s) as yet unknown.

In summary, CNTF differs from the known neurotrophic factors NGF and BDNF by the absence of a known constitutive release mechanism, by the time-course of its expression during development and by its regional distribution. It may be that CNTF has a physiological role as a differentiation factor, its neurotrophic function possibly only being exerted under pathophysiological conditions rather than during embryonic development.

7. EXAMPLE: EXPRESSION OF CNTF IN ESCHERICIA COLI

7.1. Materials and Methods

7.1.1. Construction of a CNTF Expression Vector

The rat CNTF (rCNTF) gene was inserted in the expression vector pCP93 using a synthetic oligodeoxyribonucleotide primer complementary to the sequence spanning the 5' end of the gene and a second primer complementary to the sequence spanning the 3' end of the gene at the opposing DNA strand. Both primers were designed to include the recognition sequence for the restriction enzyme BspMI and their sequences are shown below.

```
5'  CAGTTACCTGCGGGGATGGCTTTCGCAGAGCAAACAC       3'
5'  CAGAGGTATGAGCAGGTGGCTACATCTGCTTATCTTTGG     3'
```

These primers produced, in a standard polymerase chain reaction (PCR) using pCMV-rCNTF-C-1 DNA as template and a commercial kit, a few micrograms of a 637 bp fragment that was purified by electrophoresis on a 6% polyacrylamide gel followed by electroelution. The eluted fragment was then digested with BspMI and the resulting 619 bp fragment was re-purified by the same method. After rendering blunt the protruding BspMI ends in a standard reaction using Klenow DNA polymerase, the fragment was ligated into the unique SalI restriction site of the pCP93 vector that had been rendered blunt by treatment with S1 nuclease in a standard reaction.

7.1.2. Identification of Bacteria Containing the CNTF Expression Vector

Competent E. coli W3110i$^q$F cells were transformed by this ligated DNA and screened for plasmid size and subsequently characterized by restriction analysis and DNA sequencing using standard methodology. (Panayotatos, N., 1987, In Plasmids: A Practical Approach, Hardy, K. G., ed. IRL Press, Oxford).

7.2. Results and Discussion

One of the plasmids (pCP-rCNTF-C-1) was found to carry the complete rCNTF gene fused in the correct orientation and translational reading frame to the ribosome binding signal of the vector. The copy number of this plasmid was three times higher than the parental, due to the deletion of 1400 bp of vector DNA.

E. coli W3110i$^q$F-/rCNTF-C-1 cells were grown in liquid culture in the presence of lactose (so that active transcription and translation occur through the rCNTF gene) and were found to contain significant amounts (2–5% of total cellular protein) of biologically active rCNTF. This was shown by electrophoresis on 8–25% gradient polyacrylamide gels followed by Coomassie staining as shown in FIG. 4. In addition, protein extracts were prepared from the same cells lysed by treatment with lysozyme followed by three cycles of freezing and thawing. Protein extracted by this method from a few microliters of culture was found to promote survival and neurite outgrowth of up to 50% of E10 rat ciliary ganglion neurons and approximately 30% of E8 dorsal root ganglion neurons after 24 and 48 hours in vitro. Maximal activity was seen at less than 1 nanogram rCNTF. No such activity could be detected in control extracts from the same host cells carrying the plasmid vector without the rCNTF gene.

Human CNTF sequence, engineered to lack intron sequences, has been inserted into the pCP93 vector and used to transform competent E. coli. Transformed bacteria carrying recombinant human CNTF sequences have been found to express a protein of an appropriate molecular weight for human CNTF; protein extracts of these cultures have been found to have CNTF activity in DRG assay.

8. EXAMPLE: CLONING OF THE HUMAN CNTF GENE

8.1. Materials and Methods

8.1.1. DNA, Plasmid and Phage Vectors

Human genomic DNA was obtained from human placental DNA (Clontech). pBLUESCRIPT plasmid vector was obtained from Stratagene. Bacteriophage vector EMBL-3 SP6/T7 was obtained from Clontech.

8.1.2. Polymerase Chain Reaction

PCR was carried out under standard conditions as suggested by the manufacture of a reagent kit (Perkins-Elmer/ Cetus) for 40 cycles, each cycle consisting of either incubation for 1 minute at 94° C., 2 minutes at either 40° or 50°, and 2 minutes at 72°.

8.2. Results and Discussion

8.2.1. Evidence for the Existence of a Human CNTF Gene

Southern blot hybridization under stringent conditions of human genomic DNA, digested with EcoRI restriction endonuclease, indicated that a single DNA fragment of approximately 10 kb showed weak homology with a rat CNTF probe (FIG. 6, panel b). In order to molecularly clone the putative human CNTF gene, efforts were made to amplify segments of such a gene by polymerase chain reaction (PCR), using pairs of oligonucleotide primers corresponding to exact sequences of the rat CNTF gene. For this approach to succeed, it would require that two short segments of the rat and human CNTF genes would be identical or nearly identical in DNA sequence.

Five pairs of oligonucleotides, each 17 to 21 bases long, were tested for the ability to prime amplified synthesis of DNA fragments by PCR, using total human genomic DNA as template. All five oligonucleotide pairs were chosen from within the second exon of the rat CNTF gene. It was hypothesized that a human CNTF gene would have a similar intron-exon structure to the rat gene. Only one pair of primers, designated CNTF.10 and CNTF.11, gave amplification of a DNA fragment from human genomic DNA of approximately the same size as would be obtained with the same primers using a rat DNA template (270 bp). A greater degree of amplification and lesser background were observed when PCR was carried out with DNA synthesis occurring at the higher (more stringent) temperature (50° C.). The sequences of CNTF.10 and CNTF.11 are as follows:

CNTF.10 (36-mer, antisense for amino acids EADGMPA; 2 bases each for terminal amino acids; tail with multiple cloning sites).

5'-CCAAGCTTCTAGAATTCGCAGGCATCCCATCAG CCT-3'

CNTF.11 (34-mer, sense for amino acids EMTEAE; 2 bases for terminal aa, final A; multiple cloning site at 5' end of oligonucleotide).

5'-GACTCGAGTCGACATCGGAGATGACTGAGGC AGA-3'

(The sequences corresponding to rat CNTF are underlined; and additional nucleotides were added to provide multiple cloning sites for subsequent cloning steps).

The products of the PCR reaction were resolved by electrophoresis on a 2% agarose gel (low melting temperature; NuSieve). The positive band of approximately 270 bp was cut out and reamplified by PCR using the same primer pair for 35 cycles (30 sec at 93° C., 1 minute at 50° C., 1 minute at 72° C.). The reamplified DNA fragment was again purified by electrophoresis on 2% agarose, and used as a template for DNA sequencing by the dideoxynucleotide chain termination method using a commercially available kit (the "FASTaq" kit from IBI). Primers for sequencing were CNTF.10 and CNTF.11, as well as two internal primers chosen on the basis of initial sequence data obtained with the terminal primers. The complete sequence of the amplified segment of human DNA is shown in FIG. 6. FIG. 7 The sequence comprised an open reading frame for a segment of a polypeptide very similar but not identical to rat CNTF.

8.2.2. Cloning of a Fragment of the Human CNTF Gene Amplified by PCR

The amplified human CNTF gene fragment was subcloned into the PBLUESCRIPT plasmid vector by cutting with EcoRI and XhoI and ligation to the vector DNA cut with the same 2 enzymes. DNA was introduced into competent cells of *E. coli* strain XL1-Blue (Stratagene), and transformants were selected for ampicillin resistance. Plasmid DNA was purified by standard methods, the inserted human DNA fragment was cut out with EcoRI and XhoI, isolated, and labeled for use as a hybridization probe. Labelling was carried out using PCR with approximately 20 ng of DNA as template and oligonucleotides CNTF.10 and CNTF.11 as primers, in a reaction mixture containing Taq DNA polymerase (Perkin-Elmer/Cetus), dATP, dGTP, dTTP, and $^{32}$P-dCTP for 6 cycles of 1 minute at 94°, 2 minutes at 50°, and 3 minutes at 72°. The labeled fragment was separated from unincorporated dCTP by standard chromatographic methods.

In order to determine whether the DNA fragment detected in human genomic DNA with a rat CNTF probe contained the sequences that could be amplified by PCR with primers CNTF.10 and CNTF.11, the radioactively labeled human fragment was used as probe in Southern blot hybridization on human and rat genomic DNA, digested with EcoRI (FIG. 6, panel a). The probe hybridized strongly to an approximately 10 kb band, indistinguishable from the band that hybridized weakly with a rat CNTF probe. Conversely, the human probe hybridized weakly to a band of approximately 4 kb in rat genomic DNA, indistinguishable from the band hybridized strongly by the rat CNTF probe. These results, in addition to the sequence data, indicated strongly that human DNA contains a homologue of the rat CNTF gene.

8.2.3. Cloning of the Human CNTF Gene from a Genomic Library

The radioactively labeled human CNTF probe, described above, was utilized to screen a genomic library of human DNA in the bacteriophage vector EMBL-3 SP6/T7. The library contained fragments of human placental DNA obtained by partial digestion with restriction endonuclease Sau3a, inserted into the vector at a BamH1 site. Bacteriophage were plated on *E. coli* strain LE392, and approximately 750,000 plaques were screened by hybridization, in duplicate, with the probe, using conditions essentially as described by Benton & Davis (1977, Science 196:180–182) {Both the DNA and phage are denatured and fixed in situ by dipping the filters in 0.1 N NaOH and 1.5 M NaCl for 20 seconds; the filters are then neutralized by dipping in 0.2 M tris, pH 7.5, and 2×SSCP (standard saline citrate phosphate buffer (SSCP) is (1×) 120 mM NaCl, 15 mM sodium citrate, 13 mM KH$_2$PO$_4$, 1 mM EDTA, titrated to pH 7.2 with NaOH) for 20 seconds. Filters are blotted and baked at 80° C. in a vacuum for 1.5 to 2 hours. Hybridization to the nitrocellulose replicas is carried out in a siliconized glass petri dish. The $^{32}$P-labeled probe (10$^5$ to 10$^6$ counts per minute per filter) is placed in enough 5×SSCP and 50 percent formamide to cover all filters. The hybridization mixtures were usually incubated for 12 to 18 hours. Buffer and probe can be recovered and reused for at least 2 weeks. After hybridization, the filters are washed in a large (10 to 15 ml per filter) volume of 5×SSCP and 50 percent formamide at 42° C. for 30 minutes and then for 20 to 30 minutes in 2×SSCP at room temperature.} and Mahmoudi and Lin (Mahmoudi, M. & Lin, V. K., 1989, BioTechniques 1:331–333) {One filter was hybridized with a 1056 base pairs Hind III-Sph I fragment containing the third exon of the chicken c-myc gene which was subcloned into Xba I site of PUC19, at 68° C. overnight. The hybridization buffer contained 6×SSC (20×SSC is a 3 M sodium chloride, 0.3 M sodium citrate), 1×Denhardt's (50×Denhardt's is 1% Ficoll, 1% polyvinylpyrrolidone and 1% bovine serum albumin, BSA), 50 mM EDTA (pH 8.0), 0.5% SDS and 100 µg/ml of tRNA. The filters were then washed twice in 6×SSC, 0.5% SDS at 68° C. for 20 min each, in 2×SSC at 68° C. for 20 min and once in 0.1×SSC at room temperature for 2 min. The other filter was hybridized to the same probe at 68° C. in a hybridization buffer containing 0.5 M sodium phosphate, pH 7.2 (1 M requires 134 g of Na$_2$HPO$_4$.7 H$_2$O and 4 ml of 85% H$_3$PO$_4$ per liter), 7% SDS, 1% crystalline BSA and 1 mM EDTA (pH 8.0). After overnight hybridization, the filters were washed twice in 40 mM phosphate buffer (pH 7.2), 5% SDS, 0.5% BSA (Fraction V), 1 mM EDTA (pH 8.0) for 30–60 min and twice in a hybridization buffer containing 40 mM phosphate (pH 7.2), 1 mM EDTA (pH 8.0) and 1% SDS for 30–60 min. Both washes were at the temperature of hybridization.}. One positive plaque was identified, and the recombinant phage was purified through three rounds of single-plaque isolation, using hybridization with the human CNTF probe to identify positives. The recombinant bacteriophage carrying the human CNTF gene was designated λhCNTF-G-1. Stocks were prepared for further analysis by growth in liquid culture using LE392 bacteria as host.

The human CNTF sequences present in λhCNTF-G-1 were analyzed further by PCR amplification and by DNA sequencing. Amplification with a pair of primers internal to the 270 bp human fragment originally sequenced (see above) was used to confirm that the correct fragment was present in the purified phage clone. The oligonucleotides were designated CNTF.13 and CNTF.16 (sequences below). As expected, in a PCR reaction using λhCNTF-G-1 as template and these primers, a product band of approximately 128 bp was amplified. PCR was carried out as above, but with 35 incubation cycles consisting of 1 minute at 94° C., 2 minutes at 50° C., 2 minutes at 72° C.

CNTF.13: 5'-GCAGCGACTTGGAGAAG-3'[antisense]

CNTF.16: 5'-TACCTTCCATGTTTTGTTGG-3' [sense] (this primer also contained a 5' "tail" containing sequences for a multiple cloning site—only the CNTF portion of the sequence is shown here).

In order to determine whether the AhCNTF-G-1 clone contained the 5' and 3' ends of the CNTF coding sequence, PCR reactions were carried out using exact sequence (i.e. non-degenerate) primers corresponding to the ends of the rat CNTF coding sequence. It should be noted that the ability to amplify DNA from the human genomic clone would indicate the presence of the corresponding region of the human gene, but the failure to amplify DNA could result either from the absence of the end of the coding sequence from the clone or from sequence divergence between rat and human.

The primers used to test for the presence of the probable 5' end of the human CNTF coding sequence were CNTF.13 (above) and CNTF.14. The latter oligonucleotide contained 22 bases corresponding to the 5' end of the coding sequence of rat CNTF (sense strand), and also had additional unrelated sequences at the 5' end (not shown) containing multiple restriction endonuclease recognition sites to facilitate potential cloning of amplified fragments.

CNTF.14 5'-ATGGCTTTCGCAGAGCAAACAC-3'

With the CNTF.13 and CNTF.14 oligonucleotide pair, a fragment of approximately 1.4 kb was amplified from the λhCNTF-G-1 template. This is the size that would be expected if the human CNTF gene contained an intron of about the same size (approximately 1 kb) as that found in the rat CNTF gene.

A similar effort to amplify a region between a known internal sequence of the human CNTF gene and the 3' end of the coding sequence was not successful. The primers were CNTF.16 (above) and CNTF.15, which contains the sequence of the 3' end of the rat coding sequence (antisense):

CNTF.15 5'-CTACATCTGCTTATCTTTGG-3'

Figure 8D:
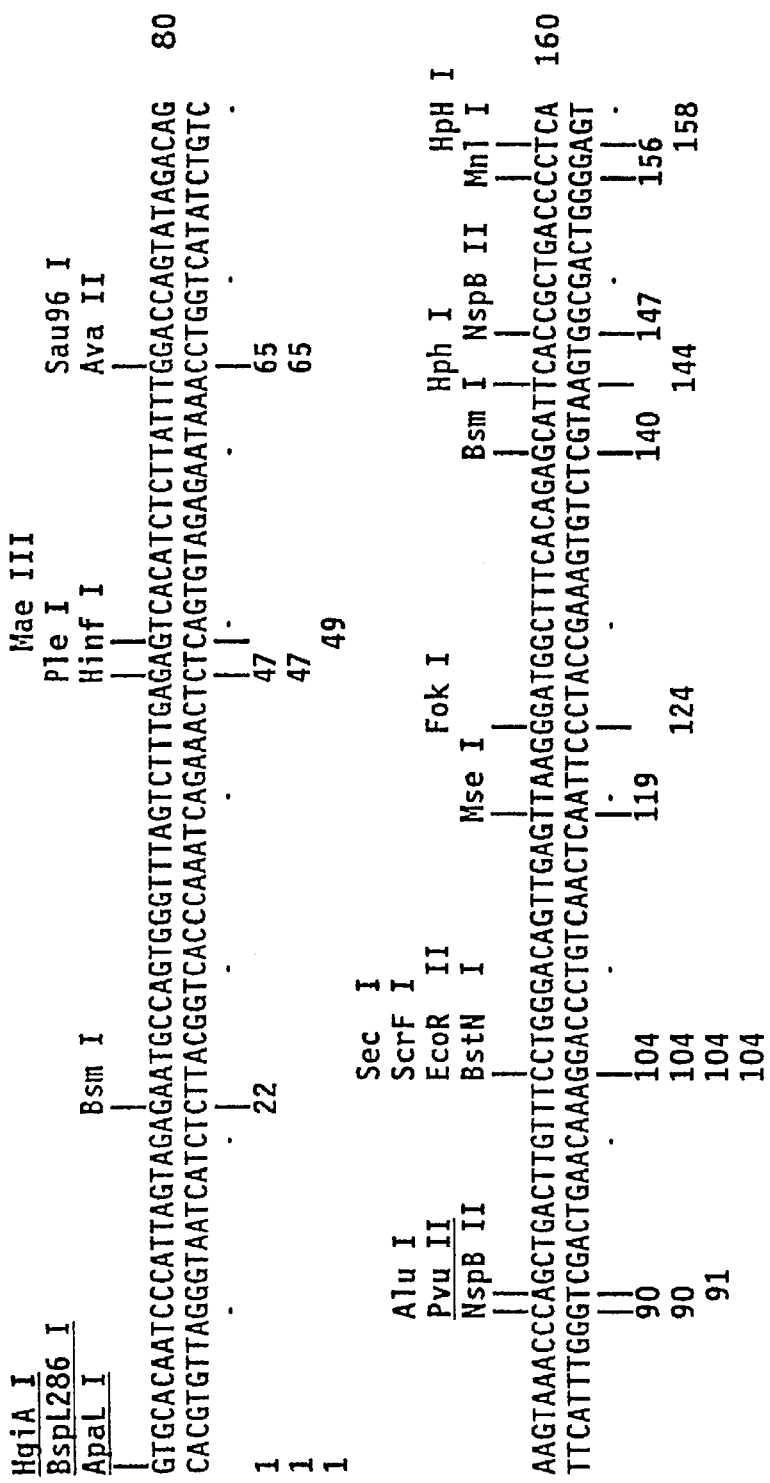
Figure 8D:
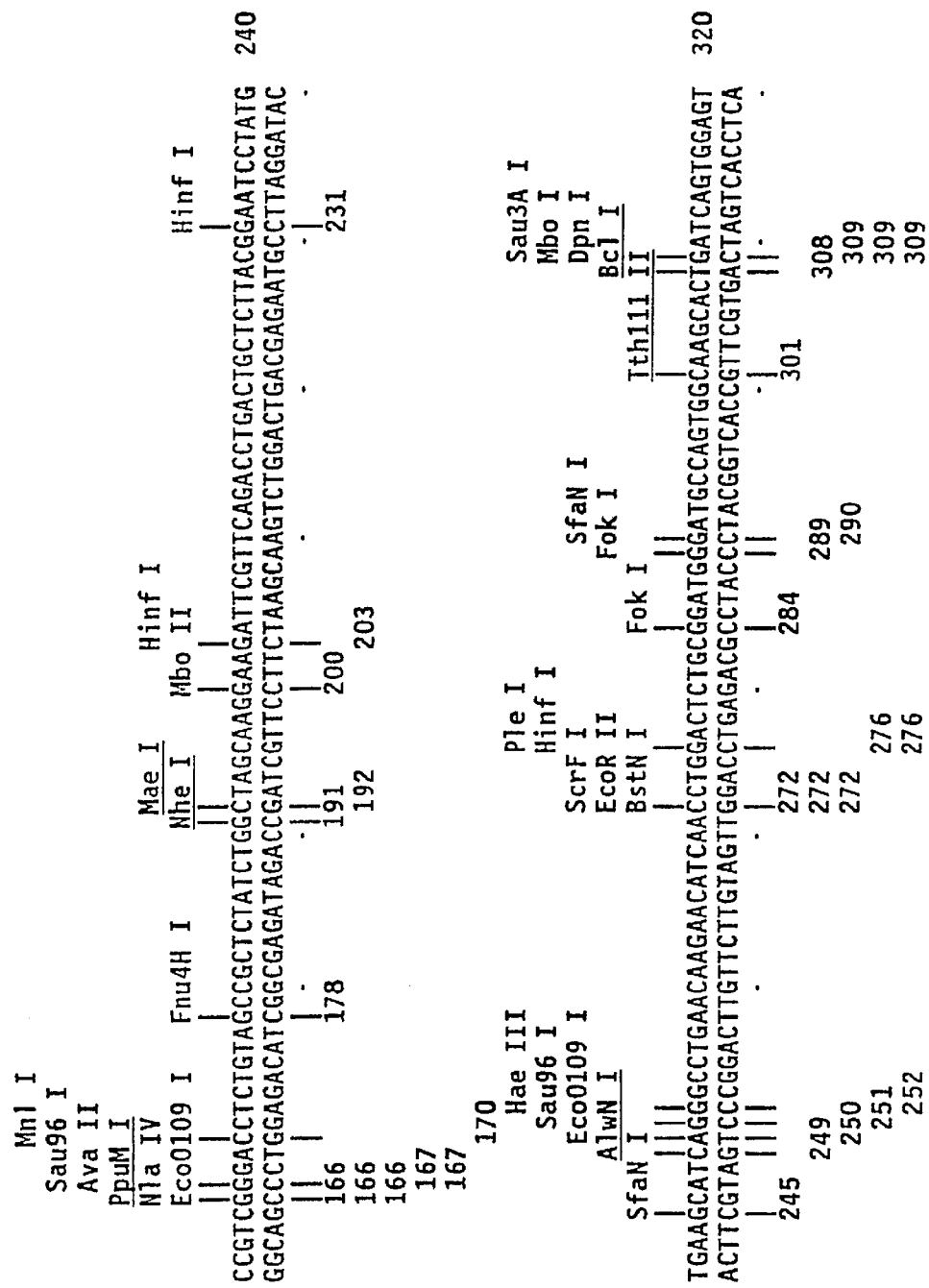
Figure 8D:
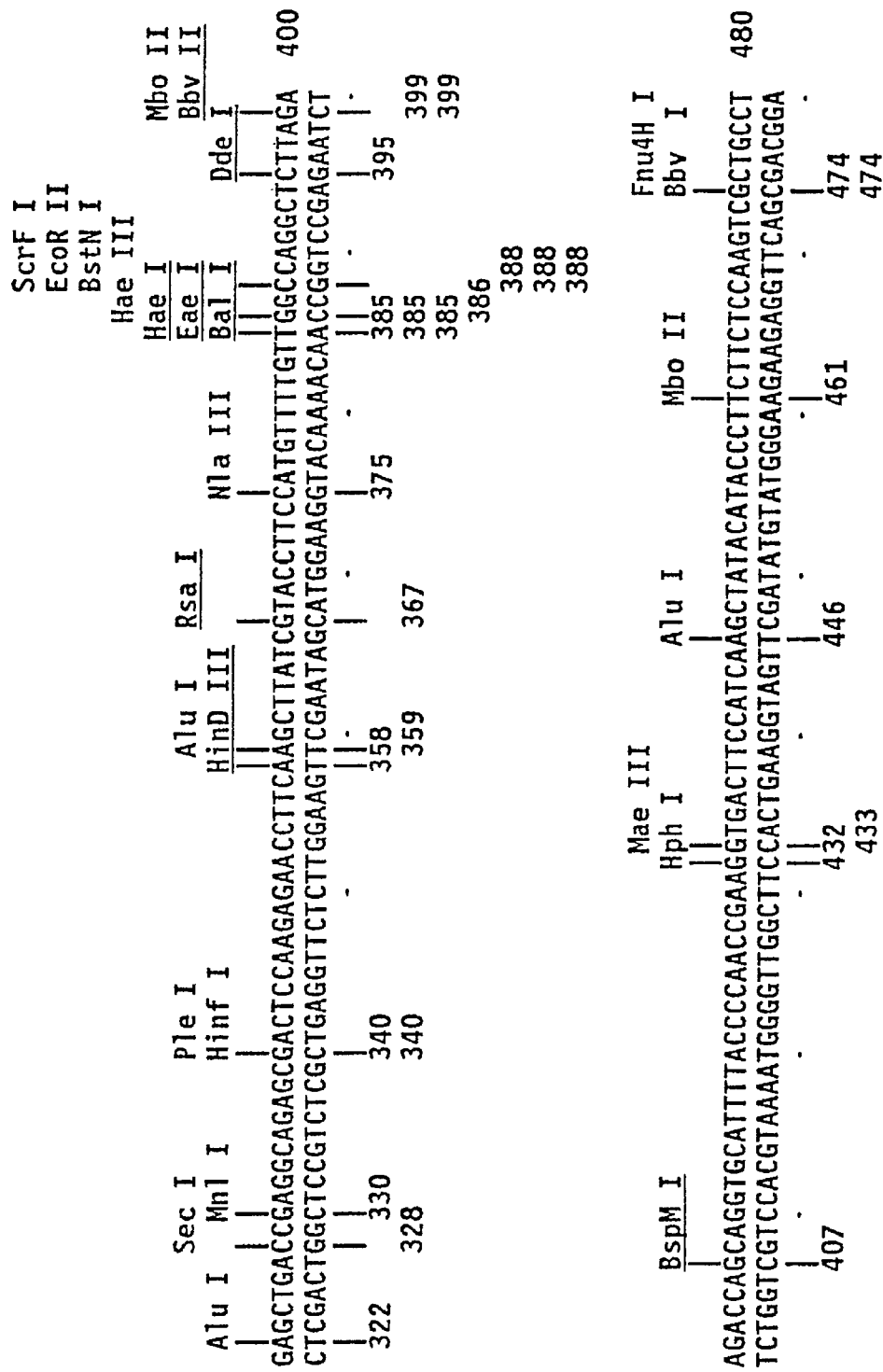
Figure 8D:
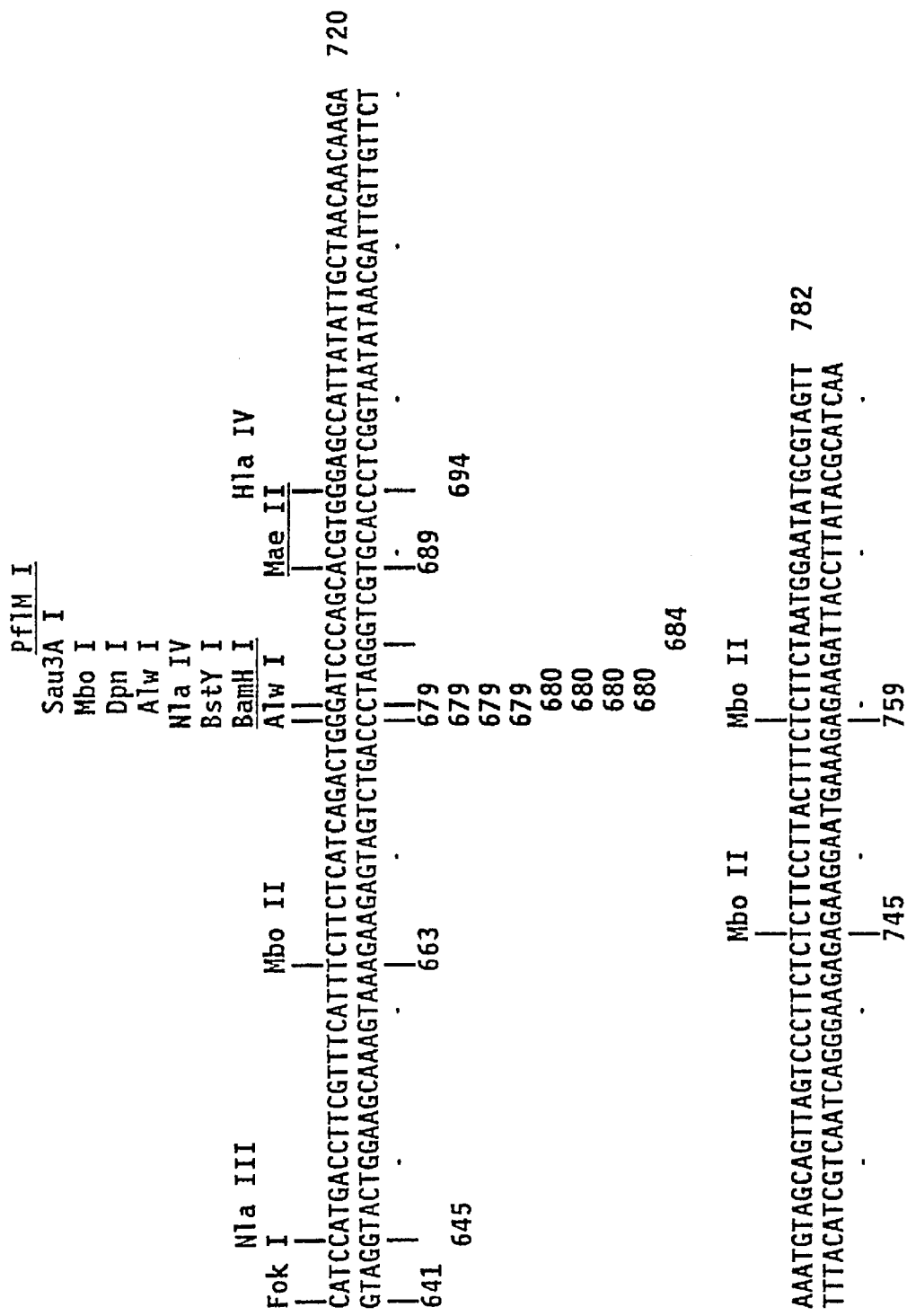

Sequence analysis was carried out on portions of the cloned human CNTF gene, and confirmed the similarity to the rat CNTF gene, but revealed a number of amino acid sustitutions in the encoded protein. The results of DNA sequence analysis within the human CNTF coding region and comparisons with the rat sequence, are shown in FIG. 8. The data are consistent with the human gene having a single intron at the same position as the rat CNTF gene; there is a long stretch of amino acid sequence identity (ESYVKHQGLNKN) spanning the intron-exon junctions. Within the intron, the human sequences have diverged considerably from the rat, in marked contrast to the substantial conservation of the coding region. There is one stretch in which five of six amino acids differ between human and rat CNTF (human: HVLLAR; rat: QGMLTK), and another two in which three out of four amino acids differ (human: TEHS; rat: AEQT, positions 4 through 7; and human: NNKK; rat: KDKQ at positions 196 through 199; FIG. 8(b)).

9. EXAMPLE: UTILITY OF CNTF-DERIVED PEPTIDE FRAGMENTS

9.1. Materials and Methods

9.1.1. Synthesis of Peptides

Peptides were synthesized on an Applied Biosystems solid-phase peptide synthesizer using f-moc chemistry.

9.1.2. Cell Culture

Chick embryo ciliary ganglion cultures were created and maintained according to the method set forth in (Hughes et al., 1988, Nature 335 : 70–73).

9.1.3. Immunization Protocol

Antibodies to the 14 amino acid CNTF peptide (SALESHYGAKDKQ) were prepared by immunization of rabbits with the peptide conjugated to KLH (keyhole limpet haemocyanin). To allowing coupling to KLH the 14 amino acid peptide was C-terminally extended with a Cys residue. Coupling of KLH and the peptide was achieved using a 100-fold excess of the peptide and MBS (m-maleimidobenzoyl-n-hydroxysuccinimidyl ester) as a coupling agent.

A rabbit was boosted with 1 mg of conjugate (peptide-KLH) in Freund's complete adjuvant. After 3 weeks the rabbit was boosted with a further 1 mg of conjugate in incomplete Freund's adjuvant. 2 weeks later the animal was re-boosted. A further 2 weeks later the animal was bled and serum was prepared. This serum was found to immunoprecipitate both the immunogen, and also purified rat sciatic nerve CNTF.

9.2. Results and Discussion

9.2.1. Ability of Antibodies Directed Toward a Synthetic Peptide to Neutralize CNTF Activity Saturating quantities of CNTF were incubated with protein-A-sepharose bound antibodies from either preimmune serum or immune serum from a rabbit immunized with the 14 amino acid synthetic peptide (I S A L E S H Y G A K D K Q). After incubation and centrifugation the supernatants were assayed for their ability to support the growth of E8 chick ciliary ganglion neurons. A normal CNTF dose response is seen in the control supernatants. Essentially no CNTF activity was detected after immunoprecipitation with anti-CNTF peptide fragment antibodies (FIG. 9).

9.2.2. Neurotrophic Activity of a Synthetic CNTF Peptide Fragment

E8 chick embryo ciliary ganglion neurons were cultured for two days in the presence of a range of concentrations of 28 amino acid synthetic peptide fragment derived from primary CNTF sequence data, and neuronal survival was quantitated. A dose-response relationship was observed between peptide concentration and neurotrophic activity (FIG. 10). The peptide sequence used was M V L L E Q K I P E N E A D G M P A T V G D G G L F E K.

9.2.3. Ability of Antibodies Directed Toward a Synthetic Peptide to Identify CNTF Containing Cells Antibodies directed toward the 28 amino acid peptide were used in immunofluorescence studies of rat sciatic nerve tissue. Rabbit antibodies directed toward the 28 amino acid peptide were incubated with fixed sections of rat sciatic nerve and nerve sections were subsequently reacted with rhodamine labelled anti-rabbit IgG antibodies. As shown in FIG. 11 periaxonic staining was observed, suggesting that CNTF may be synthesized by Schwann cells. In addition, structures present in the axonic cytoplasm were visualized (FIG. 11, small arrow) which would be consistent with either axonic synthesis or transport of CNTF into axons. Labelling could be blocked by the addition of excess CNTF peptide (M V L L E Q K I P E N E A D G M P A T V G D G G L F E K).

10. EXAMPLE: CILIARY NEUROTROPHIC FACTOR PROMOTES SURVIVAL OF SPINAL CORD NEURONS

10.1. Materials and Methods

10.1.1. Experimental Animals

Sprague-Dawley rats (HSD) were used for all experiments. Pregnant rats were sacrificed by carbon dioxide asphyxiation, and the embryos were rapidly removed and placed in ice-cold Puck's saline G for further dissection.

10.1.2. Tissue Culture Techniques

Spinal cords were removed aseptically from rat embryos on the 14th day of gestation. The spinal cord was severed caudal to the bulb, freed of sensory ganglia and meninges. The cord was then subdivided into ventral and mediodorsal segments for separate cultures. The cord tissues were minced into small pieces and mechanically dissociated by trituration through a Pasteur pipet in defined culture medium consisting of 50% basal medium Eagle (BME; Gibco) and 50% Ham's nutrient mixture F12 (Gibco) supplemented with glucose (33 mM), glutamine (2 mM), $NaHCO_3$ (15 mM), HEPES (10 mM), insulin (25 µg/ml), transferrin (100 µg/ml) putrescine (60 µM), progesterone (20 nM), Na selenite (30 nM), penicillin G (0.5 µg/ml), streptomycin (0.5 µg/ml), and bovine serum albumin (2.5 µg/ml). Trituration was repeated twice and the supernatants were pooled and filtered through a nylon (Nitex, Tetko) filter (40 µm). Total cell number yielded was determined by hemocytometer counting in the presence of trypan blue. Dissociated ventral cells were then plated at a density of 0.5 million cells/35 mm dish coated with poly-D-lysine (10 µg/ml). Dissociated mediodorsal cells were plated at a density of 1.5 million/35 mm dish coated with poly-D-lysine (10 µg/ml), poly-L-ornithine (10 µg/ml), or poly-L-ornithine with laminin (5 µg/ml). Treatments to these cultures were added at the time of plating. Cultures were maintained at 37° C. in a 95% air/5% $CO_2$ atmosphere at nearly 100% relative humidity. Culture medium was changed every three to four days. At one week, these cultures contained primarily neurons (stained with neurofilament monoclonal antibody RT97; Wood and Anderton, 1981, Biosci. Rep. 1:263–268) with only a few astrocytes (stained with glial fibrillary acid protein antibodies; Bignami and Dahl, 1973, Brain Res. 49:393–402) as demonstrated with immunocytochemistry.

10.2. Results and Discussion

10.2.1. Effects of Ciliary Neurotrophic Factor (CNTF) on Mediodorsal (MD) Spinal Cord Neurons Mediodorsal (MD) cultures did not survive in defined medium after the first 48–72 hours. The cells began to form clumps and eventually detached from the substrate. However, after one treatment with CNTF (20 ng of recombinant rat CNTF in 2 µl of E. coli extract per ml of culture) at the time of plating, MD neurons showed increased survival by 48 hours; they were well-attached to the substrate and extended neurites (FIG. 12). The difference was unlikely to be the result of the degree of cellular attachment, since cells in both control and CNTF-treated cultures were well-attached at 3 hours after plating. Furthermore, different substrates used gave similar results. Thus, it suggests that CNTF was capable of increasing the survival of the MD neurons in these cultures. Protein level was also determined. CNTF-treated cultures contained 6 times more protein/dish than untreated control and NGF-treated (50 ng/ml) cultures (Table I). Since the cultures contained primarily neurons, the increase in protein levels also suggests an increase in neuronal survival.

10.2.2. Effects of CNTF on Ventral Spinal Cord Neurons

Cultures of the ventral spinal cord segment are enriched with somatic motorneurons, as has been documented rigorously in work on embryonic chick motorneurons (Dohrman et al., 1986, Dev. Biol. 118:209–221 and see Example 18, infra), and confirmed in the present study of embryonic rat motorneurons by immunocytochemistry using choline acetyltransferase (CAT) antibody. In defined medium, ventral neurons survived quite well but eventually deteriorated after 1 week, probably due to the lack of factors secreted by glial cells (because these cultures contained relatively few glia). In the presence of CNTF (2 µl/ml), ventral neurons would survive beyond 1 week, with a small increase in protein and CAT enzyme levels as compared to control (Table II).

TABLE I

Mediodorsal neurons were treated with CNTF (2 µl/ml), NGF (50 ng/ml), or untreated at time of plating. At day 7, cultures were harvested for protein measurements using the Bradford method (Bradford, 1976, Anal. Biochem. 72:248–254)

|  | Control | CNTF | NGF |
| --- | --- | --- | --- |
| µg protein dish | 20 | 120 | 20 |

TABLE II

Ventral neurons were treated with CNTF (2 µl/ml), NGF (50 ng/ml) or untreated at time of plating. At day 7, cultures were harvested for CAT enzyme level determination (Hartika and Hefti, 1988, J. Neurosci. 8:2967–2985) and protein measurements.

|  | Protein µg/dish | CAT Activity CPM/dish |
| --- | --- | --- |
| Control | 33 | 590 ± 26.52 |
| CNTF | 45 | 959.5 ± 24.32 |
| NGF | 38 | 621.25 ± 33.59 |

11. EXAMPLE: PURIFIED RAT SCIATIC NERVE CNTF PREVENTS LESION-INDUCED CELL DEATH OF MOTORNEURONS IN THE FACIAL NERVE (VIIth CRANIAL NERVE) OF THE NEWBORN RAT

11.1. Materials and Methods

The facial nerves of newborn rat pups were sectioned unilaterally and small gelfoam implants containing either 5 µg bovine serum albumin or 5 µg CNTF were placed at the lesion sites. A group of lesioned animals which did not receive gelfoam implants was used as a control. After one week, the animals were sacrificed and sections of their brainstem, containing a facial nerve nucleus on the same side as the lesioned nerve (ipsilateral to the lesion) and a facial nerve nucleus on the side opposite to the lesion (contralateral to the lesion) were produced. The contralateral facial nucleus served as an internal control. Facial nucleus sections were stained with either Nissl stain (to stain motorneurons) or with antibody to glial fibrillary acidic protein (to detect the respose of glial cells to injury).

11.2. Results and Discussion

Figure 13A:
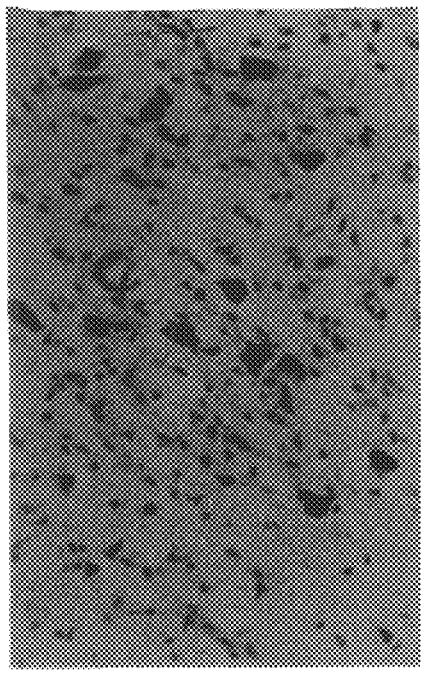
Figure 13B:
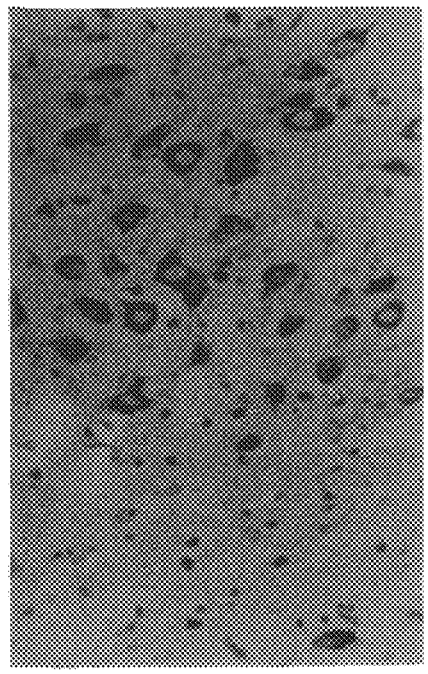
Figure 13C:
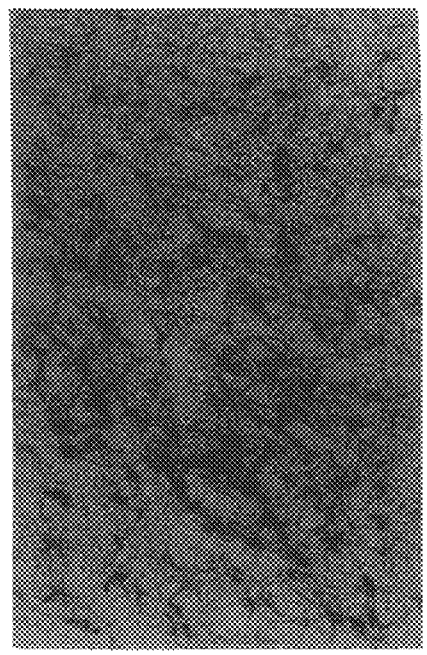
Figure 13D:
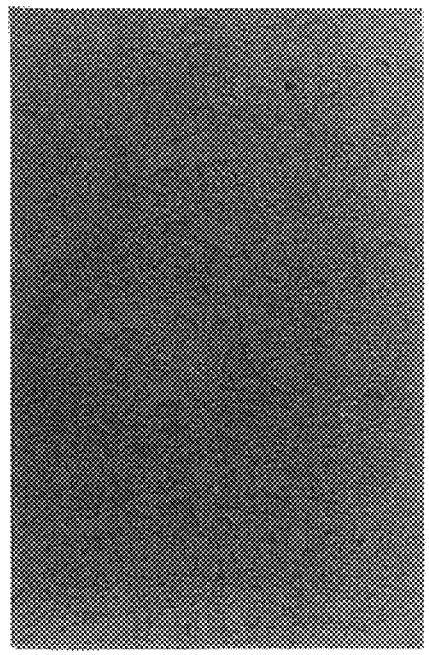
Figure 14A:
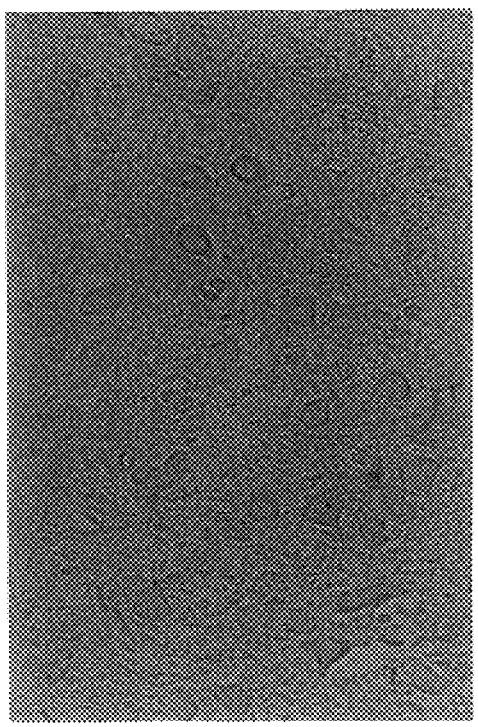
Figure 14B:
Figure 14C:
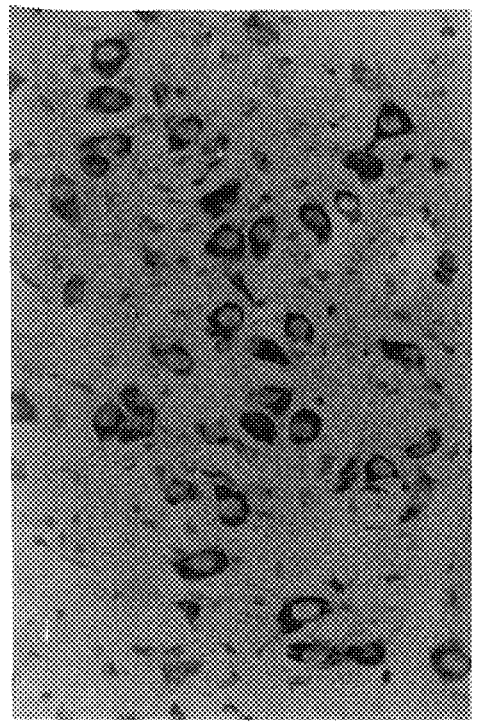
Figure 14D:
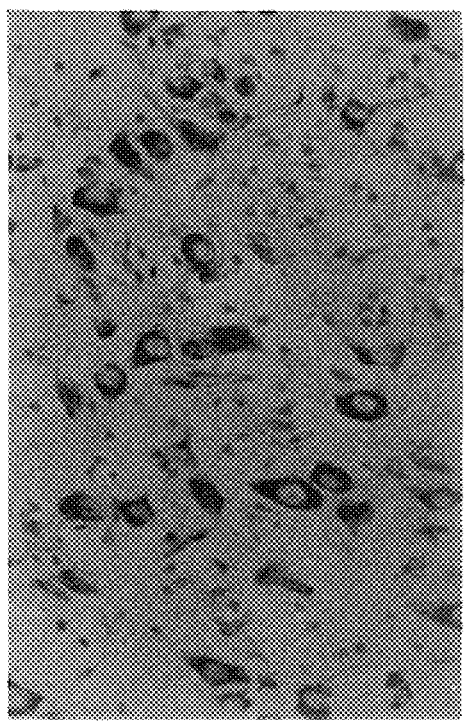

As shown in FIGS. 13A and B, lesion of the facial nerve and placement of a BSA-containing gelfoam implant resulted in a decrease in the number of motorneurons; furthermore, those motorneurons remaining appeared condensed and shrunken. However, lesion of the facial nerve and placement of a CNTF-containing gelfoam implant appeared to be associated with substantially greater motorneuron survival (FIGS. 14A and B); the motorneurons in FIG. 14A appeared to more closely resemble the healthy motorneurons on the unlesioned side (FIG. 14B) than the shrunken, degenerating motorneurons of FIG. 13A. Furthermore, the affect of CNTF was observed to be directed largely at promoting motorneuron survival rather than at preventing gliosis; a comparable amount of gliosis was observed in facial nuclei ipsilateral to facial nerve lesion in BSA treated and CNTF-treated rats (FIGS. 13C and 14C).

The number of motorneurons in the facial nuclei of untreated, BSA-gelfoam and CNTF-gelfoam treated rats were counted; data is presented in Table III.

In lesioned animals which were untreated or treated with gelfoam+BSA, a 90% loss of motorneurons was observed ipsilateral to the lesion. In animals treated with a gelfoam implant impregnated with CNTF, the motorneuron pool ipsilateral to the lesion was 70% of normal (approximasely a 30% loss).

In conclusion, following lesion of the facial nerve of the newborn rat 90% of the motorneurons of the facial nerve nucleus were found to degenerate within 1 week. Application of CNTF to the cut stump of the newborn rat facial nerve dramatically reduced the cell loss due to nerve section as shown in FIG. 14A and Table III; CNTF was found to rescue at least 60% of the facial nerve motorneurons that would normally have died after axotomy. CNTF is thus demonstrated to be a survival factor for motorneurons in vivo.

TABLE III

CNTF Rescues Facial Nerve Motorneurons From Axotomy-Induced Cell-Death In The Neonatal Rat

| Treatment | Count Of Motorneurons In The Facial Nerve Nuclei | |
|---|---|---|
| | Lesion-side | Contralateral (Control side) |
| CONTROL (No Gel Foam) | 685 | 2985 |
| | 330 | |
| | (530) | |
| GEL FOAM + BSA (5 µg) | 775 | 3360 |
| | 645 | 3300 |
| | 440 | 3150 |
| | (620) | (3271) |
| GEL FOAM + CNTF (5 µg) | 2205 | 3425 |
| | 3445 | |
| | 1270 | 2990 |
| | 3095 | 3490 |
| | (2120) | (3301) |

12. EXAMPLE: HIGH LEVEL EXPRESSION AND PURIFICATION OF RECOMBINANT HUMAN AND RAT CILIARY NEUROTROPHIC FACTORS IN *ESCHERICHIA COLI*

12.1. Materials and Methods

12.1.1. Bacterial Strains and Plasmids

E. coli W3110lacIqF−, a strain that overproduces the lactose operon repressor, and the parent plasmid vectors pCP93, pCP110, pblk0 and pblk1 have been used in previous studies (Panayotatos, N., 1988, Gene 74:357–363; Panayotatos et al., 1989, J. Biol. Chem. 264:15066–15069). Vectors engineered for CNTF expression were created as follows and their relevant properties are summarized in Table IV.

12.1.1.1. Rat CNTF Vectors

12.1.1.1.1. pRPN11

A 622 bp DNA fragment encoding the complete rat CNTF protein was obtained from a cDNA clone (Stockli et al., Nature 342:920–923) by polymerase chain reaction (PCR). The synthetic oligodeoxyribonucleotide primers used to obtain this fragment were designed to generate a 5' end coding for the alanine at the amino terminus of the protein, and to terminate 19 bp beyond the TAG termination codon at the 3' end. The expression vector pCP93 was linearized with SalI, rendered blunt by treatment with Si nuclease and the resulting 3,920 bp fragment was purified by agarose gel electrophoresis. The vector and PCR fragments thus prepared were ligated and transformed in E. coli W3110lacIqF−. Transformants were screened by size and restriction mapping for the desired plasmid (FIG. 16), and a positive candidate (pRPN11) was confirmed by DNA sequencing to carry the expected full length gene fused to the translation initiation signal in the correct reading frame. However, as discussed below, a single bp mutation was found in the CNTF gene in pRPN11, relative to the original rat cDNA, leading to incorporation of asparagine in place of tyrosine at position 193 of the protein sequence. This mutation, which must have arisen during PCR amplification, was carried over into all other vectors carrying the rat CNTF gene.

12.1.1.1.2. pRPN12

This plasmid is identical to pRPN11, except for a single bp mutation in the copy control region (cop1) that increases the copy number in host cells approximately fivefold. It was constructed by replacing the DNA between the EagI and PvuI sites (clockwise) with the same sequence from pCP110 (Panayotatos et al., 1989, J. Biol. Chem. 264:15066–15069).

12.1.1.1.3. pRPN37

The DNA region between the two AseI restriction sites spanning the b-lactamase gene in pRG12 (FIG. 16) was replaced with a DNA segment conferring resistance to kanamycin (kanR). In this vector, the kanR gene is under the transcriptional control of its native promoter.

12.1.1.1.4. pRPN38

This plasmid is identical to pRPN37, except for a 4 basepair site-directed mutation that minimizes the strength of the kanR promoter (Panayotatos, N., 1988, Gene 74:357–363).

12.1.1.2. Human CNTF Vectors

12.1.1.2.1. pRPN32

This plasmid is analogous to pRPN11, except that it carries the human instead of the rat gene. To express the human CNTF protein in bacteria, it was necessary to remove the intron separating the protein-coding sequences. This was accomplished by using PCR to amplify and join the regions flanking the intron, as follows. Two reactions, each with 100 ng genC.1 DNA as a template, were set up (FIG. 17): one contained 1 M CNTF.23 primer and 10 nM CNTF.21 primer, and the other 1 µM CNTF.24 primer and 10 nM CNTF.22 primer. After 10 PCR cycles (each cycle constituting incubation for 1 minute at 94° C., 2 minutes at 50° C., 2 minutes at 72° C.) the two samples were combined and subjected to another 25 cycles in the DNA Thermal Cycler. Because the internal primers CNTF.21 and CNTF.22 are fully complementary to each other, the products of the first stage PCR reactions can subsequently anneal. Furthermore, in the second stage reaction, the presence of substantially higher concentrations of the external primers CNTF.23 and CNTF.24 drives the synthesis of large amounts of the desired full-length product. The internal primers were chosen to bridge the two segments of the coding region, thus leading to the deletion of the intron. The products of the final PCR reaction were analyzed by agarose gel electrophoresis, and only one major band was detected by ethidium bromide staining. The size, about 600 bp, and a partial nucleotide sequence indicated that this band represented a precisely spliced coding region of human CNTF.

The 5' external primer CNTF.23 (FIG. 17) was designed to generate a blunt end coding for alanine at the amino terminus of the protein. The 3' external primer CNTF.24 (FIG. 17) provided an EagI restriction site 12 bp beyond the end of the CNTF coding sequence. This primer was also designed so as to replace the naturally occurring TAG termination codon with TAA, which is less subject to translational read through in E. coli. The PCR fragment was restricted with EagI and the resulting 612 bp fragment was purified by polyacrylamide gel electrophoresis. The expression vector pCP93, which provides the ATG initiation codon, was linearized with SalI, rendered blunt by treatment with S1 nuclease, digested with EagI and the resulting 3,636 bp fragment was purified by agarose gel electrophoresis. The vector and PCR fragments thus prepared were ligated and transformed in *E. coli* W31101acIqF–. Transformants carrying the desired molecules were identified by restriction mapping and tested for the presence of a protein of the expected size upon induction.

Analysis of protein synthesis by gel electrophoresis in induced cultures of *E. coli* W3110lacIqF– carrying one of the candidate plasmids (pRPN32) revealed the presence of a protein band of approximately 27,000 MW that was absent in induced control cultures of bacteria carrying the pCP93 plasmid vector. Rapid protein extracts from these cultures revealed the presence of biologically active CNTF.

12.1.1.2.2. PRPN33, pRPN39 and pRPN40

Except for the presence of the human instead of the rat CNTF gene, these plasmids are analogous to pRPN12, pRPN37 and pRPN38, respectively, and were constructed in the same fashion using pRPN32 as the parent plasmid. The copy control region between the EagI and PvuI sites (clockwise) in pRPN32 was replaced with the same sequence from pCP110 to create pRPN33. Then, the β-lactamase coding region between AseI restriction sites in pRPN33 was replaced with the mutated kanR region of pblk1 (Panayotatos, N., 1988, Gene 74:357–363) to create pRPN40. Finally, the region between the NdeI and BglII restriction sites of pRPN40 and pblk0 (Panayotatos, N., 1988, Gene 74:357–363) was exchanged to create pRPN39, in which the kanR gene is under its wild-type promoter.

12.1.2. Induction of Protein Synthesis

Cells were shaken in LB broth at 37° C. to $OD_{590}=1$. Lactose was added to 1% final concentration and incubation continued for 16 to 20 hours.

12.1.3. "Rapid" Protein Extraction

Samples for gel electrophoresis were prepared by resuspending cell pellets from 0.5 ml culture $OD_{590}=2$ in 0.16 ml lysis buffer (100 mM TrisHCl, 10% glycerol, 4% sodium dodecyl sulfate, 1 mM dithiothreitol, 0.5 mg/ml bromophenol blue, pH 6.8) and boiling for 5 minutes.

Selective Extraction/Solubilization—The method initially described for recombinant human leukocyte interferon α2 (Thatcher, D. and Panayotatos, N., 1986, Methods Enzymol. 119:166–177) was used, modified as follows. Cells from induced cultures were resuspended and stored below –20° C. Following lysozyme treatment, the viscous suspension was passed through a French Press (SLM-Aminco) at 8,000 psi, centrifuged at 11,000×g and the pellet was processed (Thatcher, D. and Panayotatos, N., 1986, Methods Enzymol. 119:166–177). After exhaustive dialysis of the material solubilized by 8M guanidinium chloride against Buffer D (10 mM Tris-HCl, pH 8.0, 5 mM EDTA, 0.1 mM dithiothreitol) and centrifugation at 11,000×g, the clear supernatant was passed aseptically through a Millipore Sterifil D-GV filter.

12.1.4. Chromatography

The filtrate was adjusted to 25 mM NaCl and applied at a rate of 0.5 ml/min to a 5×10 cm DEAE Sephacel column (Pharmacia) equilibrated with Buffer E (20 mM Tris HCl, pH 8.0, 0.1 mM EDTA, 0.1 mM dithiothreitol, 25 mM NaCl). The column was washed with one bed-volume of the same buffer and eluted with three bed-volumes-of a linear gradient 25–500 mM NaCl in the same buffer. Recombinant rat CNTF eluted at 250–350 mM NaCl, whereas human CNTF eluted at 50–100 mM.

For rat CNTF, pooled peak fractions were dialyzed against buffer E, filter-sterilized and stored at –70° C.

For human CNTF, pooled peak fractions from the DEAE Sephacel column were adjuste to 40 mM MES (Boehringer) pH 6.0, 0.1 mM EDTA, 0.1 mM dithiothreitol (buffer G), passed through a 0.22 μm Millex GF filter and applied to a 5×10 cm Fast-S column (Pharmacia) at 1.0 ml/hr. After washing with two bed volumes of buffer G containing 250 mM NaCl, a three bed-volume gradient of 250–1000 mM NaCl in buffer G was applied. Human CNTF eluted at about 600 mM NaCl. Peak fractions were dialyzed against buffer E, filter-sterilized and stored at –70° C.

12.1.5. Peptide Analysis

12.1.5.1. Rat CNTF

Recombinant rat CNTF (50 μg) was subjected to cleavage by BrCN as described (Stockli et al., Nature 342:920–923). The resulting peptides were separated by reverse phase HPLC using RP C4, and the chromatographic pattern was compared with that of BrCN-cleaved rat sciatic nerve CNTF. The peptide previously identified as the most C-terminal was subjected to amino acid analysis. In addition, the N-terminal peptide was identified and subjected to amino acid analysis.

12.1.5.2. Human CNTF

Recombinant human CNTF (400 picomoles) in 1.5 ml of 0.1% TFA/50% acetonitrile was concentrated in a Speedvac to a final volume of 300 μl. The sample was loaded onto a minicolumn (Vydac C-4, 214 TPB, 300 A, 10 μm), washed twice with 0.1% TFA/10% acetonitrile, and eluted with 0.1% TFA/70% acetonitrile. The elute was concentrated in the Speedvac to approximately 10μl. C-terminal cleavage was carried out with 2% Carboxypeptidase Y and P (Boehringer Mannheim, sequencing grade) in 20 μl total volume at 33° C. at pH 3.79, 5.0 and 6.12 adjusted by adding sodium citrate (final concentration of 0.025 to 0.05 M). At intervals between 10 and 65 minutes of incubation, 3 μl of 99% formic acid and 200 pmol of aminoethanol (used as an internal standard) were added, and the sample was applied to the minicolumn as described above. Cleaved amino acids were eluted and the column was washed twice with 0.1% TFA/10% acetonitrile. The amino acids were dried, and analyzed after derivatization with O-phtal-dialdehyde. CNTF was eluted from the column with 0.1% TFA/70% acetonitrile, concentrated to 10 μl and the cleavage repeated.

12.1.6. Biological Activity

Biological activity of recombinant CNTF was assayed on explants of chick embryo dorsal root ganglia (DRG) and dissociated cultures of ciliary ganglion (CG) neurons as described in Lindsay and Rohrer (1985, Devel. Biol 112:30–48). Briefly, DRG were dissected from chick embryos of 10 days incubation (E10) and 5–6 ganglia were explanted in 1 ml of a collagen gel matrix in 35 mm tissue culture dishes. After the gel had set, 1 ml of tissue culture growth medium F14 (Imperial Labs., U.K.) supplemented with 5% heat-inactivated horse serum (GIBCO) was added before adding human CNTF (1–20 l) to a final concentration of 100 pg to 100 ng/ml. CG were dissected from E8 chick embryos and incubated for 30 min in 0.25% trypsin (Worthington) in calcium- and magnesium-free phosphate buffered saline. The ganglia were then washed three times in F14 medium containing 5% horse serum before being dissociated to a single cell suspension by trituration through the bore of a Pasteur pipette. Enrichment for CG neurons was achieved by plating the cell suspension for 3.5 hr in a 60 mm dish, during which non-neuronal cells (fibroblasts and Schwann cells) attached firmly to the plastic while phase-bright neurons remained in suspension. The purified neurons were plated on polyornithine-laminin-coated 35 mm culture dishes at 8,000–10,000 neurons/dish. In explant cultures CNTF activity was determined by assessing the extent of fiber outgrowth in treated cultures compared to controls. Fiber outgrowth was scored on a scale of 0 to 5+, by comparing cultures to photographs of a dose-response of explanted DRG and NGF. In dissociated CG neuron cultures, CNTF activity was determined by counting at 48 hr the percentage of process-bearing neurons in control and CNTF-treated cultures. In all cases results were derived from triplicate cultures.

12.1.7. Other Methods

Conditions for enzymatic reactions, DNA electrophoresis and other techniques used in these studies have been described in detail (Panayotatos, N., 1987, In K. G. Hardy (Ed.), Plasmids: A Practical Approach. IRL Press, Oxford, U.K., pp. 163–176). DNA sequencing was carried out with a Sequenase Version 2.0 kit (USB Corporation) using 4 mg of supercoiled plasmid as a template.

12.2. Results and Discussion

Previous studies of expression of foreign proteins in *E. coli* have identified several parameters that can contribute to high level expression and can facilitate the recovery of biologically active product. We have utilized expression vectors that employ several important features, including: regulation of the lacUV5 promoter by the lactose operon repressor; a strong ribosome binding site from bacteriophage T7; a mutation in the replication control region of the plasmid to increase copy number; and a mutation to limit the expression of the antibiotic resistance protein. We have specifically explored the effects of the latter two features on the production of CNTF in *E. coli*.

12.2.1. Expression of Rat CNTF

12.2.1.1. Effect of Copy Number

Analysis of protein synthesis in lactose-induced cultures of *E. coli* W3110lacIqF−/pRPN11 by gel electrophoresis revealed the relatively weak expression of an approximately 24,000 kDa polypeptide, the anticipated size for rat CNTF, that was absent in induced control cultures of bacteria carrying the pCP93 vector (FIG. 18). Extracts of cells carrying pRPN11 also contained significant levels of CNTF activity. Notably, in induced cultures of *E. coli* W3110lacIqF−/RPN12, which differs from pRPN11 only by the presence of the copy number mutation cop1, the production of CNTF was increased to approximately 30 to 50% of total cellular protein (FIG. 18). Thus, the fivefold increase in the copy number of pRPN12 relative to pRPN11 resulted in a 30 to 50-fold increase in the levels of recombinant protein (Table IV). This effect of the cop1 mutation has been documented with other recombinant proteins (Buell, G. and Panayotatos, N. 1987. In "From Gene to Protein: Steps Dictating the Maximal Levels of Gene Expression", Reznikoff, W. S. and Gold, L. eds Butterworths, Stoneham, Mass.).

12.2.1.2. Effect of Antibiotic Resistance

In previous studies on the expression of recombinant proteins in *E. coli*, it was observed that synthesis of the antibiotic resistance protein encoded by the vector interfered with optimal recombinant protein production. This interference was attributed to competition by the two genes for the limiting synthetic machinery of the cell (Panayotatos, N., 1988, Gene 74:357–363). To further test this hypothesis, and potentially to improve the levels of CNTF production, the B-lactamase gene in pRPN12 was replaced with the kanamycin resistance (kanR) gene either under the transcriptional control of its native promoter (prpn37), or under the control of a weaker mutant promoter (pRPN38).

Analysis of protein levels in induced cells hosting pRPN37 indicated that rat CNTF constituted 10 to 20% of total cellular protein and that the kanR protein was synthesized at approximately one half of that level. In contrast, in cells hosting pRPN38, which bears the mutant kanR promoter, CNTF constituted 50 to 70% of total cellular protein, whereas the kanR protein was undetectable (FIG. 18 and Table IV). The significantly higher expression of CNTF observed with pRPN38 presumably results directly from the decrease in the level of expression of the antibiotic resistance gene. As observed and discussed with other is recombinant proteins expressed with these vectors at high levels (Panayotatos, N., 1988, Gene 74:357–363), minimizing the strength of the kanR promoter minimizes competition for the apparently limited synthetic capacity of the cell.

12.2.2. Expression of Human CNTF

The relative levels of human CNTF expression obtained with several vectors are shown in FIG. 18 and are summarized in Table IV. The maximal levels with each vector were lower than the levels observed for the analogous vectors carrying the rat gene, but the overall pattern was the same; a 30 to 50-fold increase was again observed with the higher copy number (cop1) plasmids, and the maximal levels were again obtained with the combination of high copy number and low expression of kanamycin resistance. For the expression of human CNTF, the effect of reduced kanR (pRPN39 vs pRPN40) is somewhat less striking than the effect on rat CNTF expression (pRPN37 vs pRPN38). This was expected, since competition of the two transcription units only becomes evident when the synthetic machinery of the cell becomes limiting, i.e. at extremely high levels of recombinant protein.

The level of rat CNTF production in *E. coli* reported here is exceptionally high. This apparently results from a favorable combination of several factors, including the use of a moderately strong promoter, a strong ribosome translational initiation signal, a vector plasmid that is maintained stably at a relatively high copy number, and the minimal synthesis of the selective antibiotic resistance protein. In addition, recombinant protein production is determined by the physical properties of the protein itself, and its stability in the host. In this respect, rat CNTF appears to be particularly amenable to expression in *E. coli*. Human CNTF is also expressed very efficiently, although to somewhat lower levels.

12.2.3. Purification of Rat and Human CNTF

Figure 19A:
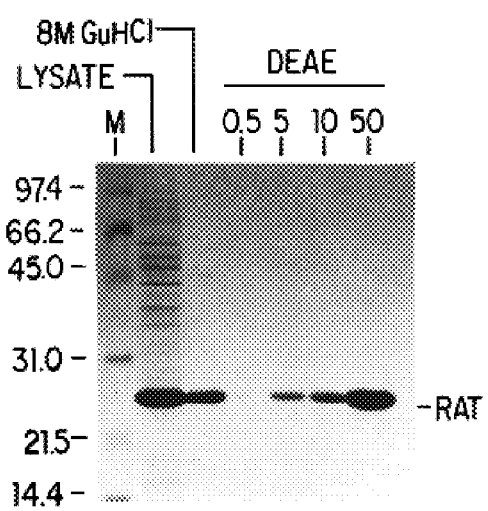
Figure 19B:
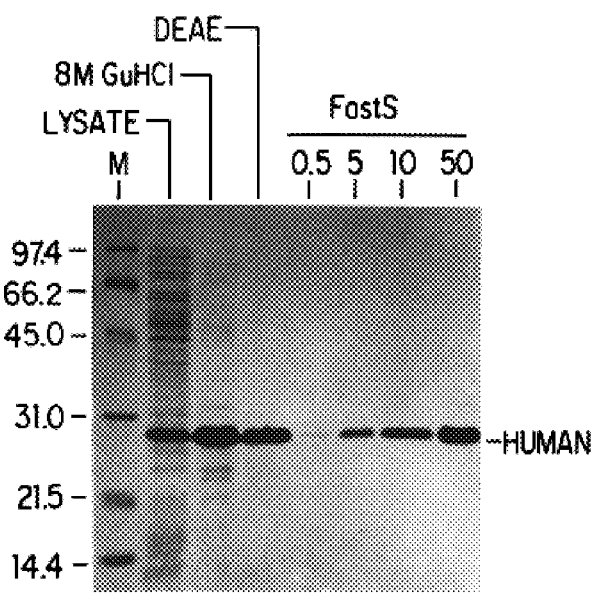

Like other recombinant proteins expressed at high levels in *E. coli*, CNTF was found mostly in insoluble inclusion bodies; 85 to 90% of the rat and 60 to 70% of the human protein was resistant to extraction by neutral buffer. Extraction and solubilization of CNTF and other (mostly hydrophobic) proteins trapped in inclusion bodies was effected with 8 M guanidinium chloride. Subsequent slow removal of guanidinium by dialysis led to precipitation of the hydrophobic host proteins and left in solution rat CNTF at better than 95% purity and human CNTF at better than 90% purity (FIG. 19). At this point, a single chromatography step (DEAE Sephacel) was sufficient to purify recombinant rat CNTF to better than 99%, as determined from the relative intensities of intentionally overloaded polyacrylamide gels (FIG. 19A), and by HPLC analysis. In part because of the weaker affinity of the human protein for DEAE Sephacel, it was necessary to add a second chromatography step (Fast S) in order to achieve better then 99% purity (FIG. 19B).

12.2.3.1. Yield

Given the estimated expression levels and assuming that the total protein content of the wet cell pellet is 5 to 15% protein by weight, the theoretical yield would be 30 to 90 mg rat CNTF and 15 to 45 mg human CNTF per gram wet cell pellet. The actual yield was found to be about 20 mg for rat CNTF and about 6 mg for human CNTF. Most of the loss in the case of the human protein is due to solubles CNTF extracted and discarded during the preparation of inclusion bodies.

12.2.3.2. Characterization

Recombinant CNTF, both rat and human, prepared by the above procedures was better than 99% pure. The proteins had very low pyrogenicity (! 5 ng/mg protein) by the Limulus Amebocyte Lysate test (Associates of Cape Cod). Furthermore, as discussed below, they were found to be biologically active at the picomolar level.

The recombinant rat and human CNTF proteins were treated with BrCN, and the N-terminal and C-terminal peptides were identified and subjected to amino acid composition and/or sequence analysis. The analyses of the N-terminal peptides revealed that in both the rat and human proteins the N-terminal amino acid was recovered quantitatively as alanine. This implies that the initiating methionine was quantitatively removed, as is generally the case in *E. coli* when the second residue is the non-bulky amino acid alanine. By contrast, the N-terminus of CNTF purified from rat sciatic nerve is blocked, and presumably retains the terminal methionine residue.

At the carboxyl end, the expected sequence of the terminal BrCN peptide was obtained for recombinant human CNTF. By contrast, amino acid composition analysis of the C-terminal peptide of rat CNTF indicated that while it had the expected composition, it lacked an expected tyrosine residue, and had an extra asparagine. DNA sequence analysis revealed a point mutation causing a tyrosine to asparagine substitution at codon 193; this apparently arose during copying of a cloned rat CNTF cDNA by PCR to construct the original expression vector pRPN11. We have established that the mutation lies in a region of CNTF non-essential for biological activity.

Rat and human CNTF have the same number of amino acids (calculated MW 22,780 and 22,700 respectively, after removal of N-terminal methionine) and share extensive parts of their sequences. Yet, on both reducing and non-reducing SDS-polyacrylamide gels, human CNTF migrates somewhat slower than rat CNTF (FIG. 19). This difference in mobility between two molecules similar in structure and identical in length probably reflects some unusual structural constraint in the human protein.

12.2.4. Biological Activity

Recombinant rat CNTF purified by the above procedure was fully active. FIG. 20 shows dose-response curves of dissociated, neuron-enriched cultures of E8 chick embryo ciliary ganglia obtained with CNTF purified from rat sciatic nerve (Stockli et al., Nature 342:920–923) and with recombinant rat CNTF. Activity of the protein purified from sciatic nerve was detectable at 5 pg/ml, and maximal neuronal survival was seen at 1 to 2 ng/ml ($EC_{50}$=80 pg/ml). In the same assay, purified recombinant rat CNTF was found to be active at 2 pg/ml and saturation was observed at 0.5 to 1.0 ng/ml ($EC_{50}$=35 pg/ml or 1.5 pM). Thus, the purified recombinant rat CNTF was at least as active as native protein purified from sciatic nerve.

In parallel experiments, purified recombinant human CNTF was assayed for biological activity. Initially, explants of embryonic day 10 (E10) chick DRG were used for rapid and semi-quantitative detection of CNTF activity in *E. coli* lysates. In the presence of CNTF, fiber outgrowth was observed, while in the absence of exogenous neurotrophic factor there was little or no outgrowth from control ganglia (FIGS. 21A, B). The maximum fiber outgrowth at saturating levels of CNTF was about 50–75% of that seen with saturating levels of NGF.

A more specific assay measures neuronal survival in dissociated, neuron-enriched cultures of E8 chick ciliary ganglia. After 48 hr in control cultures, almost all neurons had degenerated (FIG. 21C), whereas at least 60–70% of the neurons plated in the presence of saturating levels of CNTF survived and elaborated long neurites (FIGS. 21D, E). These specific effects on ciliary neurons were observed with sub-nanogram amounts of crude bacterial cell lysates and with purified recombinant protein. From such experiments conducted with increasing amounts of pure protein it was determined that recombinant human CNTF was found to be as active as rat CNTF towards chick ciliary neurons.

The expression and purification of CNTF described here could readily be scaled up for pharmaceutical production. This may be of significance, in light of the recent demonstration that CNTF can promote the survival of injured motor neurons in experimental animals (Sendtner et al., 1990, Nature 345:440–441).

TABLE IV

| Plasmid | Common Features* | Special Features* | CNTF** | Amp or kanR** |
|---|---|---|---|---|
| pRPN11 | lac.rbsl.ratCNTF | amp.cop+ | 1–2 | <0.5 |
| pRPN12 | lac.rbsl.ratCNTF | amp.cop1 | 30–50 | 1–2 |
| pRPN37 | lac.rbsl.ratCNTF | kan0.cop1 | 5–10 | 5–10 |
| pRPN38 | lac.rbsl.ratCNTF | kan1.cop1 | 50–70 | <0.1 |
| pRPN32 | lac.rbs1.humCNTF | amp.cop+ | 1–2 | <0.5 |
| pRPN33 | lac.rbs1.humCNTF | amp.cop1 | 10–20 | 1–2 |
| pRPN39 | lac.rbs1.humCNTF | kan0.cop1 | 15–25 | 5–10 |
| pRPN40 | lac.rbs1.humCNTF | kan1.cop1 | 25–35 | <0.1 |

*lac: lacUV5 promoter; rbs1: ribosome binding site; ratCNTF, humCNTF: rat or human CNTF gene; amp: ampicillin resistance gene; kan0, kan1: wild type or mutated kanR genes; cop+, cop1: normal or high copy number plasmid.
**as percent of total cellular protein

13. EXAMPLE: EFFECTS OF MODIFIED AND TRUNCATED CILIARY NEUROTROPHIC FACTOR PROTEIN ON BIOLOGICAL ACTIVITY

13.1. Materials and Methods

13.1.1. Construction of Parental Expression Vectors

Genetic engineering of the parental rCNTF expression vectors pRPN11, pRN37, and pRPN40 are described in sections 12.1.1.1.1., 12.1.1.1.3. and 12.1.1.2.2.

13.1.2. Construction of Modified Human Ciliary Neurotrophic Factor Vectors

Plasmid pRPN108 was generated by replacing the DNA sequence between the unique AatII and NheI restriction sites in pRPN33 with a fragment carrying the exact same sequence modified at two positions located 15 bp upstream from the NheI site. This was achieved with a synthetic oligodeoxyribonucleotide "3' primer" that spanned the NheI site and included three residues that replaced the TGT cysteine codon with the GCA codon for alanine. This 3' primer was used in combination with a 5' primer spanning the AatII site to obtain the desired sequence from pRPN33 by polymerase chair reaction (PCR). Thus, pRPN108 is identical to pRPN 33, except for the alanine codon for amino acid 17 of hCNTF (FIG. 22).

Plasmid pRPN109 was generated from pRPN33 in the exact same manner as pRPN108, except that the 3' primer that spanned the NheI site included two residues that converted the TGT cysteine codon into the AGT codon for serine. Thus, pRPN109, is identical to pRPN108, except for the serine codon for amino acid 17 of hCNTF (FIG. 22).

Plasmid pRPN59 was generated by removing the DNA sequence between the unique restriction sites BamH1 and NruI in pPRN33. In pRPN59, the hCNTF gene sequence is interrupted following the 185th codon and the ensuing sequence codes for 10 additional amino acids not corresponding to hCNTF and a translation-termination codon (FIG. 22).

Plasmid pRPN112 was generated in the course of engineering pRPN40 from pRPN33 (MS2) when the orientation of the restriction fragment carrying part of the hCNTF gene between AseI sites was inverted. In pRPN112, the hCNTF gene is interrupted immediately after 145th codon and the ensuing sequence introduces two codons; one for an amino acid (leucine) not corresponding to hCNTF and a translation-termination codon (FIG. 22).

Plasmid pRPN82 was generated by inserting a PCR fragment ending at BstX1 sites and coding for the last 133 amino acids of hCNTF into the BstX1 site of a gene coding for a protein non-homologous to CNTF. In pRPN82 the resulting fusion protein consists of the first 35 amino acids of the foreign protein followed by 2 glycine residues and 133 residues of hCNTF (FIG. 22).

13.1.3. Construction of Modified Rat Ciliary Neurotrophic Factor Vectors

Plasmid pRPN65 was generated by inserting between the unique restriction sites SacI and NruI of pRPN12, a PCR fragment designed so as to introduce a translation-termination codon immediately following the 165th codon of rCNTF (FIG. 22).

Plasmid pRPN110 was generated by replacing the DNA sequence between the unique Nhe1 and Eagl restriction sites in pRPN12 with a fragment carrying the exact same sequence modified at the single nucleotide that converts the TAT tyrosine codon to the AAT codon for asparagine. This was achieved with a 3' primer that extended from the position to be mutated to the 3' end of the rCNTF gene and was followed by the sequence recognized by Eagl. This 3' primer was used in combination with a 5' primer spanning the Nhel site, to obtain the desired sequence from pRPN12 by PCR. In pRPN110, the rCNTF gene encodes a protein identical to that encoded by rat DNA (FIG. 22).

13.1.4. Biological Assay of Ciliary Neurotrophic Factor Activity

Biological activity was assayed on dorsal root ganglia and/or dissociated ciliary neurons was determined as described in section 12.1.6. Soluble protein was extracted from induced bacteria hosting each plasmid by the "rapid" protein extraction method described in section 12.1.3.

13.2. Results and Discussion

The results of assays for biological activity showed that the modified hCNTF proteins encoded in pRPN108 and pRPN109, as well as the truncated protein encoded in pRPN59, were as active as the full length protein encoded in the parental plasmid pRPN33. In contrast, the truncated protein encoded in pRPN112 was inactive.

These results indicate that the unique cysteine residue which is shared by the human, rat and rabbit CNTF sequences at position 17 can be modified without obvious loss of activity. Similarly, the last 15 amino acids of hCNTF are not necessary for activity. In contrast, removal of the last 55 amino acids from the carboxyl terminus of hCNTF abolishes activity. Therefore, a critical region for active hCNTF lies in the region between amino acids 146 and 186.

Results with the truncated and modified rat CNTF proteins are consistent with this interpretation and further narrow the region critical for CNTF activity. Removal of the last 35 amino acids in the protein encoded by pRPN65 inactivated the protein, whereas replacement of the tyrosine with an asparagine residue at positon 193 had no effect on activity. These results further define the limits of the region critical for CNTF activity to the sequence between amino acids 166 and 186.

14. EXAMPLE: ADDITIONAL EFFECTS OF CNTF ON VENTRAL SPINAL CORD NEURONS

14.1. Materials and Methods

14.1.1. Experimental Animals

Sprague-Dawley rats (HSD or Zivic-Miller) were used for all experiments. Pregnant rats (E14) were sacrificed as described in 10.1.1.

14.1.2. Tissue Culture Techniques

Spinal cords were removed aseptically from rat embryos as described in 10.1.2. The cord tissues were minced into small pieces and incubated in 0.1% trypsin (GIBCO) and 0.01% deoxyribonuclease type 1 (Sigma) at 37° C. for 20 minutes. Trypsin solution was then removed, rinsed and replaced with medium consisting of 45% Eagle's minimum essential medium (MEM), 45% Ham's nutrient mixture F12 (F12), 5% fetal calf serum (GIBCO), 5% horse serum (GIBCO) glutamine (2 mM), penicillin G (0.5 U/ml), and streptomycin (0.5 ug/ml). This was then mechanically dissociated twice by gentle trituration through a Pasteur pipet in the same medium, and the supernatants were pooled and filtered through a nylon filter (Nitex, Tetko; 40 um). Total cell number yielded was determined by hemocytometer counting in the presence of trypan blue. Dissociated ventral cells were then plated at a density of approximately 50,000 cells/cm$^2$ on dishes coated with poly-L-ornithine (10 ug/ml) and laminin (5 ug/ml). Treatments were given on the day of plating, except for delayed addition experiments in which treatments were given on days 2 or 6. Cultures were maintained at 37° C. in 95% air/5% $CO_2$ atmosphere at nearly 100% relative humidity. Culture medium was changed every 3 to 4 days. A mitotic inhibitor, cytosine arabinoside (Ara C; 0.5 uM), was added on day 2 to reduce the number of nonneuronal cells. On day 7, cells were harvested for measurements of choline acetyltransferase (CAT; Fonnum, 1975 J. Neurochem. 24:407–409) and protein (Bradford, 1976, Annal. Biochem. 72:248–254) levels or fixed in 4% paraformaldehyde for NF assay (Doherty et al., 1984, J. Neurochem. 42:1116–1122) and immunocytochemistry. Some cultures were grown in defined medium consisting of 50% F12 and 50% MEM, glutamine (2 mM), insulin (5 ug/ml), transferrin (100 ug/ml), progesterone (20 nM), putrescine (10 uM), and sodium selenite (30 nM) (Bottenstein and Sato, 1979, PNAS 76:514–517). In these cultures sera-containing medium was replaced with defined medium on day 1.

14.1.3. Neurofilament (NF) Assay

After fixation of the cells in 4% paraformaldehyde at 4° C. for 2 hours, the cultures were then permeabilized and blocked according to the procedures described in Doherty et al. (1984, J. Neurochem. 42:1116–1122). Neurofilament protein was detected using a monoclonal antibody RT97 (Wood and Anderton, 1981, Biosci. Rep. 1:263–268) at a 1:1000 dilution. The reaction product was visualized using O-phenylenediamine (OPD) as a substrate and optical density was measured at 490 nm.

14.1.4. Choline Acetytransferease (CAT) Assay

Cultures were harvested by lysing the cells in a 20 mM Tris-HCl (pH 8.6) solution containing 0.1% Triton X-100. Two microliters of the cell lysate was removed and assayed for CAT activity according to the micro-Fonnum procedure (Fonnum, 1975, J. Neurochem. 24:407–409). The final substrate composition consisted of 0.2 mM [1-$^{14}$C] Acetyl-CoA (NEN, 54.4 mCi/mmol), 300 mM NaCl, 8 mM choline bromide, 20 mM EDTA, and 0.1 mM neostigmine in 50 mM $NaH_2PO_4$ (pH 7.4) buffer. At these enzyme and substrate concentrations, the enzymatic reaction was linear for 90–120 minutes. The specificity of the induction for CAT was tested by the addition of a specific inhibitor of CAT activity, N-hydroxyethyl-4-(1-napthylvinyl) pyridium (HNP), during the assay (White and Cavallito, 1970, J. Neurochem. 17:1579–1589).

14.1.5. Histochemical Staining for Acetylcholinesterase (AchE)

Cholinergic cells were identified by histochemical staining for AchE by a modification of the staining method of Geneser-Jensen and Blackstadt (1971, Z. Zellforsch. 114:460–481). Following fixation of the cultures in 4% paraformaldehyde, the cells were incubated 5–6 days at 4° C. in the presence of the AchE substrate solution composed of the following: 4 mM acetylthiocholine iodine, 2 mM copper sulfate, 10 mM glycine, and 10 ug/ml gelatin in 50 mM acetate buffer (pH 5.0). Visualization of the reaction product was accomplished as previously described (Hartikka and Hefti, 1988, J. Neurosci. 8:2967–2985).

14.1.6. Fractionation of Ventral Horn Cells by Metrizamide Density Gradient

The fractionation procedure (Dohrman et al., 1986, Dev. Biol. 118:209–221) was a modification of the method described by Schnaar and Schaffner (1981, J. Neurosci. 1:204–207). Metrizamide was dissolved in F12:MEM(1:1) medium, and a step gradient consisting of 3 ml 17% metrizamide, 3 ml 12% metrizamide and 3 ml 8% metrizamide was prepared. The following steps were all carried out at 4° C. The ventral horn cell suspension (2.5 ml) obtained as described previously was layered over the step gradient, the tube was centrifuged at 2500×g for 20 minutes using a swing-out rotor. Centrifugation resulted in three layers of cells at the 0–8% (fraction I), 8–12% (fraction II) and 12–17% (fraction III) interfaces. The cells from each interface were collected in a small volume (about 1 ml), plated, treated, and assayed as described. Neurons from fraction I were maintained in conditioned medium derived from cultured spinal cord cells.

14.2. Results and Discussion

14.2.1. General Morphologies of Cultures

Ventral horn cells grown in sera-containing medium resulted in mixed neuron-glia cell cultures. After 24 hours, glia flattened out and began to proliferate, while only a few neurons started to extend neurites. After 48 hours, however, many neurons elaborated neurites and displayed a characteristic phase-bright soma (FIG. 23). After the addition of Ara C on day 2, nonneuronal cells began to die and float off, leaving a neuron-enriched culture containing about 5% glia. In defined medium, cultures also contained about 5% glia which could be further reduced by Ara C treatment. In metrizamide gradient-purified motor neuron horn cultures (Fraction I), there was virtually no glia and over 90% of the neurons were large cholinergic neurons.

14.2.2. Effects of CNTF on Neurofilament (NF) Levels

To assess the effects of CNTF on neurons, NF levels were measured. A 2.0-fold increase in NF content was found in the CNTF-treated (10 ng/ml) ventral horn cultures as compared to untreated controls. NGF did not produced any significant effect. (FIG. 24). This suggests that CNTF promotes survival and/or neurite outgrowth in cultured ventral neurons.

14.2.3. Effects of CNTF on Survival of AChE-Containing Neurons

In order to determine whether the increase in NF levels reflects an increase in neuronal survival or neurite outgrowth, histochemical staining for AchE was performed, since the majority of the neurons in ventral horn cultures are cholinergic motorneurons. A 2.5-fold increase in AchE-positive neurons in CNTF-treated (10 ng/ml) cultures was found, as compared with untreated controls. NGF appeared to have a small effect. These results suggest that CNTF enhances neuronal survival, which may account for the increase in NF levels.

14.2.4. Effects of CNTF in CAT Activity

Figure 26B:
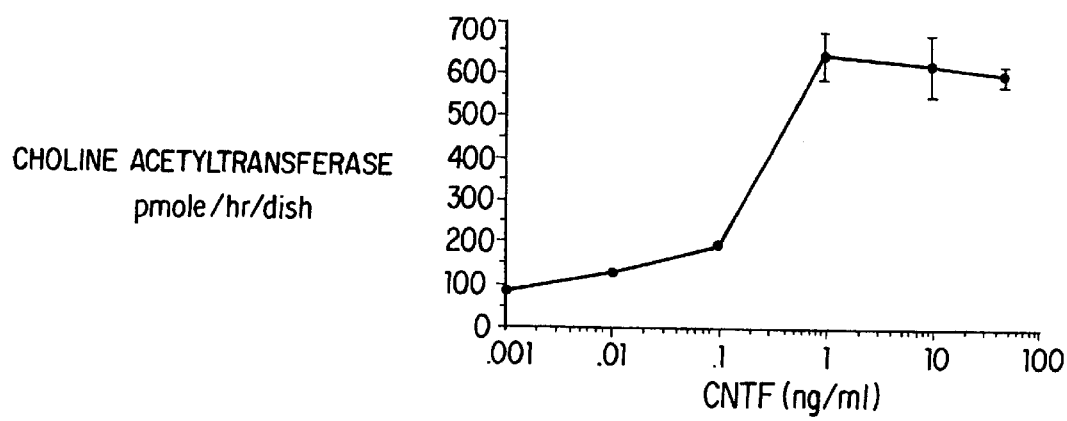

To assess the influence of CNTF on transmitter phenotypic expression, the levels of CAT activity were determined. CAT is the rate limiting enzyme for Ach synthesis. As shown in FIG. 26 addition of CNTF (10 ng/ml) produced an average of 4.0-fold increase in CAT activity after 7 days in culture, while the addition of other growth factors, such as NGF (50 ng/ml) and FGF (50 ng/ml), produced no effect. This increase in cholinergic activity is dose-dependent, and reached maximal response at CNTF concentrations of 1 ng/ml (FIG. 26B). This increase was apparent as rapidly as 3 days after treatment, and did not appear to be affected by the density of the cultures. These results suggest that CNTF also stimulates cholinergic transmitter expression, since the increase in CAT activity is 1.6-fold over that of the increase in number of cholinergic neurons; that is, the survived cholinergic neurons are expressing more Ach/neuron.

14.2.5. Delayed Addition Experiment

Ventral horn cells were divided into three groups as shown in FIG. 27. In FIG. 27A, CNTF (10 ng/ml) was added to cells at the time of plating, and cells were maintained in the presence of CNTF for 7 days. In FIGS. 27B&C, cultures were maintained without CNTF for either 2 or 6 days, and then treated with CNTF (10 ng/ml) for an additional 7 days. The delayed addition of CNTF at day 2 resulted in a diminished increase in CAT activity to 1.2-fold. After 6 days of delay, however, CNTF can no longer influence CAT activity (FIG. 27). This suggests that there is a population of CNTF-sensitive neurons which normally dies in the absence of CNTF within a few days of plating. In the presence of CNTF, these cells survive and express an increased amount of Ach.

14.2.6. Effects of CNTF on Ventral Horn Cultures in the Absence of Glia

The presence of glial cells in ventral horn cultures was reduced by 2 methods: a) treatment with antimitotic agent (AraC; 0.5 uM), and (b) use of serum-free growth medium. In either case, glial populations were reduced to about 5% of total cells, but the effects of CNTF on CAT activity remained unchanged. (FIG. 28) These results indicate that the effect of CNTF on CAT activity is not likely to be mediated via glia, but is a direct response from the neurons.

14.2.7. Effects of CNTF on Metrizamide Gradient-Purified Motorneurons

The ventral horn cultures were already enriched with cholinergic neurons. To assure the homogeniety of the cultures, the motorneurons were further purified from ventral cord cultures by density gradient. A step metrizamide gradient permits the selection of motorneurons based on their lighter buoyant densities. The resulting cultures contained greater than 90% motorneurons, as has been shown previously by Schnaar and Schaffner (1981 J. Neurosci. 1:204–207). In the purified motorneuron cultures, CNTF (10 ng/ml) stimulated a 10-fold increase in CAT activity, as compared to untreated cultures. (FIG. 29) The metrizamide gradient is able to separate a possible contaminating pool of small cholinergic preganglionic sympathetic neurons from the large motorneurons. The results demonstrate that CNTF promotes survival and stimulates cholinergic expression in the motorneurons.

15. EXAMPLE: EFFECT OF CILIARY NEUROTROPHIC FACTOR ON HIPPOCAMPAL CULTURES

15.1. Materials and Methods

15.1.1. Hippocampal Cell Cultures

Hippocampi were dissected from E18-19 rat embryos of Sprague-Dawley rats, and collected in F10 medium. The tissues were minced, rinsed twice with F10 medium (Gibco) and trypsinized with 0.25% trypsin (Gibco) for 20 minutes at 37° C. Trypsin was inactivated by the addition of a serum-containing medium composed of minimal essential medium (MEM) supplemented with fetal calf serum (FCS, 10%), glutamine (2 mM), penicillin (25 U/ml) and streptomycin (25 ug/ml). Dissociated cells obtained by gentle trituration were collected and centrifuged at low speed (500 rpm) for 30 seconds. The centrifugation was repeated twice, and the cell pellets were then resuspended in serum-containing medium. The cells were then plated onto 6 mm wells or 35 mm dishes that were coated with polyornithine (10 ug/ml) and laminin (10 ug/ml). In most of the experiments, the cells were plated at a low density of approximately 71,000 cells/cm². Five to six hours following the plating of cells, medium was changed to a serum-free medium containing 1% N3 and penicillin-streptomycin (25 units/ml and 25 ug/ml, respectively), at which time CNTF was added. Medium was changed every three to four days, with re-addition of the factor.

To obtain neuron-enriched cultures, cytosine arabinoside (Ara-C, 0.3 uM) was added for a period of 24 hours. Under such condition, the hippocampal cultures contain approximately 5–10% glial cells, as assessed by GFAP immunohistochemistry.

15.1.2. Assay for GAD Enzyme Activity

GAD enzyme activity was determined according to the method of Kimura and Kuriyama (1975, Jpn J. Pharm. 25:189–195) by measuring the release of $^{14}CO_2$ from L-[1-$^{14}$C] glutamic acid. Cells on 35 mm dishes were lysed with 30 ul of a solution containing 50 mM $KH_2PO_4$ (pH 7.2) and 0.25% Triton X-100, scraped and collected. Five microliters of the cell lysate was assayed for GAD enzyme activity. In a typical assay, the reaction mixture contained 0.57 mM of L-[1-$^{14}$C] glutamic acid (NEN, NEC-715, 52.6 mCi/mmol), glutamic acid (3 mM), pyridoxal phosphate (0.2 mM) and AET (1 mM), in a $KH_2PO_4$ buffer (50 mM, pH 7.2). Under these reaction conditions, the enzyme reaction was found to be linear for up to 2.5 hours. The incubation proceeded for a period of 2 hours at 37° C., and was terminated by injecting 25 ul of 8N $H_2SO_4$ into the reaction mixture. The incubation was then continued for another 60 minutes. $^{14}CO_2$ released was trapped in Hyamine base solution, and was counted.

15.1.3. Measurement of Neurofilament Protein

Neurofilament protein was quantitated according to the method of Doherty et al. (1984, J. Neurochem. 42:1115–1122), as is described in Section 14.1.3.

15.1.4. Measurement of High Affinity GABA Uptake

High-affinity GABA uptake was measured using a modified procedure of Tomozawa and Appel (1986, Brain Res. 399:111–124. Cells were washed in the GABA uptake buffer containing 140 mM NaCl, 2.6 mM KCl, 1 mM $KH_2PO_4$, 1 mM $Na_2HPO_4$, 6 mg/ml glucose, 1 mM $MgCl_2$, 1 mM $CaCl_2$, 0.1% BSA. Following washing, cells were incubated with the GABA uptake buffer for 5 minutes at 37° C. $^3$H-Gaba (NEN, NET-191X, 111.4 Ci/mmol) was then added at a final concentration of 12 nM, and incubation was carried out at 37° C. for 10 minutes. Cells were then kept on ice, and washed three times with the uptake buffer. Cells were incubated with 0.14 N NaOH for 2 hours at room temperature, and H-GABA in the extract was counted.

$^3$H-GABA uptake was found to be linear for up to at least 30 minutes. Uptake of GABA into non-neuronal cells was inhibited by the additional of 2 mM B-alanine, whereas uptake specific for neurons is verified by inhibition with nipecotic acid at 1 mM.

15.1.5. Immunohistochemical Staining for GAD or GABA

Cells were fixed with 4% paraformaldehyde for 30 minutes at room temperature, washed with PBS. For GAD staining, cells were permeabilized by sequential rinsing with 50%, 70% and 50% ethanol. The cultures were blocked by sequential rinsing with PBS containing 5% normal rabbit serum for one hour, and incubated with sheep anti-GAD antibody 1440 at a 1:6000 dilution) overnight at 4° C. Following three rinses with PBS, cells were then incubated with biotinylated rabbit anti-sheep antibody at a 1:400 dilution for at least 90 minutes at room temperature. For GABA staining, cells were permeabiized with Triton X-100 (0.25%) in Tris-HCl (0.1M, pH 7.3), and blocked with 10% normal goat serum for 90 minutes, prior to incubation with rabbit anti-GABA antibody (1:5000) ovenight at 4° C. Following three rinses with PBS, cells were then incubated with biotinylated goat anti-rabbit antibody at a 1:200 dilution for at least 90 minutes at room temperature. GAG- or GABA imminoreactive cells were visualized by using the Vectastain ABC kit (Vector Labs).

15.1.6. Immunohistochemical Staining for Neuron-Specific Enolase (NSE)

Following fixing with 4% paraformaldehyde, cells were blocked with 10% normal goat serum (NGS) in PBS containing 0.1% Triton X-100. The cells were then incubated with the primary antibody (rabbit anti-NSE, 1:5000) overnight at 4° C. The cells were then incubated with the secondary antibody (goat anti-rabit, 1:200 dilution) for at least 90 minutes at room temperature. NSE-immunopositive cells were visualized using the Vectastain ABC kit (Vector Labs).

15.1.7. Histochemical Staining for Calbindin

Cells were rinsed twice with PBS, and fixed with 4% paraformaldehyde for 30 minutes at room temperature. Following washing with 1% normal horse serum (NHS) and blocking with 5% NHS in PBS for 1 hour at room temperature, the cells were incubated with a mouse anti-calbindin antibody (1:1000 dilution) in 1% NHS overnight at 4° C. The cells were then rinsed three times with 1% NHS and incubated with the secondary antibody (horse anti-mouse at 1:400 dilution) for 90 minutes at room temperature. Immunoreactive cells for calbindin were visualized by using the Vectastain ABC kit (Vector Labs).

15.1.8. Histochemical Staining for Acetylcholinesterase

Histochemical staining for acteylcholinesterase was performed according to the procedures of Geneser-Jensen and Blackstadt (1971, Z. Zellforsch 114:460–481). Cells were washed three times with PBS, and fixed with 4% paraformaldehyde at room temperature for 30 minutes. The fixed cells were then incubated with a reaction mixture containing 50 mM acetate buffer (pH 5.0), 4 mM acetylthiocholine iodide, 2 mM copper sulfate, 10 mM glycine and 10 ug/ml gelatin. Nonspecific cholinesterases were inhibited by including 0.2 mM ethopropazine in the incubation medium. Specificity of the cholinesterase staining was verified by the addition of neostigmine at 5 uM. At the end of a 7-day incubation, gelatin was dissolved by brief incubation at 37° C. The cells were washed with water, treated for one minute with 1.25% $Na_2S$, and washed again with water. They were then treated for 1 minute with 1% $AgNO_3$, washed with water and PBS.

15.1.9. Ciliary Neurotrophic Factor

The CNTF used in all assays was recombinant rat CNTF, expressed and purified as described in Example Section 12 supra.

15.2. Results

When hippocampi were taken at the developmental age of E18 and put into culture, the majority of the neuronal population consisted of postmitotic pyramidal neurons. Five to six hours after plating, neurons already extended neurites, and there was evidence of cell-cell contact following 1 day in culture. Phase-bright cells with long processes were evident.

Figure 30A:
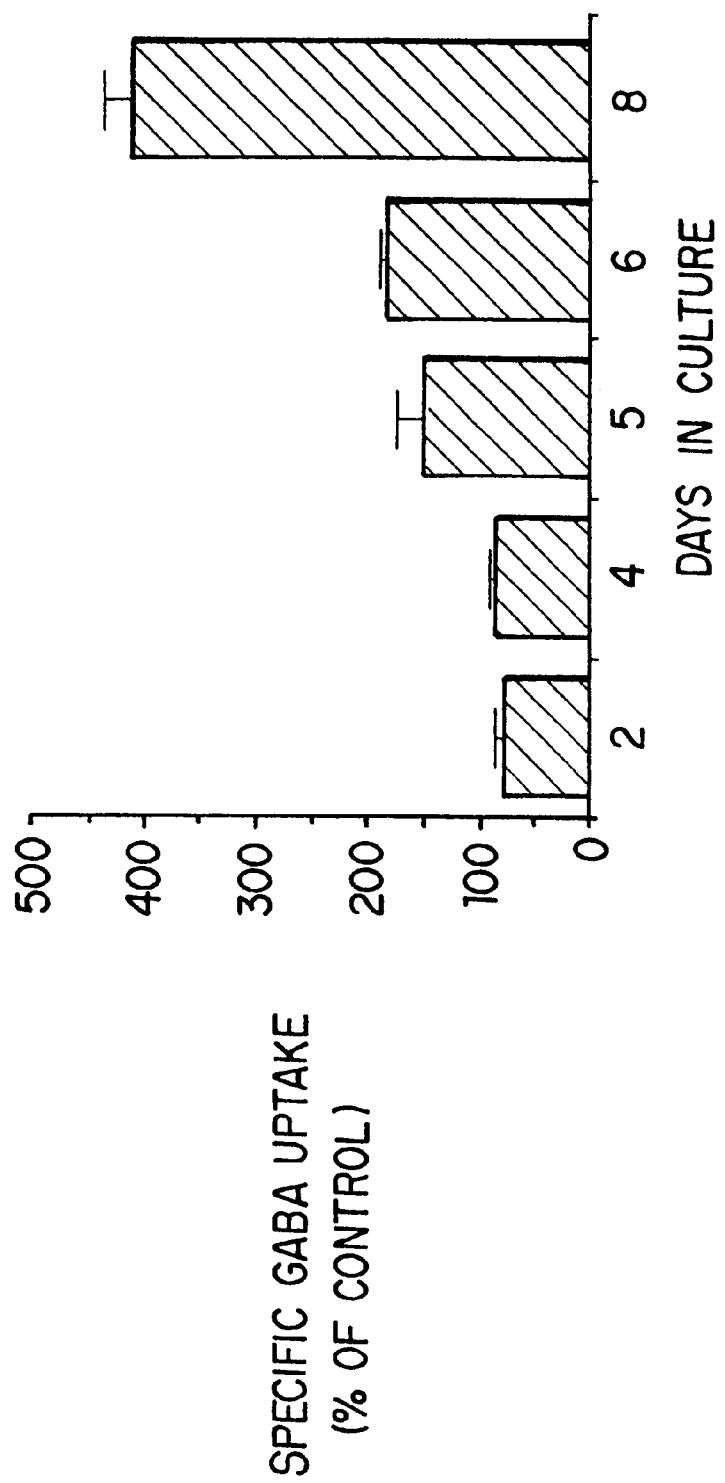
Figure 30B:
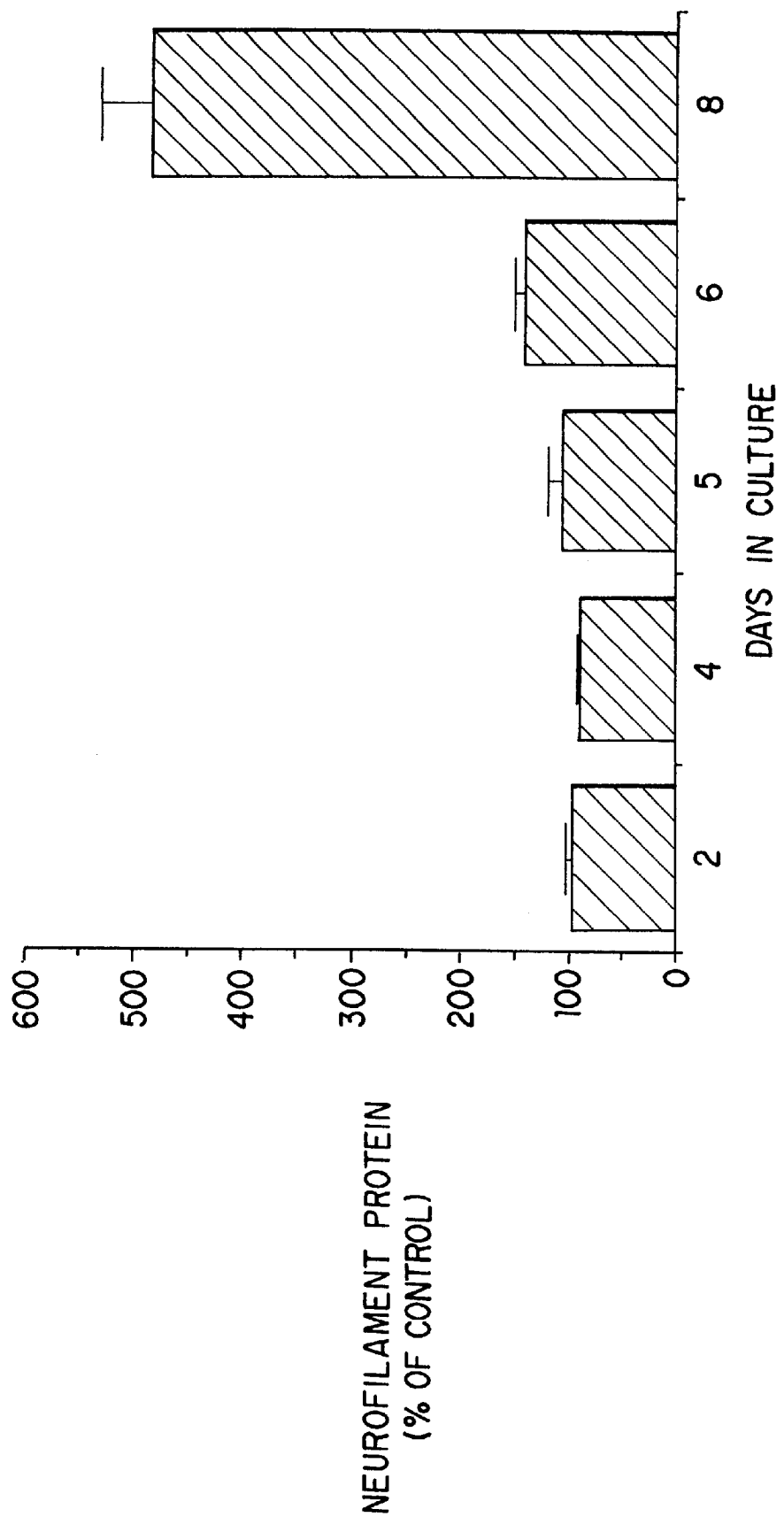

Hippocampal neurons were cultured at a low density (approximately 71,000 cells/cm$^2$) in the presence or absence of CNTF for various periods of time. Continuous treatment of hippocampal cultures with CNTF (10 ng/ml) produced an increase in the ability of the cells to take up $^3$H-GABA (FIG. 30). The time course of CNTF-induced increase in specific neuronal GABA uptake was slow, as shown in FIG. 30A. CNTF (10 ng/ml) treatment produced a small increase in GABA uptake by culture day 6, and a maximal increase of approximately 4-fold, compared to untreated controls, was observed 8 days after CNTF addition. A longer culture period of up to 11 days did not produce a larger increase. To further assess the effect of CNTF on hippocampal neurons in culture, neurofilament protein was quantitated using an antibody against neurofilament protein (RT97) followed by an ELISA assay. It was determined that neurofilament was only slightly increased by culture day 6, and was maximally increased by approximately 5-fold on day 8 (FIG. 30B). A similar time course for both GABA uptake and neurofilament protein was also observed at 1 ng/ml of CNTF.

Figure 31A:
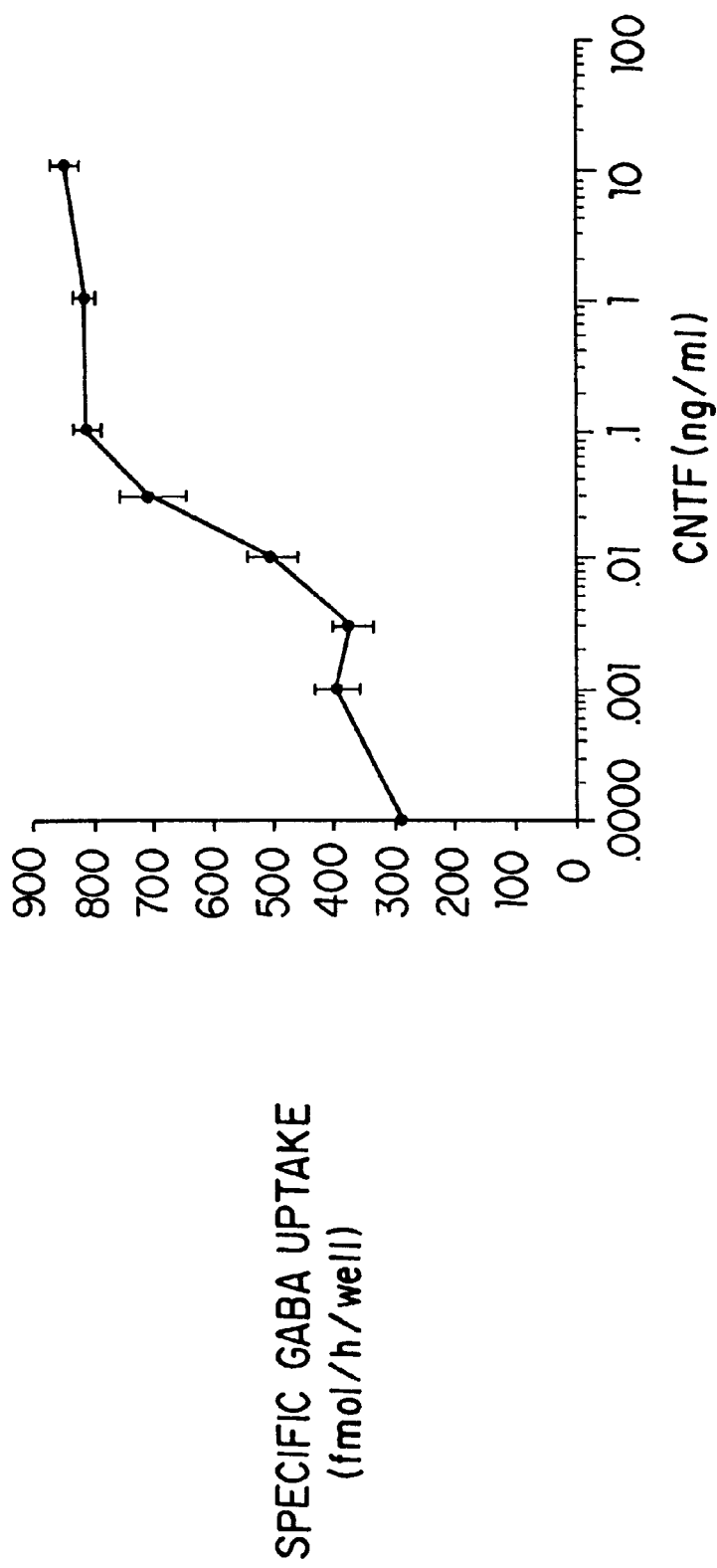
Figure 31B:
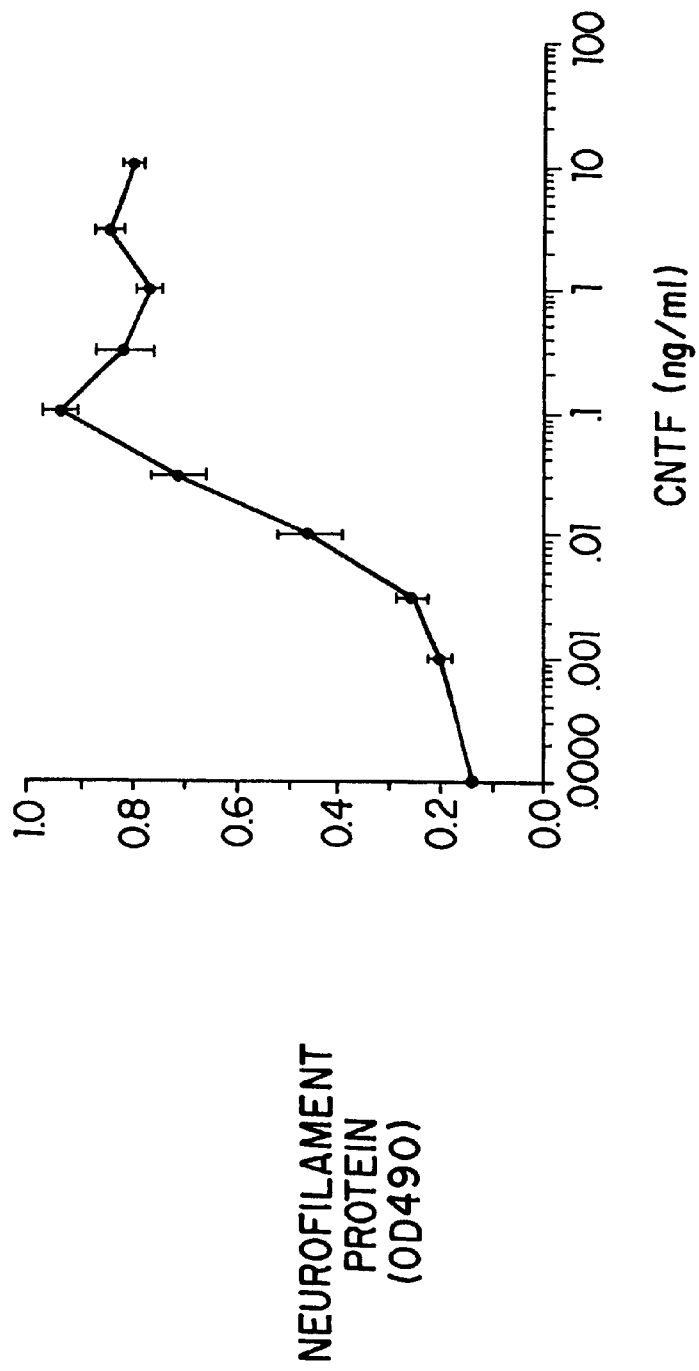

The effect of CNTF appeared to be dose-dependent, as shown in FIG. 31. Specific neuronal GABA uptake was increased at 0.01 ng/ml, and was maximally increased by approximately 3-fold in cells treated with 0.1 ng/ml of CNTF for 8 days (FIG. 31A). Higher concentrations of up to 50 ng/ml of CNTF did not result in a bigger increase in GABA uptake. Similarly, neurofilament protein in CNTF-treated cultures was also increased in a dose-dependent manner, reaching a plateau at 0.1 ng/ml of CNTF (FIG. 31B). Higher concentrations of up to 50 ng/ml of CNTF did not increase the amount of neurofilament protein further.

As an additional way to examine the effect of CNTF on GABAergic neurons, GAD enzyme activity was measured in cultures incubated in the presence of CNTF for 8 days. It was found that CNTF produced an increase in GAD enzyme activity in hippocampal neurons in a dose-dependent fashion (FIG. 31C). The shape of the dose-response curve obtained is similar to that observed for GABA uptake and neurofilament protein. A maximal increase of 3.8-fold in GAD enzyme activity was observed with 0.1 ng/ml of CNTF.

Figure 32A:
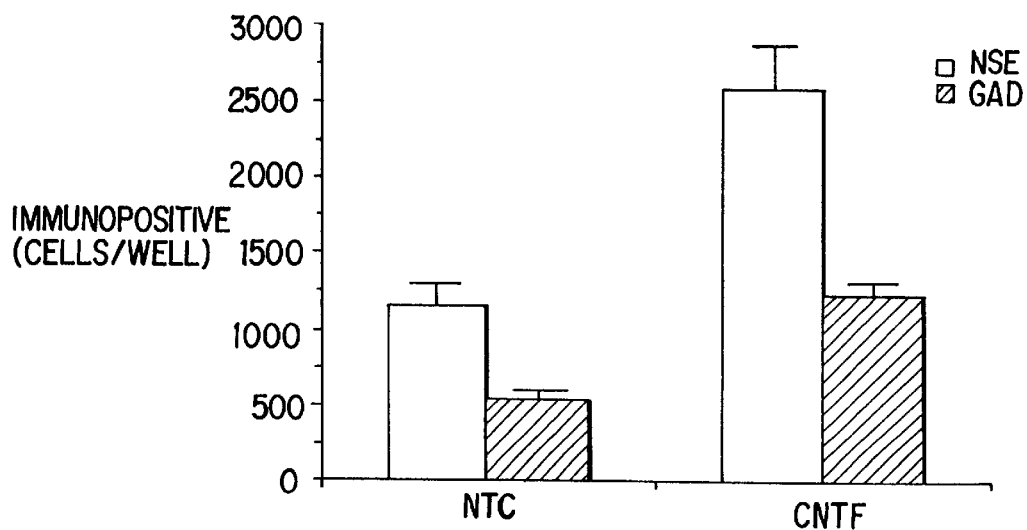
Figure 32B:
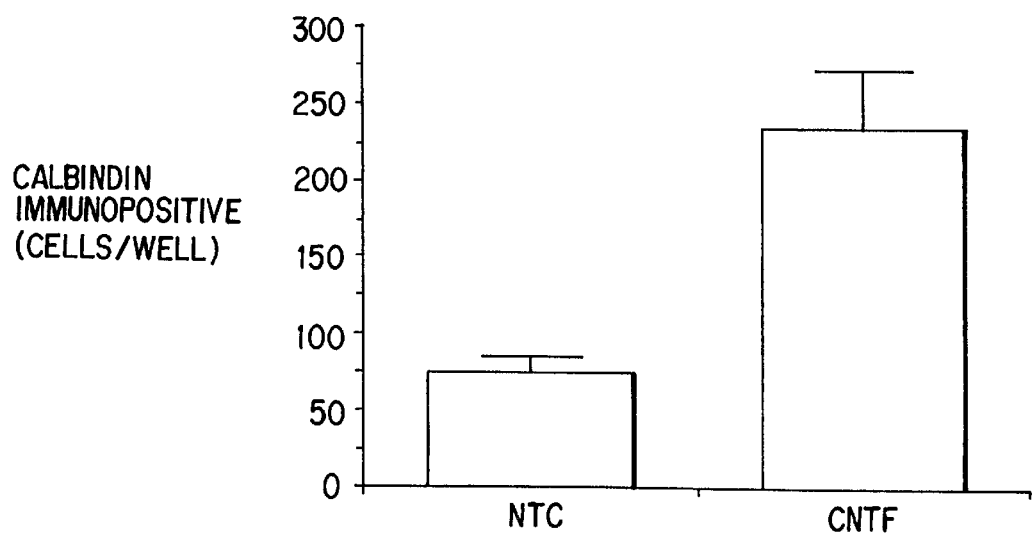
Figure 33B:
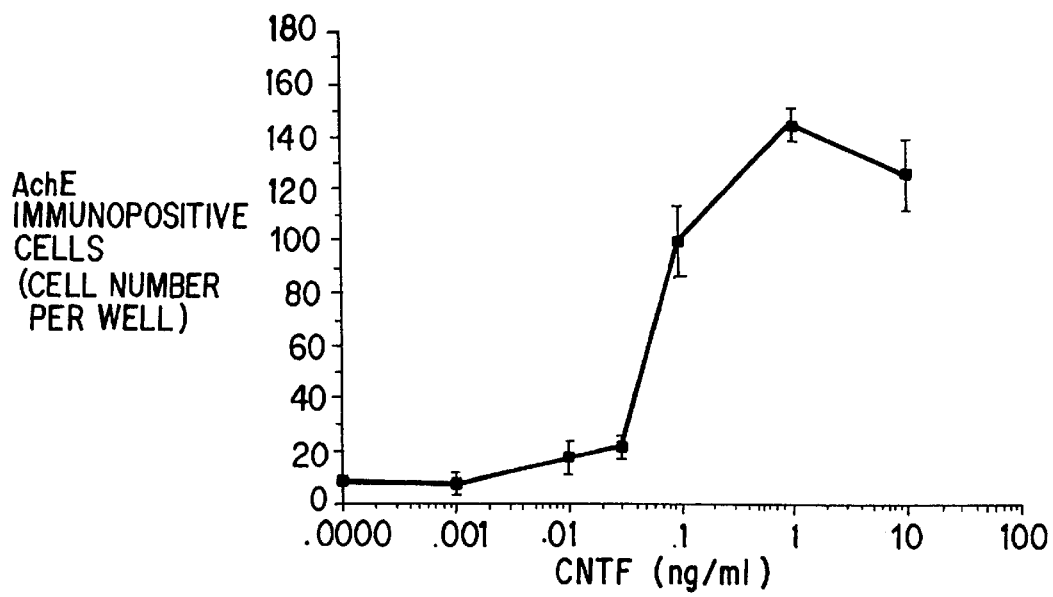

To examine whether the effect of CNTF on GAD enzyme activity was due to an induction in the enzyme activity or due to a survival effect on GABAergic neurons, the number of GAD-immunoreactive neurons was determined in cells grown in the presence or absence of CNTF. At a concentration of 10 ng/ml, CNTF increased the number of NSEand GAD-positive neurons by 2.2- and 2.3-fold, respectively (FIG. 32A). Immunohistochemical staining using an antibody against GABA yielded similar results. (FIG. 33A) Calbindin has been localized to a subpopulation of hippocampal neurons, including dentate gyrus, CA1 pyramidal neurons and some interneurons (Balmbridge and Miller 1982, Brain Res. 245:223–229). CNTF (10 ng/ml) treatment of low-density hippocampal cultures resulted in a 3-fold increase in calbindin-immunopositive cells (FIG. 32B). After 8 days in culture, the number of acetylcholinesterase positive cells was also increased by approximately 17 fold in CNTF-treated cultures compared to controls. (FIG. 33B).

Figure 34A:
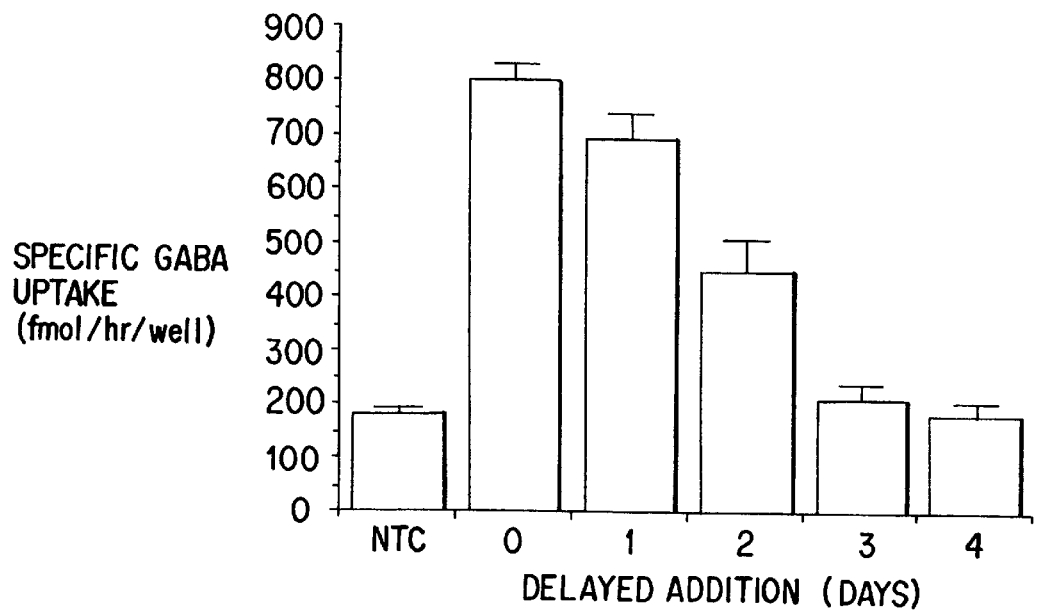
Figure 34B:
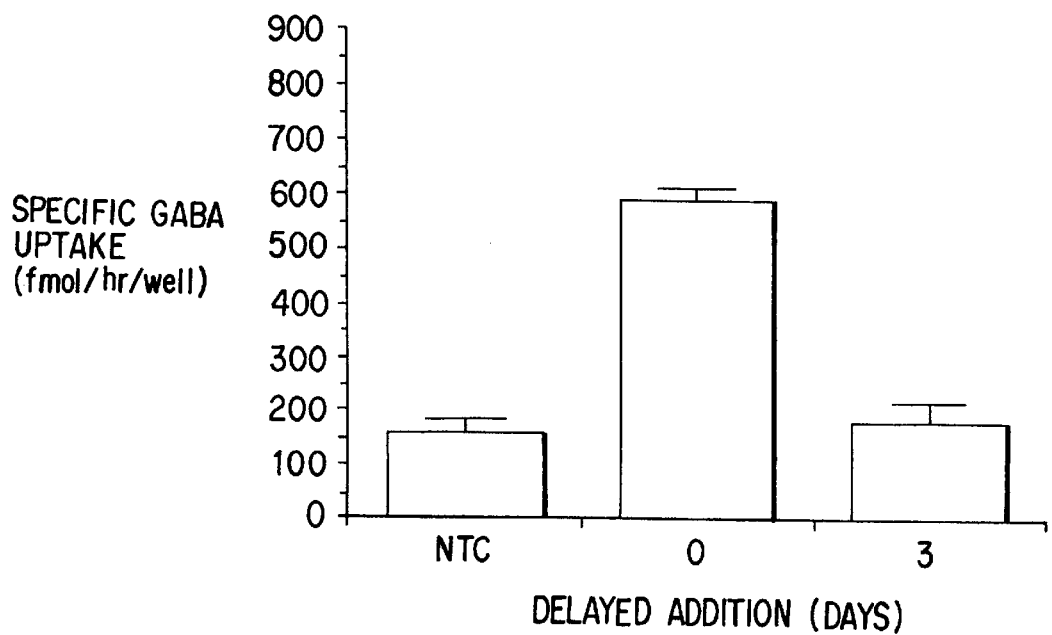
Figure 35A:
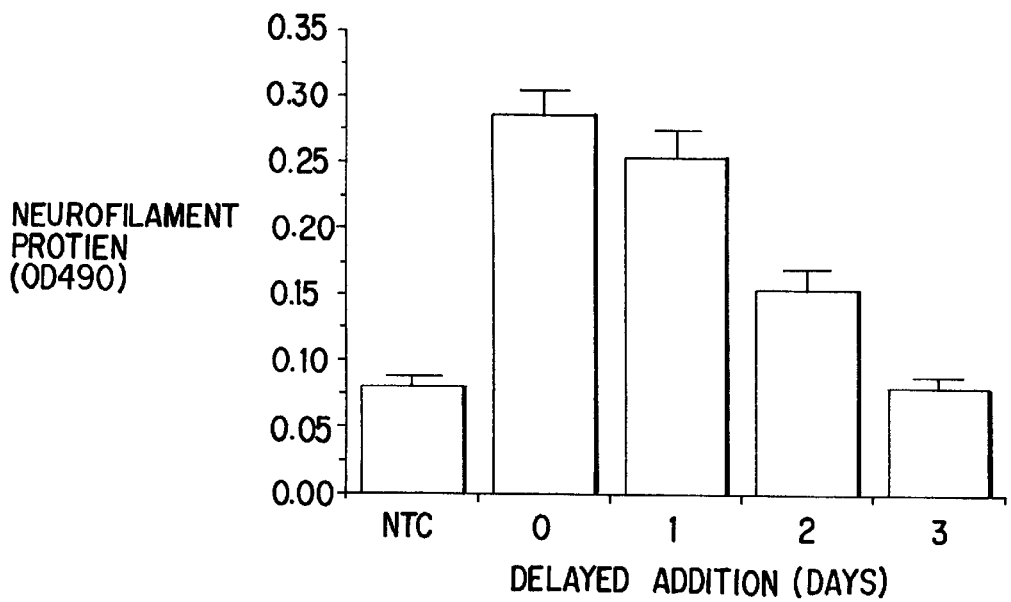
Figure 35B:
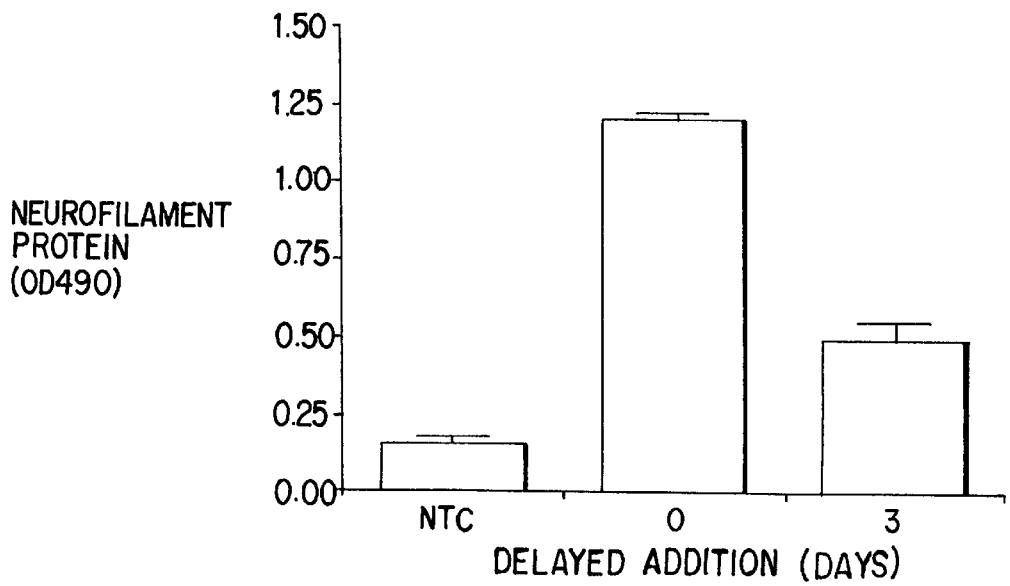

To provide further evidence that CNTF was acting as a survival factor to rescue GABAergic neurons in culture rather than acting to induce the Gabaergic phenotypic trait, delayed addition experiments were performed. CNTF (10 ng/ml) was added at various times after plating, and GABA uptake or neurofilament protein levels were determined on the eighth day in culture. As shown in FIG. 34A, when the addition of CNTF was delayed by one day, CNTF-induced increase in GABA uptake, when assayed 7 days later, was lowered. When the addition of CNTF was made on the third day after plating, CNTF no longer produced an increase in GABA uptake. CNTF-induced increase in neurofilament protein was similarly diminished when the addition of CNTF was delayed by 3 days (FIG. 35A). To rule out the possibility that this observation was due to an insufficient time of exposure to the factor, the following experiment was performed. CNTF (10 ng/ml) was added to the cells on the third day in culture, and the cells were treated with the factor for 8 days prior to the measurement of Gaba uptake and neurofilament protein. Under such conditions, CNTF failed to induce increase in Gaba uptake and the effect on neurofilament protein was much reduced (FIGS. 34B, 35B).

Astrocytes have been shown to be a rich source of a number of neurotrophic factors, including NGF. To examine the possibility that the effect of CNTF was via the release of such factors from glial cells, rather than acting directly on the neurons, CNTF-induced increase in GABA uptake was examined in neuron-enriched cultures. As shown in FIG. 36, in AraC-treated cultures, CNTF produced a 2.4-fold increase in Gaba uptake when compared to untreated controls. The stimulation in GABA uptake was similar in neuron-glia mixed cultures (−AraC) or in neuron-enriched cultures (+AraC). In addition, the dose-response curve for CNTF in AraC-treated cultures was slightly shifted to the left in that the concentration of CNTF required for a maximal response was lower (0.03 ng/ml compared to 0.1 ng/ml).

Figure 37A:
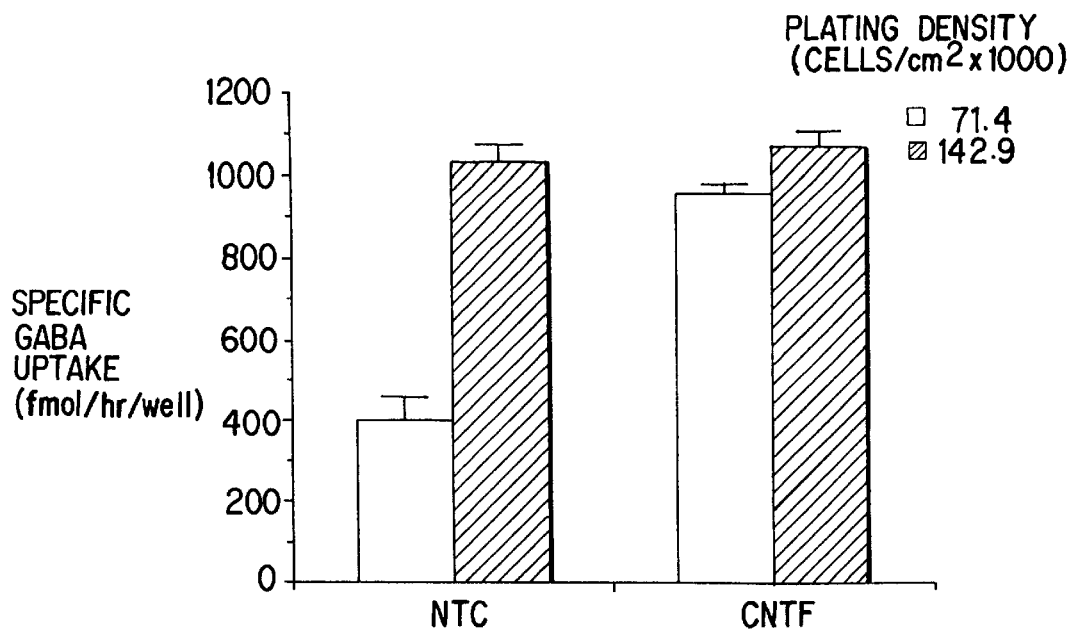
Figure 37B:
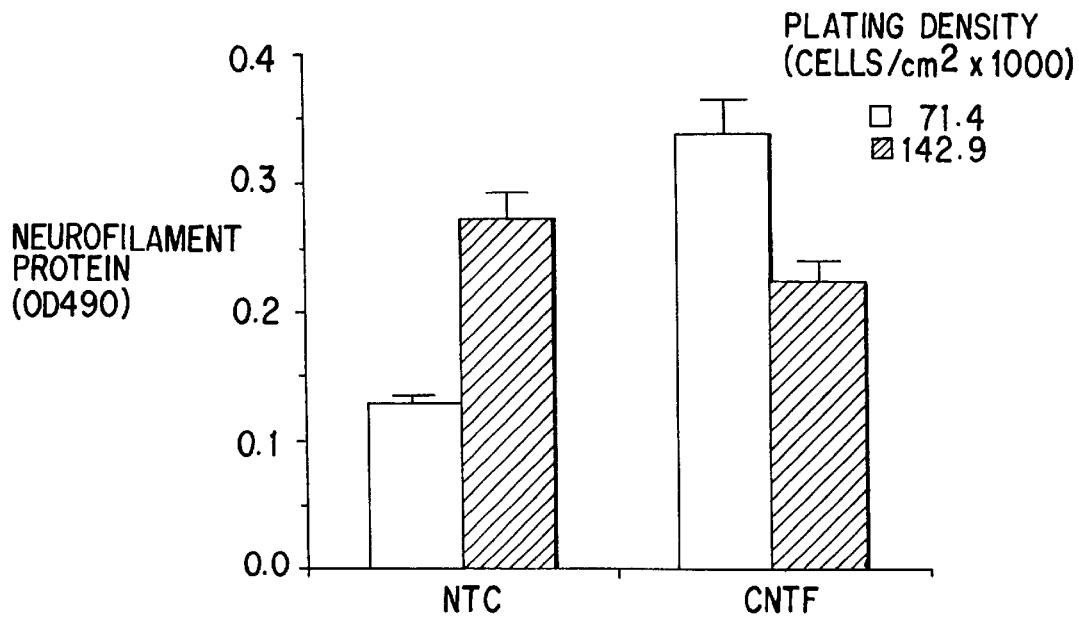

The effect of CNTF on GABAergic neurons was dependent on the density at which the cells were plated. At a low plating density of 71,000 cells/cm$^2$, CNTF (10 ng/ml) produced an approximately 2.6-fold increase in Gaba uptake (FIG. 37A). At higher plating density (143,000 cells/cm$^2$), CNTF failed to induce a significant increase in Gaba uptake at a saturating concentration (10 ng/ml). The effect of CNTF on the level of neurofilament protein was similarly dependent on cell density (FIG. 37B). This may be due to an elevated level of neurotrophic factors in high density cultures. Hippocampal neurons in culture have previously been shown to be sensitive to glutamate neurotoxicity (Mattson, M. P. et. al. (1988) J. Neurosu. 8:2087–2100). We have assessed the neurotoxic effects of various concentrations of glutamate (10–1000 μM) by means of a calorimetric MTT assay, as shown in FIG. 38. At a concentration of 1 mM, glutamate reduced cell survival to approximately 10%. In the presence of CNTF (10 μg/ml), cell survival following exposure to glutamate was enhanced.

15.3. Discussion

CNTF has been shown to enhance the survival and growth of several distinct neuronal populations in culture. In addition, a CNTF-like activity has been shown to induce differentiation of type-2 astrocytes from glial progenitor cells in culture (Hughes et al., 1988, Nature 335:70–73, Lillien et al., 1988, Neuron 1:485–494). We have provided evidence for a novel effect of CNTF in the CNS, i.e., CNTF supports the survival of neurons isolated from E18 hippocampus in vitro. Treatment of hippocampal neurons with CNTF results in an increase in Gaba uptake accompanied by an increase in GAD enzyme activity. Neurofilament protein levels of the hippocampal cultures was similarly increased in the presence of CNTF. Dose response studies show a correlation among these various markers, and a maximal effect of CNTF reached at 0.1 ng/ml of CNTF. Higher concentrations of CNTF did not appear to produce a larger effect.

The effect of CNTF could be explained by selective induction of GABAergic phenotypic markers. However, the results of the delayed addition strongly argue for a survival effect of CNTF. We found that when the addition of CNTF was delayed by 3 days, it could no longer exert its effect on the GABAergic cells. Although neurofilament protein levels were still significantly increased, the effect is much less than that observed when CNTF was added on day 0.

Density-dependence effects of CNTF show that at high density, the cells did not seem to require CNTF for survival. This could be due to local release of endogenous neurotrophic factors from neurons or astrocytes, or due to cell-cell interactions. It has been shown that hippocampal neuronal survival is enhanced in the presence of astrocytes (Banker and Cowan, 1977, Brain Res. 126:397–425). It is possible that the factor involved is CNTF or a member of the neurotrophin family. In neuron-enriched cultures, the effect of CNTF on GABA uptake and neurofilament protein was not affected. The data strongly argue against a role of astrocytes in the action of CNTF, and suggests that the effect is mediated via a direct action on the neurons. Using a myc-tagged CNTF ligand and an antibody to myc, we have evidence for the presence of receptors for CNTF on the neurons.

The survival-promoting activity of CNTF on hippocampal neurons did not appear to be limited to GABAergic neurons. We have evidence that the number of acetylcholinesterase-immunopositive cells is also increased in the presence of CNTF. The intensity of the AchE-histochemical staining was much more pronounced in CNTF-treated cultures. This may have important implications in a possible role of CNTF as a retrograde survival and differentiation factor for the cholinergic neurons in the medial septum.

The expression of two general markers of the neuronal phenotype, NSE and NF, was increased in the presence of CNTF. The measurement of NF protein accumulation was accomplished by using an enzyme-linked immunoadsorbent assay. The monoclonal antibody (RT97) used recognized predominantly the 200 KDa form of the NF protein triplet, and to a monor extent, the 150 KDa subunit. It has previously been shown that the level of binding of RT97 could serve as an arbitrary index of neurite outgrowth, in particular, axonal outgrowth, for cultured neurons (Doherty et al., 1984, Neurosci. Lett. 51:55–60). Eight day old hippocampal cultures maintained with CNTF showed a denser and complex network of processes. This increase in the relative amount of NF protein could simply be secondary to improved neuronal survival. Alternatively, CNTF may have a selective effect on induction of neurite outgrowth.

The specificity of the survival-promoting activity of CNTF has been addressed by examining the actions of other neurotrophic factors known to be present in hippocampus (Maisonpierre et al., 1990. Science 247:1446–1451). Consistent with previous observation that NGF is not a survival factor for hippocampal neurons, we were not able to detect any effect of NGF on GABAergic neurons. Another member of the neurotrophin family, BDNF, also does not seem to promote the survival of Gabaergic neurons in culture. On the other hand, bFGF has been shown to be an important survival factor in the hippocampus (Wallicke et al., 1986. PNAS USA 83:3012–3016) and has been implicated to function as a neurotrophic factor in the CNS (Morrison et al. 1986 PNAS USA 83:7537–7541; Anderson et al. 1988 Nature 332:360–361). Similar to bFGF, CNTF is active at very low concentrations.

Hippocampus has been shown to be affected in several neurodegenerative disorders, including Alzheimer's disease. The underlying mechanisms that lead to selective degeneration of the hippocampal formation is not understood. It has been hypothesized that the excitatory amino acid neurotransmitter glutamate may play a role in the disease process. The demonstration that CNTF can support hippocampal neuronal survival in vitro may have important implication for designing therapeutic approaches for the neurodegenerative diseases. It will be important to determine whether CNTF can protect hippocampal neurons against glutamate neurotoxicity, as has been observed for FGF (Mattson et al. 1986, PNAS 83:7537–7541). Messenger RNA for CNTF has recently been detected in hippocampus by Northern blot analysis (Masiakowski, personal communication). The cell type specificity of CNTF synthesis in vivo has not yet been determined. The physiological role of CNTF in the hippocampus during development in vivo remains to be established, but in view of the present findings, CNTF may be an endogenous neurotrophic factor with a potential role in regulating neuronal survival in the hippocampus.

16. EXAMPLE: NOVEL MONOCLONAL ANTIBODIES TO CILIARY NEUROTROPHIC FACTOR AND A TWO-ANTIBODY SANDWICH ASSAY FOR HUMAN CILIARY NEUROTROPHIC FACTOR

16.1. Materials and Methods

16.1.1. Generation of Monoclonal Antibodies to Ciliary Neurotrophic Factor

16.1.1.1. Immunization Protocol

CB6F1/J female mice were inoculated with 10 to 40 μg recombinant human CNTF (prepared as described in EXAMPLE 12) in complete Freund's adjuvant, and then reinoculated with rCNTF in complete Freund's adjuvant every three weeks up to about 6 months.

16.1.1.2. Hybridoma Formation

Spleen cells from immunized mice were fused with SP2/0 myeloma cells at a ratio of 2:1 (lymphocytes:myeloma cells) using PEG 4000, and then cultured in complete RPMI with 2% HAT (hypoxanthine, aminopterin, and thymidine) at a cell density of about $10^5$ lymphocytes per well to select for hybridomas.

17.1.1.3. Screening of Hybridomas for CNTF Reactivity

Antibodies reactive with human CNTF (hCNTF) were identified initially by enzyme-linked immunosorbent assay (ELISA) with recombinant hCNTF bound to plastic assay dishes. The antibodies were characterized further by ELISA and Western immunoblotting for their ability to react with recombinant hCNTF, recombinant rat CNTF (rCNTF), and altered forms of hCNTF as described infra.

17.1.2. Preparation of Variants of Human CNTF

Variant forms of human CNTF were generated via expression and purification of the vectors described in section 13.1.2. Briefly, human CNTF variant protein #112, was obtained via expression of vector pRPN112, and lacks the 55 amino acid residues on the carboxyl-terminal end of human CNTF. Protein #49 was generated using pRPN59, and lacks the carboxyl terminal 15 amino acids of hCNTF. Protein #82 is a fusion protein in which the first 66 amino acids of human CNTF are deleted, and the remainder of the molecule is fused to an unidentified human protein (FIG. 22).

16.1.3. Methodology for Two-Site Immunoassay

In order to determine the amount of CNTF in samples of biological material, it would be advantageous to develop an immunological assay for the protein. One sensitive and convenient immunoassay is the two-antibody sandwich method [see, for example, E. Harlow and D. Lane, *Antibodies: A Laboratory Manual*, 1988, Cold Spring Harbor Laboratory, Cold Spring Harbor, N.Y., pages 578–583]. In this method a first antibody is bound to a solid support and allowed to react with a solution containing the antigen of interest; a second antibody, usually directed to a different epitope on the antigen, is then allowed to react with the antigen bound to the first antibody, and the amount of bound second antibody (which should be directly proportional to the amount of bound antigen) is quantitated. In one embodiment of this method, both the first and second antibodies are monoclonal antibodies.

The two-site assay developed for human CNTF is presented schematically in FIG. 40. Essentially, an affinity-purified secondary antibody specific for one subclass of mouse immunoglobulin G (IgG2b in the case shown) was adsorbed to an assay plate and used to capture the first monoclonal antibody (RP3-12, a murine IgG2b) from spent culture supernatant of hybridoma cells. Human CNTF was then added and allowed to bind to the first monoclonal antibody. The second anti-CNTF monoclonal antibody of a different subclass from the first (RP12-2, a murine IgG1) was then added, again from unfractionated hybridoma culture supernatants, and allowed to bind to any CNTF captured by the first monoclonal antibody. Any RP12-2 molecules bound were then detected using affinity-purified secondary antibody specific for murine IgG1, conjugated to alkaline phosphatase, followed by incubation with the phosphatase substrate para-nitrophenyl phosphate, cleavage of which generates a colored reaction product (measured by absorbance at 405 nm).

16.2 Results and Discussion

Monoclonal antibodies of the class represented by RP3-12 and RP3-17 were generated from the same fusion experiment using splenocytes from a single immunized mouse. Both RP3-12 and RP3-17 failed to react with either of the two carboxyl-terminal deletions of hCNTF tested, and also do not bind rat CNTF as shown in Table V. However, they do react with the fusion protein #82, in which the carboxyl-terminus of hCNTF is retained. Thus, these antibodies recognize an epitope (or closely spaced epitopes) located near the carboxyl-terminal end of hCNTF, within or overlapping the segment of 15 carboxyl-terminal amino acid residues deleted in hCNTF protein #59. By contrast, monoclonal antibodies RP12-2 and RP12-9 react with both hCNTF protein #59 and hCNTF protein #112, as well as with the fusion protein #82. Both of these antibodies therefore must recognize epitopes located between approximately amino acids 66 and 145 of hCNTF. The mapping data thus indicate that the epitopes recognized by RP12-2 and RP12-9 must lie at least about 40 amino acid residues upstream of those recognized by RP3-12 or RP3-17 (FIG. 22). The RP12-2 and RP12-9 antibodies differ in their ability to recognize rat CNTF (Table V) implying that they recognize distinct epitopes, one of which (that recognized by RP12-9) is probably well conserved between rodents and primates. The ability of all of these monoclonal antibodies to bind to denatured CNTF in a Western immunoblotting assay suggests that they recognize simple epitopes comprised of contiguous or very closed spaced amino acid residues, rather than conformational epitopes.

Initial experiments were carried out to determine whether pairs of the monoclonal antibodies to hCNTF were suitable for the development of a two-antibody sandwich for this ligand. An assay was designed to evaluate the antibodies at an early stage, prior to large scale production or purification of the reagents, by taking advantage of subclass-specific anti-mouse immunoglobulin reagents to immobilize one monoclonal antibody to a solid support, and to differentially detect the second "reporter" monoclonal antibody. Because of the requirement that the two monoclonal antibodies be of different subclasses, only certain pairs of monoclonal antibodies could be evaluated in ths way. Excellent results were obtained with the pair RP3-12 and RP12-2 in the two-site immunoassay described. FIG. 41 shows the results of the two-antibody sandwich assay in a titration with increasing amounts (by factors of two) of recombinant human CNTF, from 7.8 picograms per assay (50 μl at 0.156 ng/ml) to 500 picograms per assay (50 μl at 10.0 ng/ml). A convincing signal above background (0.044±0.010 absorbance units) was detectable with 15.6 picograms of human CNTF, and the assay was linear up to the highest level tested. Substitution of irrelevant mouse myeloma proteins of the appropriate subclass for either of the monoclonal antibodies (MOPC-141, an IgG2b, in place of RP3-12; or MOPC-21, an IgG1, in place of RP12-2) reduced the signal to background levels.

Thus, even using unpurified culture supernatants, an excellent two-antibody sandwich assay for human CNTF could be demonstrated with monoclonal antibodies RP3-12 and RP12-2. These monoclonal antibodies can be purified by conventional methods from supernatants of hybridoma cells grown in serum-free medium. It is anticipated that it will be entirely straightforward to develop a simpler sandwich assay in which one monoclonal antibody can be bound directly to a solid support, while the second monoclonal antibody will be directly conjugated to a reporter (e.g. radioisotope such as $^{125}$Iodine; or an enzyme such as alkaline phosphatase, horseradish peroxidase, or β-galactosidase; or a hapten such as biotin, which can be detected using labelled avidin or streptavidin), thus obviating the need for type-specific secondary antibodies.

The highly specific, sensitive antibody sandwich assay described here will have uses in many situations in which it is desirable to determine quantitatively the presence of human CNTF. For example, it can be used to monitor human CNTF during purification procedures. Similarly, the assay can be used to monitor CNTF after injection into experimental animals, to determine the tissues to which it localizes. Finally, the assay can be used to determine the levels of CNTF in human tissues and/or bodily fluids (e.g. serum or cerebro-spinal fluid) in healthy and diseased individuals. Because CNTF is found intracellularly in nerves, and has neurotrophic activity, it has been suggested that the protein might be released in response to various types of neuronal injuries or diseases. Thus, the level of CNTF in appropriate extracellular fluids might provide a quantitative, diagnostic measure for such conditions as neuropathy and neuronal degeneration.

TABLE V

REACTIVITY OF MONOCLONAL ANTIBODIES WITH HUMAN CNTF, HUMAN CNTF DELETION MUTANTS, AND RAT CNTF

| | | ELISA | | | Western Blotting | | | |
|---|---|---|---|---|---|---|---|---|
| Clone | Subclass | hCNTF | hCNTF (59) | rCNTF | hCNTF | hCNTF (59) | hCNTF (112) | rCNTF |
| RP3-12 | IgG2b | + + | - - | - - | + + | - - | - - | - - |
| RP3-17 | IgG2a | + + | - - | - - | + + | - - | - - | - - |
| RP12-2 | IgG1 | + + | + + | - - | + + | + + | + + | - - |
| RP12-9 | IgG1 | + + | + + | + + | + + | + + | + + | + + |

17. Ciliary Neurotrophic Factor Promotes Survival of Spinal Motorneurons in Culture 17.1. Material and Methods 17.1.1. Tissue Culture Techniques Motorneuron columns were dissected under a stereomicroscope from the lumbar part of the spinal cord of chick embryos on the 6th day of embryonic development and stored in cold calcium and magnesium-free Hanks balanced salt solution supplemented with glucose (4 g/l) (HBSS). The tissues were washed with HBSS and treated with 0.03% trypsin in HBSS at 37° C. for 20 min with gentle shaking, rinsed with cold HBSS and triturated mildly in 3 steps of 8-passage agitation in 1 ml of cold 0.1% soybean trypsin inhibitor (Sigma) in HBSS through a fire-polished siliconized Pasteur pipette. Each supernatant cell suspension was filtered through 50 μm-Nylon mesh, pooled and layered onto 4 ml of cold 6.8% metrizamide (Fluka) in HBSS-25 mM HEPES (pH7.4) in a 12 ml-siliconized conical glass tube. The tube was centrifuged at 400 g for 15 min at 4° C. and the intermediate layer (0.5 ml) was collected into another siliconized tube containing 6.5 ml of cold culture medium (a mixture of glucose (4 g/l)-supplemented Leibovitz's L-15 medium (Gibco), 0.15 M sodium bicarbonate, heat-inactivated and filtered horse serum and penicillin G ($10^5$ units/ml) at the ratio of 75:15:10:0.1, freshly prepared and buffered with 5% $CO_2$.) After centrifugation at 100×g for 7 min at 4° C., the supernatant was removed and the cells were gently resuspended in culture medium and plated in Greiner 4-well culture dishes (well diameter, 10 mm; C. A. Greiner und Sohne GmbH, Nurtingen, West Germany) at 1000–2000 cells/well. The dishes had been precoated with poly-DL-ornithine (Sigma, 0.5 mg in 0.15 M sodium borate buffer (pH 8.3) overnight at 4° C., rinsed twice with phosphate-buffered saline (PBS) and subsequently coated with laminin (Gibco; 10 µg/ml in the serum-depleted culture medium) and placed in a 5% $CO_2$-incubator until cell plating (5–6 hrs). Cells were incubated at 37° C. in a humidified 5% $CO_2$- and 95% air-incubator. Samples were added one hr after plating and the culture medium changed after 24 hrs and 72 hrs. The initial cell numbers were counted 3 hrs after plating.

17.1.2. Retrograde Labeling of Motorneurons and Estimation of the Purity of the Culture of Motorneurons In some experiments motor neurons were retrogradely labeled with a fluorescent dye in vivo before cell preparation (U. Dohrman et al., 1986, Dev. Biol. 118:209–221) to identify the motor neuron cell population. A small hole was made in the shell of eggs which had been incubated for 5 days. Small pieces of rhodamine isothiocyanate crystals (Sigma) were inserted at two or three places into each hind limb thigh and the egg hole was sealed with a cellophane tape. The eggs were incubated for another 24 hrs. Some of the operated embryos were then processed for frozen sections after formaldehyde fixation. Within the spinal cord only lateral motorneuron columns were found to be labeled. The other embryos were used for cell preparation using the method described above (18.1.1). After 5 hrs in culture cells were rinsed with warm HBSS, fixed with 4% formaldehyde in PBS at room temperature for 20 min, rinsed with PBS and then mounted in glycerol-PBS (1:1) with glass coverslips. Of the total cells approximately 83% were labeled and identified as motorneurons (FIG. 42.) Most of these labeled motorneurons were large cells and the rest were intermediate-size cells. No small cells were labeled. On the other hand, in experiments in which cells were not labeled with a fluorescent dye about 70% of the total cells were large phase-bright cells with round cell somas, about 20% were intermediate-size neurons (most of them may be motorneurons) and about 10% were small immature neurons (they have neuron-like processes with growth cones but have phase-dark semi-flat cell somas). Non-neuronal cells were either not present or accounted for less than 2%. Taken together, one may conclude that at least 83% of the cells are motorneurons while the remainder consists of non-labeled motorneurons, a small number of unidentified intermediate-size neurons and about 10% immature small neurons. We also found that if labeled cells were cultured with embryonic chick muscle extract (U. Dohrman et al., 1986, Dev. Biol. 118:209–211) the fluorescence-positive cell numbers diminshed during a few days. Since the numbers of total or large cells declined much more slowly, this represents a loss and/or fading of fluorescence rather than cell death. Therefore, to estimate the survival activities of samples in routine experiments large phase-bright cells rather than fluorescent-positive cells were counted as motorneurons.

17.2. Results and Discussion

17.2.1. Effect of Ciliary Neurotrophic Factor (CNTF) on Chick Embryonic Spinal Motorneurons in Culture Most of the motorneurons died within 3 days in culture in blank controls. In the presence of recombinant rat CNTF, about 70% were alive after 3 days in culture and about 60% after 6 days in culture (FIG. 43 and FIG. 44). Since most motor neurons died within 3 days in blank controls, survival activities were estimated on day 3. The concentration-response curve of CNTF (FIG. 45) showed that the $EC_{50}$ (the concentration required for 50% survival) of CNTF was as low as about 20 pg/ml (1 pM), nearly the same as that for ciliary neurons. The significant survival activity of CNTF with a very low $EC_{50}$ strongly suggests that CNTF may play a critical role in motorneuron survival in vivo, as has been shown (see Example 11 supra; Sendtner et al., 1990, Nature 345: 440–441).

17.2.2. Survival Effects of Specific Neurotrophic Molecules and Cytokines

Of all the molecules tested, CNTF and basic fibroblast growth factor (FGF) proved to be the most potent molecules (Table VI). The survival activity of acidic FGF could be increased when the cultures were supplemented with heparin, which interferes with the proteolytic degradation of acidic FGF. Insulin-like growth factor (IGF) I and II and insulin showed minor effects. The concentration-response curves for these active molecules (FIG. 46) showed that the highest survival effects could be obtained by: (a) CNTF= 64% survival at 1 ng/ml; (b) Basic FGF=51% at 30 ng/ml; (c) Acidic FGF=18% at 300 ng/ml; (d) Acidic FGF, in the presence of 1 µg/ml heparin, =35% at 100 ng/ml; (e) IGF-I=15% at 100 ng/ml; (f) IFG-II=15% at 300 ng/ml; (g) Insulin=16% at 25 µg/ml. The $EC_{50}$ values were 0.023 ng/ml for CNTF and 0.26 ng/ml for basic FGF. For IGF I and II as well as insulin, reliable $EC_{50}$ values could not be determined, as the maximal effects were very small when compared to the controls.

The concentration of heparin was critical for the enhancement of the activity of acidic FGF. The concentrations used in the present experiments (1 µg/ml) did not seem to be maximal with respect to the enhancement of the survival activity of acidic FGF. However, higher concentrations of heparin resulted in a detachment of the neurons from the culture dishes. Even at 1 µg/ml of heparin, neuron detachment started after 3 days of incubation. βNGF, BDNF, PDGF, EGF, TGFa, TFGβ1, IL-1β, IL-3 or IL-6 or IFNc had no discernable effect even when supramaximal concentrations (with respect to biological effects on other cell types) were used. Also NT-3, a new neurotrophic molecule of the NGF-BDNF gene family, was used in these experiments. Concentrations of NT-3 protein produced by transfected Cos-cells, which supported the survival of embryonic nodose ganglion neurons in culture did not appear to have a survival effect on motoneurons.

17.2.3. Combination of CNTF, Basic FGF and IGF-I

The combination of CNTF and basic FGF at optimal concentrations resulted in a 100% survival of the motoneurons over a period of one week (Table VII). The same was true for the combination of CNTF, basic FGF and IGF-I. The effect of IGF-I was small by itself (Table VI), but became more evident when it was combined with either CNTF and/or basic FGF (Table VII).

TABLE VI

Motoneuron Survival Activities of Known Molecules

| Molecule | Concentration | Survival[a] |
|---|---|---|
| Control | | − |
| bNGF (mouse) | 10 μg/ml | − |
| BDNF (porcine) | 10 μg/ml | − |
| NT-3 | | − |
| CNTF (rat, rec.) | 500 pg/ml | +++ |
| Basic FGF (human, rec.) | 10 ng/ml | ++ |
| Acidic FGF (human, rec.) | 300 ng/ml | ± |
| Acidic FGF + Heparin | 100 ng/ml + 1 μg/ml | ++ |
| PDGF (rec.) | 5 ng/ml | − |
| EGF (mouse) | 10 ng/ml | − |
| TGFa (human, rec.) | 10 ng/ml | − |
| TGFβ1 (porcine, rec.) | 5 ng/ml | − |
| IL-1β (human, rec.) | 100 units/ml | − |
| IL-3 (mouse, rec.) | 100 units/ml | − |
| IL-6 (mouse, rec.) | 50 units/ml | − |
| IFNc (rat, rec.) | 1000 units/ml | − |
| IGF-I (human, rec.) | 100 ng/ml | ± |
| IGF-II (human, rec.) | 300 ng/ml | ± |
| Insulin (bovine) | 25 μg/ml | ± |
| Transferrin (human) | 100 lg/ml | − | a: Survival activities were assayed after 3 days in culture and estimated with − 2 + ++: −, not significantly different from control (survival: 8.3 ± 3.8%, mean ± SD, n = 18); ±, about 15–20% (statistically significant from each blank control, $p < 0.01$); ++, about 35–55%; +++, about 55–75%. The results were combined from different experiments.
rec., recombinant.

TABLE VII

Additional Effects of CNTF, Basic FGF and IGF-II

| Factors | Motoneuron survival (%)[a] |
|---|---|
| Control | 4.8 ± 1.0 |
| IGF-I (1 μg/ml) | 14.5 ± 0.5** |
| Basic FGF (30 ng/ml) | 51.9 ± 3.6 |
| CNTF (1.5 ng/ml) | 60.7 ± 5.8 |
| Basic FGF + IGF-I | 76.1 ± 4.1** |
| CNTF + IGF-I | 87.0 ± 4.5* |
| Basic FGF + CNTF | 98.2 ± 3.0 |
| Basic FGF + CNTF + IGF-I | 102.5 ± 5.3[NS] |

[a]Motoneuron survival was assayed after 3 days in culture by counting cells in the area that corresponds to 23% of each well bottom. Mean ± SEM (n = 4).
*$p < 0.05$;
**$p < 0.01$;
[NS]not significant.
The results of t-test were indicated only for the comparisons between the values with or without IGF-I because the effect of IGF-I is relatively small. The differences in any other meaningful comparisons are significant ($p < 0.01$).

18. Deposit of Microorganisms

The following recombinant bacteriophage recombinant plasmid DNA, and hybridomas were deposited with the American Type Culture Collection, 12301 Parklawn Drive, Rockville, Md. 20852:

| | | ATCC Accession No. | Date Of Deposit |
|---|---|---|---|
| plasmid | pCP-r-CNTF-C-1 | 40655 | Sep. 12, 1989 |
| plasmid | pCMV-rCNTF-C-1 | 40656 | Sep. 12, 1989 |
| bacteriophage | λhCNTF-G-1 | 40657 | Sep. 12, 1989 |
| hybridoma | RP3-12 | CRL 10531 | Aug. 16, 1990 |
| hybridoma | RP12-2 | CRL 10532 | Aug. 17, 1990 |

The following recombinant plasmid DNA were deposited with the Agricultural Research Culture Collection (NRRL), Northern Regional Research Center, 1815 North University Street, Peoria, Ill. 61604:

| | | NRRL Accession No. | Date Of Deposit |
|---|---|---|---|
| plasmid | pRPN38 | B-18700 | Aug. 16, 1990 |
| plasmid | pRPN40 | B-18701 | Aug. 16, 1990 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for producing biologically active human ciliary neurotrophic factor in bacteria, comprising the steps of
  (a) culturing a bacterial cell transformed with a bacterial expression vector comprising the DNA ATG-GCTTTCACAGAGCATTCACCGCTGAC-CCCTCACCGTCGGGACCTCTGTAGCC GCTC-TATCTGGCTAGCAAGGAAGATTCGTTCAGACC TGACTGCTCTTACGGAATC CTATGTGAAGCAT-CAGGGCCTGAACAAGAACATCAACCTG-GACTCTGCGGATGG GATGCCAGTGGCAAG-CACTGATCAGTGGAGTGAGCTGACCGAGGCAG AGCGACT CCAAGAGAACCTTCAAGCTTATCG-TACCTTCCATGTTTTGTTGGCCAGGCTCTTA GAAGACCAGCAGGTGCATTTTAC-CCCAACCGAAGGTGACTTCCATCAAGCTATA CATACCCTTCTTCTCCAAGTCGCTGC-CTTTGCATACCAGATAGAGGAGTTAATGA TACTCCTGGAATACAAGATCCCCG-CAATGAGGCTGATGGGATGCCTATTAATGT TGGAGATGGTGGTCTCTTTGAGAA-GAAGCTGTGGGGCCTAAAGGTGCTGCAGGA GCTTTCACAGTGGACAGTAAGGTCCATC-CATGACCTTCGTTTCATTTCTTCTCATC AGACTGGGATCCCAGCACGTGGGAGCCATTAT ATTGCTAACAACAAGAAAATG,
  wherein said bacterial expression vector is capable of being replicated in said bacterial cell and capable of directing expression of said DNA in said bacterial cell to produce human ciliary neurotrophic factor;
  (b) causing human ciliary neurotrophic factor to be produced in said bacterial cell; and
  (c) recovering biologically active human ciliary neurotrophic factor from said bacterial cell.

2. The method according to claim 1, wherein the bacterial cell is E. coli.

3. The method according to claim 1, wherein the bacterial expression vector is pRPN40, as deposited with the NRRL under the accession number B-18701.

4. A bacterial expression vector, comprising the DNA ATGGCTTTCACAGAGCATTCACCGCT-GACCCCTCACCGTCGGGACCTCTGTAGC-CGCTCTAT CTGGCTAGCAAGGAAGATTCGT-TCAGACCTGACTGCTCTTACGGAATCCTATGT GAAGCATC AGGGCCTGAACAAGAACATCAAC-
CTGGACTCTGCGGATGGGATGCCAGTG-
GCAAGCACTGAT CAGTGGAGTGAGCTGAC-
CGAGGCAGAGCGACTCCAAGAGAACCTTCAA
GCTTATCGTACCTT CCATGTTTTGTTGGCCAG-
GCTCTTAGAAGACCAGCAGGTGCATTT-
TACCCCAACCGAAGGTG ACTTCCATCAAGC-
TATACATACCCTTCTTCTCCAAGTCGCTGCCTT
TGCATACCAGATAGAG GAGTTAATGATACTC-
CTGGAATACAAGATCCCCCGCAATGAG-
GCTGATGGGATGCCTATTAA TGTTGGAGATG-
GTGGTCTCTTTGAGAAGAAGCTGTGGGGCCTA
AAGGTGCTGCAGGAGCTTT CACAGTGGACAG-
TAAGGTCCATCCATGACCTTCGTTTCATTTCTT
CTCATCAGACTGGGATC CCAGCACGTG
GGAGCCATTATATTGCTAACAACAAGAAAATG,
wherein said bacterial expression vector is capable of being
replicated in a bacterial cell and capable of directing expression of said DNA in said bacterial cell to produce human ciliary neurotrophic factor.

5. A bacterial expression vector according to claim 4, designated pRPN40 and deposited with the NRRL under the accession number B-18701.

6. A bacterial cell transformed within a bacterial expression vector of claim 4.

7. A bacterial cell transformed with a bacterial expression vector of claim 5.

8. A bacterial expression vector comprising expression regulatory sequences operatively linked to a nucleotide sequence which encodes CNTF, wherein said nucleotide sequence is selected from the group consisting of:

(a) a nucleotide sequence which encodes the amino acid sequence: MAFAEQTPLTLHRRDLCSRSIW-LARKIRSDLTALMESYVKHQGLNKN-INLDSVDGVP VASTDRWSEMTEAERLQEN-LQAYRTFQGMLTKLLEDQRVHFTPTEGDFHQAI HTLM LQVSAFAYQLEELMVLLEQKIPENE-ADGMPATVGDGGLFEKKLWGLKVLQELSQW TVRSIHDLRVISSHQMGISALESHJGAKDKQM, wherein J is Y or N, (b) a nucleotide sequence which encodes the amino acid sequence:
MAFTEHSPLTPHRRDLCSRSIWLARKIRSDLT
PLTESYVKHQGLNKNNNLDSADGMPVAST
DQWSELTEAERLQENLQAYRTFHVLLAR-
LLEDQQVHFTPTEGDFHQAIHTLLL
QVAAFAYQIEELMILLEYKIPRNEADGMPIN
VGDGGLFEKKLWGLKVLQELSQWTV
RSIHDLRFISSHQTGIPARGSHYIANNKKM, and (c) a nucleotide sequence which (1) hybridizes to the sequence of (a) or (b) under a hybridization condition, and (2) encodes a protein which promotes the survival of ciliary ganglionic nerve cells, wherein said hybridization condition is selected from the group consisting of conditions comprising:

(i) incubating for 12 to 18 hours in 5×SSCP and 50% formamide at 68° C., washing in 5×SSCP and 50% formamide at 42° C. for 30 minutes, and washing in 2×SSCP for 20 to 30 minutes at room temperature, (ii) incubating for 12 to 18 hours in 6×SSC, 1×Denhardt's, 50 mM EDTA (pH 8.0), 0.5% SDS and 100 μg/ml of tRNA at 68° C., washing twice in 6×SSC, 0.5% SDS at 68° C. for 20 minutes each, washing in 2×SSC at 68° C. for 20 minutes, and washing in 0.1×SSC for 2 minutes at room temperature, (iii) incubating for 12 to 18 hours in a 0.5 M sodium phosphate, pH 7.2, 7% SDS, 1% crystalline BSA and 1 mM EDTA (pH 8.0) at 68° C., washing twice in 40 mM phosphate buffer (pH 7.2), 5% SDS, 0.5% BSA (Fraction V), 1 mM EDTA (pH 8.0) for 30–60 minutes at 68° C., and washing twice in 40 mM phosphate (pH 7.2), 1 mM EDTA (pH 8.0) and 1% SDS for 30–60 minutes at 68° C., and (iv) incubating for 16 hours in 5×SSC and 50% formamide at 37° C., washing three times in chloroform for 10 minutes each, washing in 6×SSC for 10 minutes, washing in 2×SSC for 10 minutes, and washing in 2×SSC containing 20 μg/ml of pancreatic ribonuclease.

9. The bacterial expression vector of claim 8 wherein said nucleotide sequence is the nucleotide sequence of nucleotides 78 to 678 of FIG. 1(b).

10. The bacterial expression vector of claim 8, wherein said nucleotide sequence comprises:
ATGGCTTTCACAGAGCATTCACCGCT-
GACCCCTCACCGTCGGGACCTCTGTAGCC
GCTCTATCTGGCTAGCAAGGAAGAT-
TCGTTCAGACCTGACTCCTCTTACGGAATC
CTATGTGAAGCATCAGGGCCTGAACAA-
GAACAACAACCTGGACTCTGCGGATGG GAT-
GCCAGTGGCAAGCACTGATCAGTGGAGT-
GAGCTGACCGAGGCAGAGCGACT
CCAAGAGAACCTTCAAGCTTATCGTAC-
CTTCCATGTTTTGTTGGCCAGGCTCTTA GAA-
GACCAGCAGGTGCATTTTACCCCAAC-
CGAAGGTGACTTCCATCAAGCTATA
CATACCCTTCTTCTCCAAGTCGCTGC-
CTTTGCATACCAGATAGAGGAGTTAATGA
TACTCCTGGAATACAAGATCCCCCG-
CAATGAGGCTGATGGGATGCCTATTAATGT
TGGAGATGGTGGTCTCTTTGAGAA-
GAAGCTGTGGGGCCTAAAGGTGCTGCAGGA
GCTTTCACAGTGGACAGTAAGGTCCATC-
CATGACCTTCGTTTCATTTCTTCTCATC
AGACTGGGATCCCAGCACGTGGGAGC-
CATTATATTGCTAACAACAAGAAAATG.

11. A bacterial host cell transformed with the vector of claim 8.

12. A recombinant DNA method for the production of CNTF comprising:

(a) transforming a bacterial host cell with the expression vector of claim 8;

(b) culturing the bacterial host cell under conditions for amplification of the vector and expression of CNTF; and (c) harvesting the CNTF from the culture medium.

13. The method of claim 12 wherein said vector sequence comprises the nucleic acid sequence encoding CNTF as set forth as follows:
MAFTEHSPLTPHRRDLCSRSIWLARKIRSDLTPLT
ESYVKHQGLNKNNNLDSADGMPVASTDQWSEL
TEAERLQENLQAYRTFHVLLARLLEDQQ
VHFTPTEGDFHQAIHTLLL QVAAFAYQIEELMIL-
LEYKIPRNEADGMPINVGDGGLFEKKL-
WGLKVLQELSQWTV RSIHDLRFISSHQTGI-
PARGSHYIANNKKM.

14. The method of claim 12 wherein said bacterial host cell is E. coli.

15. A method for producing biologically active ciliary neurotrophic factor in bacteria, comprising the steps of:

(a) culturing a bacterial cell transformed with a bacterial expression vector comprising a nucleic acid, which nucleic acid (i) hybridizes to a nucleic acid comprising the nucleotide sequence:
ATGGCTTTCACAGAGCATTCACCGCTGACCCCTCACCGTCGGGACCTCTGTAGCCGCTCTATCTGGCTAGCAAGGAAGATTCGTTCAGACCTGACTGCTCTTACGGAATCCTATGTGAAGCATCAGGGCCTGAACAAGAACATCAACCTGGACTCTGCGGATGGGATGCCAGTGGCAAGCACTGATCAGTGGAGTGAGCTGACCGAGGCAGAGCGACTCCAAGAGAACCTTCAAGCTTATCGTACCTTCCATGTTTTGTTGGCCAGGCTCTTAGAAGACCAGCAGGTGCATTTTACCCCAACCGAAGGTGACTTCCATCAAGCTATACATACCCTTCTTCTCCAAGTCGCTGCCTTTGCATACCAGATAGAGGAGTTAATGATACTCCTGGAATACAAGATCCCCCGCAATGAGGCTGATGGGATGCCTATTAATGTTGGAGATGGTGGTCTCTTTGAGAAGAAGCTGTGGGGCCTAAAGGTGCTGCAGGA GCTTTCACAGTGGACAGTAAGGTCCATCCATGACCTTCGTTTCATTTCTTCTCATC AGACTGGGATCCCAGCACGTGGGAGCCATTATATTGCTAACAACAAGAAAATG or its complement, said hybridization occurring under conditions comprising incubating for 12 to 18 hours in 5×SSCP and 50% formamide at 68° C., washing in 5×SSCP and 50% formamide at 42° C. for 30 minutes, and washing in 2×SSCP for 20 to 30 minutes at room temperature, and (ii) encodes a protein having activity in the chick embryo ciliary ganglion assay; and (b) isolating said protein.

16. The method of claim 15 wherein said bacterial cell is *E. coli.*

17. A bacterial expression vector comprising the nucleic acid of claim 15, wherein said vector is able to replicate in a bacterial cell and expresses in a bacterial cell a protein having activity in the chick embryo ciliary ganglion assay.

18. A method for producing biologically active human ciliary neurotrophic factor in bacteria, comprising the steps of:

(a) culturing a bacterial cell transformed with a bacterial expression vector comprising a nucleic acid, which nucleic acid
  (i) hybridizes to a nucleic acid comprising the nucleotide sequence:
  ATGGCTTTCACAGAGCATTCACCGCTGACCCCTCACCGTCGGGACCTCTGTAGCCGCTCTATCTGGCTAGCAAGGAAGATTCGTTCAGACCTGACTGCTCTTACGGAATCCTATGTGAAGCATCAGGGCCTGAACAAGAACATCAACCTGGACTCTGCGGATGGGATGCCAGTGGCAAGCACTGATCAGTGGAGTGAGCTGACCGAGGCAGAGCGACTCCAAGAGAACCTTCAAGCTTATCGTACCTTCCATGTTTTGTTGGCCAGGCTCTTAGAAGACCAGCAGGTGCATTTTACCCCAACCGAAGGTGACTTCCATCAAGCTATACATACCCTTCTTCTCCAAGTCGCTGCCTTTGCATACCAGATAGAGGAGTTAATGATACTCCTGGAATACAAGATCCCCCGCAATGAGGCTGATGGGATGCCTATTAATGTTGGAGATGGTGGTCTCTTTGAGAAGAAGCTGTGGGGCCTAAAGGTGCTGCAGGA GCTTTCACAGTGGACAGTAAGGTCCATCCATGACCTTCGTTTCATTTCTTCTCATC AGACTGGGATCCCAGCACGTGGGAGCCATTATATTGCTAACAACAAGAAAATG or its complement, said hybridization occurring under conditions comprising incubating for 12 to 18 hours in 6×SSC, 1×Denhardt's, 50 mM EDTA (pH 8.0), 0.5% SDS and 100 µg/ml of tRNA at 68° C., washing twice in 6×SSC, 0.5% SDS at 68° C. for 20 minutes each, washing in 2×SSC at 68° C. for 20 minutes, and washing in 0.1×SSC for 2 minutes at room temperature, and (ii) encodes a protein having activity in the chick embryo ciliary ganglion assay; and (b) isolating said protein.

19. The method of claim 18 wherein said bacterial cell is *E. coli.*

20. A bacterial expression vector comprising the nucleic acid of claim 18, wherein said vector is able to replicate in a bacterial cell and expresses in a bacterial cell a protein having activity in the chick embryo ciliary ganglion assay.

21. A method for producing biologically active human ciliary neurotrophic factor in bacteria, comprising the steps of:

(a) culturing a bacterial cell transformed with a bacterial expression vector comprising a nucleic acid, which nucleic acid
  (i) hybridizes to a nucleic acid comprising the nucleotide sequence:
  ATGGCTTTCACAGAGCATTCACCGCTGACCCCTCACCGTCGGGACCTCTGTAGCCGCTCTATCTGGCTAGCAAGGAAGATTCGTTCAGACCTGACTGCTCTTACGGAATCCTATGTGAAGCATCAGGGCCTGAACAAGAACATCAACCTGGACTCTGCGGATGGGATGCCAGTGGCAAGCACTGATCAGTGGAGTGAGCTGACCGAGGCAGAGCGACTCCAAGAGAACCTTCAAGCTTATCGTACCTTCCATGTTTTGTTGGCCAGGCTCTTAGAAGACCAGCAGGTGCATTTTACCCCAACCGAAGGTGACTTCCATCAAGCTATACATACCCTTCTTCTCCAAGTCGCTGCCTTTGCATACCAGATAGAGGAGTTAATGATACTCCTGGAATACAAGATCCCCCGCAATGAGGCTGATGGGATGCCTATTAATGTTGGAGATGGTGGTCTCTTTGAGAAGAAGCTGTGGGGCCTAAAGGTGCTGCAGGA GCTTTCACAGTGGACAGTAAGGTCCATCCATGACCTTCGTTTCATTTCTTCTCATC AGACTGGGATCCCAGCACGTGGGAGCCATTATATTGCTAACAACAAGAAAATG or its complement, said hybridization occurring under conditions comprising incubating for 12 to 18 hours in a 0.5 M sodium phosphate, pH 7.2, 7% SDS, 1% crystalline BSA and 1 mM EDTA (pH 8.0) at 68° C., washing twice in 40 mM phosphate buffer (pH 7.2), 5% SDS, 0.5% BSA (Fraction V), 1 mM EDTA (pH 8.0) for 30–60 minutes at 68° C., and washing twice in 40 mM phosphate (pH 7.2), 1 mM EDTA (pH 8.0) and 1% SDS for 30–60 minutes at 68° C., and (ii) encodes a protein having activity in the chick embryo ciliary ganglion assay; and (b) isolating said protein.

22. The method of claim 21 wherein said bacterial cell is *E. coli.*

23. A bacterial expression vector comprising the nucleic acid of claim 21, wherein said vector is able to replicate in a bacterial cell and expresses in a bacterial cell a protein having activity in the chick embryo ciliary ganglion assay.

24. A method for producing biologically active human ciliary neurotrophic factor in bacteria, comprising the steps of:
(a) culturing a bacterial cell transformed with a bacterial expression vector comprising a nucleic acid, which nucleic acid
  (i) hybridizes to a nucleic acid comprising the nucleotide sequence:
  ATGGCTTTCACAGAGCATTCACCGCTGACCCCTCACCGTCGGGACCTCTGTAGCCGCTCTATCTGGCTAGCAAGGAAGATTCGTTCAGACCTGACTGCTCTTACGGAATCCTATGTGAAGCATCAGGGCCTGAACAAGAACATCAACCTGGACTCTGCGGATGGGATGCCAGTGGCAAGCACTGATCAGTGGAGTGAGCTGACCGAGGCAGAGCGACTCCAAGAGAACCTTCAAGCTTATCGTACCTTCCATGTTTTGTTGGCCAGGCTCTTAGAAGACCAGCAGGTGCATTTTACCCCAACCGAAGGTGACTTCCATCAAGCTATACATACCCTTCTTCTCCAAGTCGCTGCCTTTGCATACCAGATAGAGGAGTTAATGATACTCCTGGAATACAAGATCCCCCGCAATGAGGCTGATGGGATGCCTATTAATGTTGGAGATGGTGGTCTCTTTGAGAAGAAGCTGTGGGGCCTAAAGGTGCTGCAGGA GCTTTCACAGTGGACAGTAAGGTCCATCCATGACCTTCGTTTCATTTCTTC TCATC AGACTGGGATCCCAGCACGTGGGAGCCATTATATTGCTAACAACAAGAAAATG
or its complement, said hybridization occurring under conditions comprising incubating for 16 hours in 5×SSC and 50% formamide at 37° C., washing three times in chloroform for 10 minutes each, washing in 6×SSC for 10 minutes, washing in 2×SSC for 10 minutes, and washing in 2×SSC containing 20 µg/ml of pancreatic ribonuclease, and
  (ii) encodes a protein having activity in the chick embryo ciliary ganglion assay; and
(b) isolating said protein.

25. The method of claim 24 wherein said bacterial cell is *E. coli*.

26. A bacterial expression vector comprising the nucleic acid of claim 25, wherein said vector is able to replicate in a bacterial cell and expresses in a bacterial cell a protein having activity in the chick embryo ciliary ganglion assay.

27. The method of claim 15, 18, 21 or 24 wherein said protein comprises the amino acid sequence:
MAFTEHSPLTPHRRDLCSRSIWLARKIRSDLTALTESYVKHQGLNKNINLDSADGMP VASTDQWSELTEAERLQENLQAYRTFHVLLARLLEDQQVHFTPTEGDFHQAI HTLLL QVAAFAYQIEELMILLEYKIPRNEADGMPINVGDGGLFEKKLWGLKVLQELSQWTV RSIHDLRFISSHQTGIPARGSHYIANNKKM.

28. A bacterial cell transformed with the bacterial expression vector of claim 17, 20, 23 or 26.

29. The bacterial cell of claim 28 which is *E. coli*.

30. A method for producing a protein having activity in the chick embryo ciliary ganglion assay comprising culturing a bacterial cell transformed with the bacterial expression vector of claim 17, 20, 25 or 26 and isolating said protein.

31. A recombinant expression system for producing a protein having activity in the chick embryo ciliary ganglion assay comprising a bacterial cell transformed with a bacterial vector of claim 17, 20, 23 or 26.

32. The recombinant expression system of claim 31 wherein said bacterial cell is *E. coli*.

* * * * *